US011060062B2

(12) United States Patent
Ameri et al.

(10) Patent No.: US 11,060,062 B2
(45) Date of Patent: Jul. 13, 2021

(54) GENERATION OF GLUCOSE-RESPONSIVE BETA CELLS

(71) Applicant: University of Copenhagen, Copenhagen K (DK)

(72) Inventors: Jacqueline Ameri, Malmö (SE); Henrik Semb, Bjarred (SE)

(73) Assignee: University of Copenhagen, Copenhagen K (DK)

(*) Notice: Subject to any disclaimer, the term of this patent is extended or adjusted under 35 U.S.C. 154(b) by 0 days.

(21) Appl. No.: 15/852,900

(22) Filed: Dec. 22, 2017

(65) Prior Publication Data
US 2019/0127703 A1    May 2, 2019

(30) Foreign Application Priority Data
Oct. 26, 2017  (CA) ..................... 2983845

(51) Int. Cl.
C12N 5/071   (2010.01)
A61K 35/39   (2015.01)
A61P 3/10    (2006.01)

(52) U.S. Cl.
CPC ............ C12N 5/0676 (2013.01); A61K 35/39 (2013.01); A61P 3/10 (2018.01); *C12N 2500/90* (2013.01); *C12N 2501/115* (2013.01); *C12N 2501/16* (2013.01); *C12N 2501/33* (2013.01); *C12N 2501/385* (2013.01); *C12N 2501/40* (2013.01); *C12N 2501/999* (2013.01); *C12N 2506/03* (2013.01)

(58) Field of Classification Search
CPC .............. C12N 5/0676; C12N 2506/03; C12N 2501/16; C12N 2501/385; C12N 2501/115; C12N 2501/33; C12N 2501/40; C12N 2500/90; C12N 2501/999; A61K 35/39; A61P 3/10
See application file for complete search history.

(56) References Cited

U.S. PATENT DOCUMENTS

| | | | |
|---|---|---|---|
| 6,436,704 B1* | 8/2002 | Roberts | C12N 5/0678 435/325 |
| 7,510,876 B2 | 3/2009 | D'Amour et al. | |
| 7,534,608 B2 | 5/2009 | Martinson et al. | |
| 7,695,965 B2 | 4/2010 | Martinson et al. | |
| 7,993,920 B2 | 8/2011 | Martinson et al. | |
| 8,129,182 B2 | 3/2012 | D'Amour et al. | |
| 8,278,106 B2 | 10/2012 | Martinson et al. | |
| 8,338,170 B2 | 12/2012 | Kelly et al. | |
| 8,425,928 B2 | 4/2013 | Martinson et al. | |
| 8,551,779 B2 | 10/2013 | Hald et al. | |
| 8,603,811 B2 | 12/2013 | D'Amour et al. | |
| 8,633,024 B2 | 1/2014 | D'Amour et al. | |
| 8,647,873 B2 | 2/2014 | D'Amour et al. | |
| 8,741,643 B2 | 6/2014 | Rezania et al. | |
| 8,927,274 B2 | 1/2015 | Itskovitz-Eldor et al. | |
| 9,045,736 B2 | 6/2015 | Kelly et al. | |
| 9,096,832 B2 | 8/2015 | Xu | |
| 9,132,226 B2 | 9/2015 | Martinson et al. | |
| 9,175,260 B2 | 11/2015 | Dalton et al. | |
| 9,506,034 B2 | 11/2016 | Kelly et al. | |
| 9,585,917 B2 | 3/2017 | Martinson et al. | |
| 9,725,699 B2 | 8/2017 | Rezania et al. | |
| 9,744,195 B2 | 8/2017 | Xu | |
| 9,764,062 B2 | 9/2017 | Martinson et al. | |
| 9,913,930 B2 | 3/2018 | Martinson et al. | |
| 9,980,986 B2 | 5/2018 | Martinson et al. | |
| 10,000,739 B2 | 6/2018 | Kume et al. | |
| 10,266,808 B2 | 4/2019 | Kelly et al. | |
| 10,272,179 B2 | 4/2019 | Martinson et al. | |
| 10,370,645 B2 | 8/2019 | D'Amour et al. | |
| 10,456,424 B2 | 10/2019 | Xu | |
| 10,517,901 B2 | 12/2019 | Martinson et al. | |
| 2009/0263896 A1 | 10/2009 | Kelly et al. | |
| 2009/0311782 A1 | 12/2009 | Chiou et al. | |
| 2010/0255580 A1 | 10/2010 | Rezania | |
| 2014/0030234 A1 | 1/2014 | Kim et al. | |
| 2014/0329704 A1 | 11/2014 | Melton et al. | |
| 2015/0104430 A1 | 4/2015 | Keller et al. | |
| 2016/0355787 A1 | 12/2016 | D'Amour et al. | |
| 2017/0044498 A1 | 2/2017 | Kelly et al. | |
| 2018/0179593 A1 | 6/2018 | Melton et al. | |
| 2019/0128885 A1 | 5/2019 | Nostro et al. | |
| 2019/0201582 A1 | 7/2019 | Martinson et al. | |
| 2019/0390169 A1 | 12/2019 | Osafune et al. | |
| 2020/0030383 A1 | 1/2020 | Xu | |
| 2020/0048614 A1 | 2/2020 | Rezania et al. | |

FOREIGN PATENT DOCUMENTS

| | | |
|---|---|---|
| EP | 1743663 | 1/2007 |
| EP | 2 562 248 A1 | 2/2013 |
| EP | 2 644 694 A1 | 10/2013 |
| EP | 2 185 695 B1 | 2/2015 |
| EP | 2 356 227 B1 | 3/2018 |
| EP | 3 363 444 A1 | 8/2018 |
| EP | 2 021 462 B1 | 1/2019 |
| EP | 3 527 658 A1 | 2/2019 |
| EP | 1 999 253 B1 | 5/2019 |
| EP | 2 356 213 B1 | 5/2019 |
| EP | 2 844 739 B1 | 6/2019 |
| EP | 2 185 693 B1 | 7/2019 |
| EP | 2 650 359 A1 | 10/2019 |
| EP | 3 591 040 A1 | 1/2020 |
| EP | 3 594 323 A1 | 1/2020 |

(Continued)

OTHER PUBLICATIONS

Ghazizadeh et al. ROCKII inhibition promotes the maturation of human pancreatic beta-like cells. Nature Communications (online Oct. 21, 2017), 8(298), pp. 1-12. (Year: 2017).*
Zhang et al. The role of noggin in regulation of high glucose-induced apoptosis and insulin secretion in INS-1 rat beta cells. Iran J Basic Med Sci (2015); 18:1137-1142. (Year: 2015).*

(Continued)

*Primary Examiner* — Sean C. Barron
(74) *Attorney, Agent, or Firm* — Julie K. Staple; Dinsmore & Shohl LLP

(57) ABSTRACT

The present invention relates to a method for generating glucose-responsive beta cells.

27 Claims, 29 Drawing Sheets

(56) References Cited

FOREIGN PATENT DOCUMENTS

| | | |
|---|---|---|
| WO | WO 03/055992 | 7/2003 |
| WO | WO 2004/010933 | 2/2004 |
| WO | WO 2005/045001 | 5/2005 |
| WO | WO 2005/063971 | 7/2005 |
| WO | WO 2005/116073 | 12/2005 |
| WO | WO 2006/083782 | 8/2006 |
| WO | WO 2006/094286 | 9/2006 |
| WO | WO 2007/042225 | 4/2007 |
| WO | WO 2007/103282 | 9/2007 |
| WO | WO 2007/127927 | 11/2007 |
| WO | WO 2007/130474 | 11/2007 |
| WO | WO 2008/094597 | 8/2008 |
| WO | WO 2009/012428 | 1/2009 |
| WO | WO 2009/018453 | 2/2009 |
| WO | WO 2009/083502 | 7/2009 |
| WO | WO 2009/121958 | 10/2009 |
| WO | WO 2009/126927 | 10/2009 |
| WO | WO 2009/131568 | 10/2009 |
| WO | WO 2009/132063 | 10/2009 |
| WO | WO 2010/053472 | 5/2010 |
| WO | WO 2010/057039 | 5/2010 |
| WO | WO 2011/128897 | 10/2011 |
| WO | WO 2012/056997 A1 | 5/2012 |
| WO | WO 2012/070014 | 5/2012 |
| WO | WO 2013/086008 | 6/2013 |
| WO | WO 2013/163739 | 11/2013 |
| WO | WO 2013/188138 | 12/2013 |
| WO | WO 2014/024183 | 2/2014 |
| WO | WO 2014/127219 | 8/2014 |
| WO | WO 2014/160413 | 10/2014 |
| WO | WO 2014/201167 | 12/2014 |
| WO | WO 2015/173576 | 11/2015 |
| WO | WO 2015/173578 | 11/2015 |
| WO | WO-2016044721 A1 * | 3/2016 ........... A61K 9/5036 |
| WO | WO 2016/138464 | 9/2016 |
| WO | WO 2018/159805 A1 | 9/2018 |
| WO | WO 2018/229179 A1 | 12/2018 |

OTHER PUBLICATIONS

Suzuki et al. TGF-β Signaling Regulates Pancreatic β-Cell Proliferation through Control of Cell Cycle Regulator p27 Expression. Acta Histochem Cytochem, 46(2), 51-58, 2013. (Year: 2013).*
Recombinant Human Noggin Protein (Cat. # 6057-NG). Retrived from https://www.rndsystems.com/products/recombinant-human-noggin-protein_6057-ng.*
Prabakar et al. Generation of Glucose-Responsive, Insulin-Producing Cells From Human Umbilical Cord Blood-Derived Mesenchymal Stem Cells. Cell Transplantation (2012), 21, 1321-1339. (Year: 2012).*
Ameri et al. Efficient Generation of Glucose-Responsive Beta Cells from Isolated GP2+ Human Pancreatic Progenitors. Cell Reports (Apr. 4, 2017), 19, 36-49. (Year: 2017).*
Cebola et al. 2015 "TEAD and YAP regulate the enhancer network of human embryonic pancreatic progenitors" Nature Cell biology, vol. 17, No. 5.
D'Amour et al. 2006 "Production of pancreatic hormone-expressing endocrine cells from human embryonic stem cells" Nature Biotechnology, vol. 24, No. 11, 1392-1401.
Diep et al. 2012 "Down-Regulation of Yes Associated Protein 1 Expression Reduces Cell Proliferation and Clonogenicity of Pancreatic Cancer Cells" PLoS ONE, March, vol. 7, Issue 3, e32783-e32783.
Jiang et al. 2011 "CD24: A Novel Surface Marker for PDX1-Positive Pancreatic Progenitors Derived from Human Embryonic Stem Cells" Stem Cells; 29, 609-617.
Kumar, et al. 2014 "Recent Developments in p-Cell Differentiation of Piuripotent Stem Cells Induced by Small and Large Molecules" Int. J. Mol. Sci. 2014,15, 23418-23447.
Ogaki et al. 2011 "An expression profile analysis of ES cell-derived definitive endodermal cells and Pdxl-expressing cells" BMC Developmental Biology; 11, 1-15.
Rezania et al. 2013 "Enrichment of Human Embryonic Stem Cell-Derived NKX6.1-Expressing Pancreatic Progenitor Cells Accelerates the Maturation of Insulin-Secreting Cells In Vivo" Stem Cells; 31, 2432-2442.
Seymour et al. 2007 "SOX9 is required for maintenance of the pancreatic progenitor cell pool" PNAS, vol. 104, No. 6, 1865-1870.
Zhang et al. 2013 "miR-375 Inhibits Proliferation of Mouse Pancreatic Progenitor Cells by Targeting YAPI" Cell Physiol Biochem; 32, 1808-1817.
Ameri et al: Efficient generation of glucose-responsive beta cells from isolated GP2+ human pancreatic progenitors. Cell Reports,19,36-49, doi: 10.1016/j.celrep.2017.03.032.
Ameri, J. et al. (2010) Stem Cells 28(1):45-56, FGF2 Specifies hESC-Derived Definitive Endoderm into Foregut/Midgut Cell Lineages in a Concentration-Dependent Manner.
Aoi, T. et al. (2008) Nihon Rinsho. 66(5):850-6, [Advance in study of induced pluripotent stem cells (iPS cells)].
Attali et al.: Control of beta-Cell Differentiation by the Pancreatic Mesenchyme, Diabetes, 56, 1248-58, 2007.
Besson et al.: CDK Inhibitors: Cell Cycle Regulators and Beyond, Dev Cell, 14, 159-69, 2008.
Bhushan et al.: Fgf10 is essential for maintaining the proliferative capacity of epithelial progenitor cells during early pancreatic organogenesis, Development, 128, 5109-17, 2001.
Bonfanti et al.: Ex Vivo Expansion and Differentiation of Human and Mouse Fetal Pancreatic Progenitors Are Modulated by Epidermal Growth Factor, Stem Cells Dev, 24, 1766-78, 2015.
Bruni et al.: Islet cell transplantation for the treatment of type 1 diabetes: recent advances and future challenges, Diabetes Metab Syndr Obes, 7, 211-23, 2014.
Castaing et al.: Ex Vivo Analysis of Acinar and Endocrine Cell Development in the Human Embryonic Pancreas, Dev Dyn, 234, 339-45, 2005.
Cheng et al.: Self-Renewing Endodermal Progenitor Lines Generated from Human Pluripotent Stem Cells, Cell Stem Cell, 10, 371-84, 2012.
Chung, Y. et al. (2008) Cell Stem Cell. 2(2):113-7, Human Embryonic stem cell lines generated without embryo desctruction.
Cogger et al.: Glycoprotein 2 is a specific cell surface marker of human pancreatic progenitors, Nat Commun. Aug. 24, 2017;8(1):331. doi: 10.1038/s41467-017-00561-0.
D'Amour et al.: Efficient differentiation of human embryonic stem cells to definitive endoderm, Nat Biotechnol, 23, 1534-41, 2005.
Donovan et al.: Transforming growth factor-b and breast cancer Cell cycle arrest by transforming growth factor-b and its disruption in cancer, Breast Cancer Res, 2, 116-24, 2000.
Elghazi et al.: Role for FGFR2IIIb-mediated signals in controlling pancreatic endocrine progenitor cell proliferation, Proc Natl Acad Sci U S A, 99, 3884-9, 2002.
Fateye et al., Photochem Photobiol. Sep.-Oct. 2012;88(5):1265-72, Combination of phosphatidylinositol 3-kinases pathway inhibitor and photodynamic therapy in endothelial and tumor cells.
Fischer et al.: NANOG Reporter Cell Lines Generated by Gene Targeting in Human Embryonic Stem Cells, PLoS One, 5, 2010.
Funa et al.; b-Catenin Regulates Primitive Streak Induction through Collaborative Interactions with SMAD2/SMAD3 and OCT4, Cell Stem Cell, 16, 639-52, 2015.
Gu et al.: Direct evidence for the pancreatic lineage: NGN3+ cells are islet progenitors and are distinct from duct progenitors, Development, 129, 2447-57, 2002.
Guo et al.: Factors Expressed by Murine Embryonic Pancreatic Mesenchyme Enhance Generation of Insulin-Producing Cells From hESCs, Diabetes, 62, 1581-92, 2013.
Heins et.al. (2004) Stem Cells, 22(3):367-76. Derivation, characterization, and differentiation of human embryonic stem cells.
Herrera: Defining the cell lineages of the islets of langerhans using transgenic mice, Int J Dev Biol, 46, 97-103, 2002.
Hoebeeck et al.; Rapid detection of VHL exon deletions using real-time quantitative PCR, Lab Invest, 85, 24-33, 2005.
Holland et al. (2006) Genesis 44(6):304-307, A mouse carrying the green fluorescent protein gene targeted to the Pdx1 locus facilitates the study of pancreas development and function.

(56) References Cited

OTHER PUBLICATIONS

Hoops et al.: Isolation of the cDNA Encoding Glycoprotein-2 (GP-2),t he Major Zymogen Granule Membrane Protein, J Biol Chem, 266, 4257-63, 1991.
Jennings et al.: Development of the Human Pancreas From Foregut to Endocrine Commitment, Diabetes, 62, 3514-22, 2013.
Jiang, J. et al. (2007), Stem Cells 25(8):1940-1953. Generation of Insulin-producing islet-like clusters from human embryonic stem cells.
Kawaguchi et al.: The role of the transcriptional regulator Ptf1a in converting intestinal to pancreatic progenitors, Nat Genet, 32, 128-34, 2002.
Kelly, O. G. et al, (2011) Nat Biotechnol. (29): 750-756, Cell-surface markers for the isolation of pancreatic cell types derived from human embryonic stem cells.
Kempf, H. et al. Adv. Drug Delivery Rev. (2016) 96, 18-30, Large-scale production of human pluripotent stem cell derived cardiomyocytes.
Kippin et al.: p21 loss compromises the relative quiescence of forebrain stem cell proliferation leading to exhaustion of their proliferation capacity, Genes Dev, 19, 756-67, 2005.
Koike et al.: Ring1B Promotes Hepatic Stem/Progenitor Cell Expansion Through Simultaneous Suppression of Cdkn1a and Cdkn2a in Mice. Hepatology, 60, 323-33, 2014.
Kopp et al.: Sox9+ ductal cells are multipotent progenitors throughout development but do not produce new endocrine cells in the normal or injured adult pancreas, Development, 138, 653-65, 2011.
Kroon, E. et al, (2008) Nat Biotechnol. 26(4):443-52, Pandreactic endoderm derived from human embryonic stem cells generates glucose-responsive insulin-secreting cells in vivo.
Miyatsuka et al.: Neurogenin3 inhibits proliferation in endocrine progenitors by inducing Cdkn1a, Proc Natl Acad Sci U S A, 108, 185-90, 2010.
Nair et al.: Islet formation in mice and men: Lessons for the generation of functional insulin-producing ß cells from human pluripotent stem cells, Curr Opin Genet Dev, 32, 171-80, 2015.
Naujok et al,: A Critical Re-Evaluation of CD24-Positivity of Human Embryonic Stem Cells Differentiated into Pancreatic Progenitors, Stem Cell Rev. 8(3):779-91, 2012.
Orford et al.: Deconstructing stem cell self-renewal: genetic insights into cell-cycle regulation, Nat Rev Genet, 9, 115-28, 2008.
Pagliuca et al. (2014) Cell. 159(2):428-39, Generation of functional human pancreatic beta cells in vitro.
Piccand et al.: Pak3 Promotes Cell Cycle Exit and Differentiation of b-Cells in the Embryonic Pancreas and Is Necessary to Maintain Glucose Homeostasis in Adult Mice, Diabetes, 63, 203-15, 2014.
Ramond et al.: Reconstructing human pancreatic differentiation by mapping specific populations during development. eLife 2017;6:e27564, doi: 10.7554/eLife.27564.
Rezania A. et al (2012) Diabetes. Aug. 2012;61(8):2016-29, Maturation of Human Embryonic stem cell-derived pancreatic progenitors into functional islet capable of treating pre-existing diabetes in mice.
Rezania et al. (2010) Eur J Pharmacol. 627(1-3):265-8, The effect of litium chloride an WIN 55,212-2-induced tolerance in isolated guinea pig ileum.
Rezania, A. et al, (2014) Nat Biotechnol. (32):1121-33, Reversal of diabetes with insulin-producing cells derived in vitro from human pluripotent stem cells.
Rezania, A. et al, (2012) Diabetes. Aug. 2012;61(8):2016-2, Maturation of human embryonic stem cell-derived pancreatic progenitors into functional islets capable of treating pre-existing diabetes in mice.
Russ et al.: Controlled induction of human pancreatic progenitors produces functional beta-like cells in vitro, EMBO J, 34, 1759-72, 2015.
Schaffer et al.: Ptf1a and Nkx6 transcription factors function as antagonistic lineage determinants in multipotent pancreatic progenitors, Dev Cell, 18, 1022-9, 2010.
Schulz et al.: A Scalable System for Production of Functional Pancreatic Progenitors from Human Embryonic Stem Cells, PLoS One, 7, e37004, 2012.
Shapiro et al. (2000) N Engl J Med 343:230-238, Islet transplantation in seven patients with type 1 diabetes mellitus using a glucocorticoid-free immunosuppressive regimen.
Shapiro et al. (2001a) Best Pract Res Clin Endocrinol Metab 15:241-264, Pancreatic islet transplantaion in the tratment of diabetes mellitus.
Shapiro et al. (2001b) British Medical Journal 322:861, Could fewer islet cells be transplanted in type 1 diabetes? Insulin independence should be dominant force in islet transplantation.
Sneddon et al.: Self-renewal of embryonic-stem-cell-derived progenitors by organ-matched mesenchyme, Nature, 491, 765-8, 2012.
Stadtfeld and Hochedlinger (2010) Genes Dev. 24(20):2239-63, Induced pluripotency: history, mechanism, and applications.
Stanger et al.: Organ size is limited by the number of embryonic progenitor cells in the pancreas but not the liver, Nature, 445, 886-91, 2007.
Takahashi and Yamanaka (2006) Cell. Aug. 25, 2006;126(4):663-76, Induction of pluripotent stem cells from mouse embryonic and adult fibroblast cultures by defined factors.
Takahashi et al. (2007) Cell 131 (5):861-872, Induction of pluripotent stem cells from adult human fibroblasts by defined factors.
Takashima et al. (2014) Cell. 158(6): 1254-1269, Resetting transcription factor control circuitry toward ground-state pluripotency in human.
Tesar et al. (2007) Nature 448(7150):196-9, New cell lines from mouse epiblast share defining features with human embryonic stem cells.
Thomson, A. et al. (1998) Science. 6;282(5391):1145-7, Embryonic stem cell lines derived from human blastocysts.
Tumaneng K. et al, (2012) Nat. Cell. Biol. 14(12), 1322-1329, YAP mediates crosstalk between the Hippo and PI3K-TOR pathways by suppressing PTEN via miR-29.
Wernig, M. et al. (2007) Nature. 448(7151):318-24, in vitro reprogamming of fibroblasts into a pluripotent ES-cell-like state.
Xie et al.: Dynamic chromatin remodeling mediated by Polycomb proteins orchestrates pancreatic differentiation of human embryonic stem cells, Cell Stem Cell, 12, 224-37, 2013.
Ye et al.: Fibroblast growth factors 7 and 10 are expressed in the human embryonic pancreatic mesenchyme and promote the proliferation of embryonic pancreatic epithelial cells, Diabetologia, 48, 277-81, 2005.
Yoon et al.: Cell cycle regulation by the intrinsically disordered proteins p21 and p27, Biochem Soc Trans, 40, 981-8, 2012.
Yu et al., (2007) Science 318:5858 1917-1920, Induced pluripotent stem cell lines derived from human somatic cells.
Yu et al.: Absence of the Major Zymogen Granule Membrane Protein, GP2, Does Not Affect Pancreatic Morphology or Secretion, J Biol Chem, 279, 50274-9, 2004.
Yu J, et al. (2009) Science vol. 324 797-801, Human induced pluripotent stem cells free of vector and transgene sequences.
Zhang et al.: Highly efficient differentiation of human ES cells and iPS cells into mature pancreatic insulin-producing cells, Cell Res, 19, 429-38, 2009.
Zhu et al.: Human pancreatic beta-like cells converted from fibroblasts, Nat Commun, 7, 10080, 2016.
Gunhanlar N et al. 2018. A simplified protocol for differentiation of electrophysiologically mature nueronal networks from human induced pluripotent stem cells. Molecular Psychiatry (2018) 23, 1336-1344.
Han X et al. 2017. Efficient and Fast Differentiation of Human Neural Stem Cells from Human Embryonic Stem Cells for Cell Therapy. vol. 2017, Article ID 9405204, 11 pages.
Kamishibahara Y et al 2016. Rho kinase inhibitor Y-27632 promotes neuronal differentiation in mouse embryonic stem cells via phosphatidylinositol 3-kinase. Neurosci Lett. Feb. 26, 2016;615:44-9. doi: 10.1016/j.neulet.2016.01.022. Epub Jan. 18, 2016.
Maldonado M et al. 2016. ROCK inhibitor primes human induced pluripotent stem cells to selectively differentiate towards mesendodermal lineage via epithelial-mesenchymal transition-like modulation. Stem Cell Res. Sep. 2016;17(2):222-227. doi: 10.1016/j.scr.2016.07.009. Epub Aug. 4, 2016.

(56) References Cited

OTHER PUBLICATIONS

Mfopou et al. 2010. Noggin, Retinoids. and Fibroblast Growth Factor Regulate Hepatic or Pancreatic Fate of Human Embryonic Stem Cells. Jun. 2010, vol. 138, Issue7, pp. 2233-2245.e14.

Vernardis et al 2017. Human embryonic and induced pluripotent stem cells maintain phenotype but alter their metabolism after exposure to ROCK inhibitor. Sci Rep. 2017; 7: 42138.

Wagner B K et al. 2016. The Genetic Landscape of b-Cell Proliferation: Toward a Road Map. Diabetes 2016;65:1789-1790.

Watanabe et al. (2007). A ROCK inhibitor permits survival of dissociated human embryonic stem cells. Nature Biotechnology vol. 25, pp. 681-686(2007).

Gao, L., et al., "Post-Passage rock inhibition induces cytoskeletal aberrations and apoptosis in Human embryonic stem cells", Stem Cell Research 41 (2019) 101641, 8 pages.

Ku, H.T., "Minireview: Pancreatic Progenitor Cells-Recent Studies" Endocrinology 149(9): 4312-4316 (2008).

Nelson, S.B., et al., "The transcription factors Nkx6.1 and Nkx6.2 possess equivalent activities in promoting beta-cell fate specification in Pdx1+ pancreatic progenitor cells", Development 134, 2491-2500 (2007).

Noguchi, H., "Pancreatic Stem/Progenitor Cells for the Treatment of Diabetes", The Review of Diabetic Studies, 7(2): 105-111 (2010).

Pederson, J.K., et al., "Endodermal expression of Nkx6 genes depends differentially on Pdx1", Developmental Biology, 288 (2005) 487-501.

Zhou, Q., et al., "A Multipotent Progenitor Domain Guides Pancreatic Organogenesis", Development Cell 13, 103-114 (2007).

\* cited by examiner

| Definitive Endoderm | | Primitive GT | PE |
|---|---|---|---|
| AA + Wnt3a | AA | RA | FGF2 +/- Nog |
| RPMI | RPMI + B27 | DMEM + B27 | DMEM + B27 |
| 1 day | 4 days | 3 days | ≥12 days |

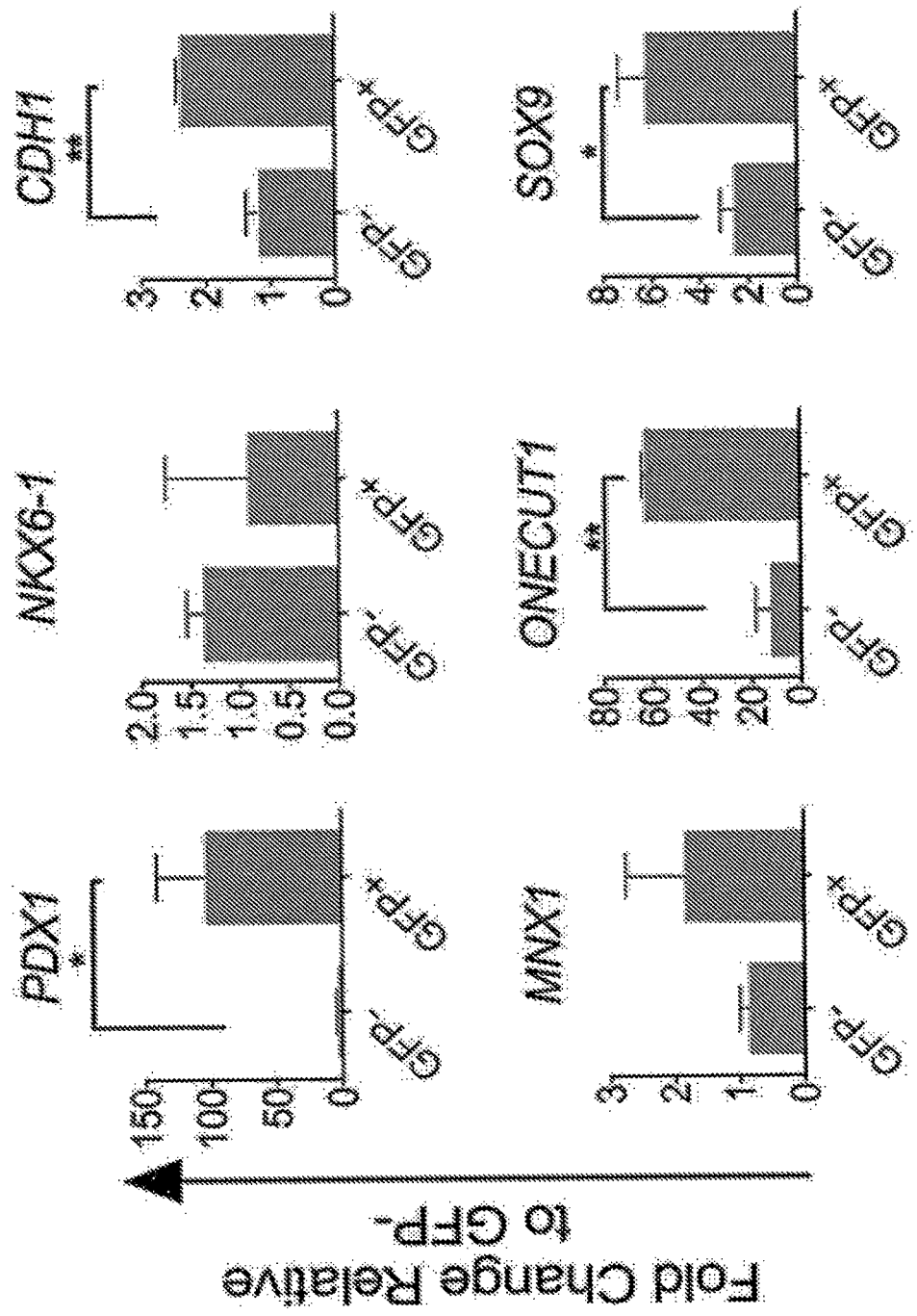

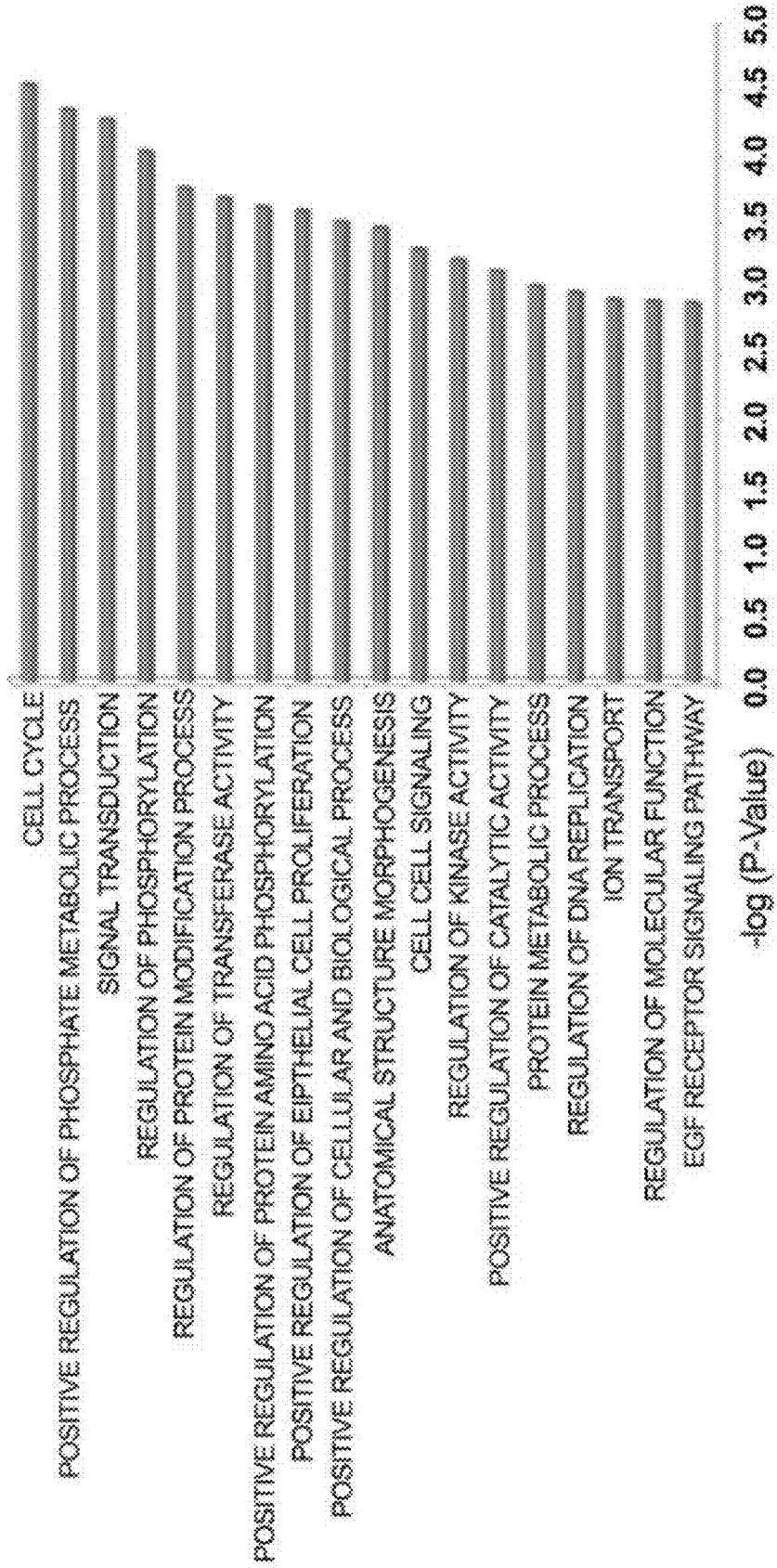

FIG. 4D
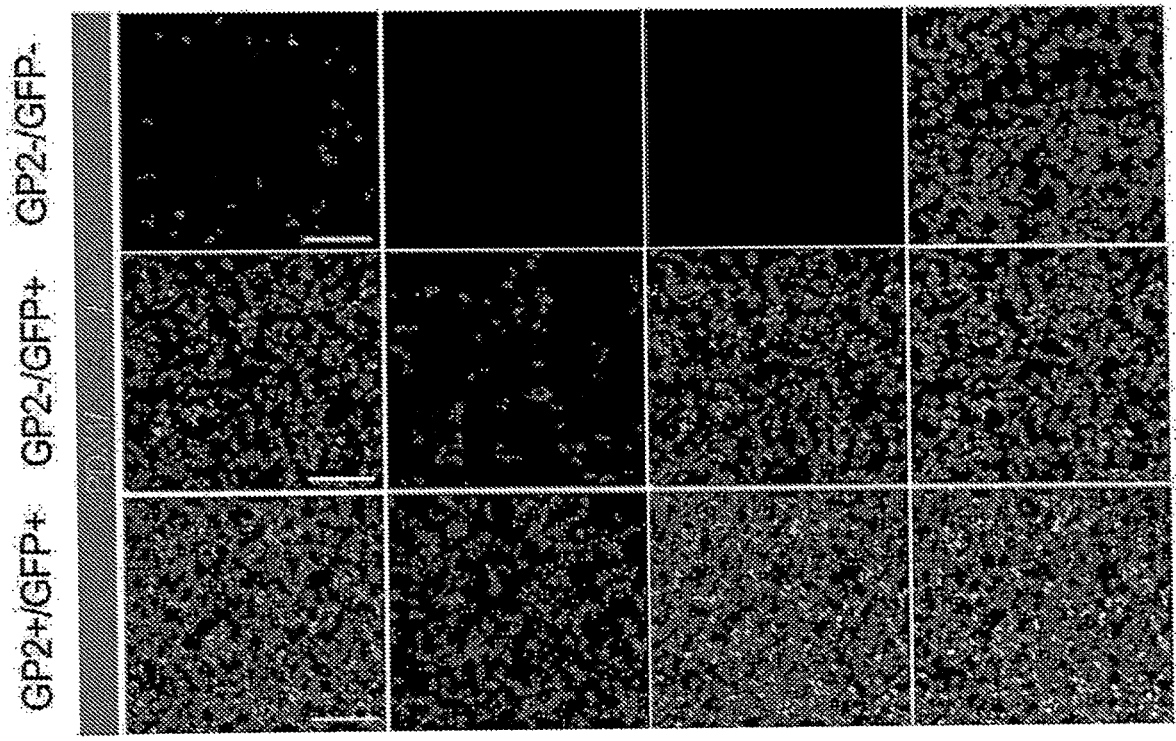
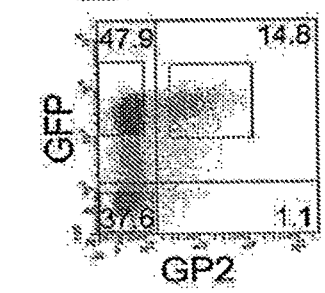
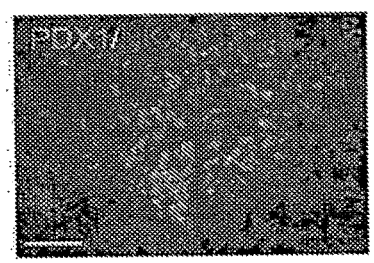
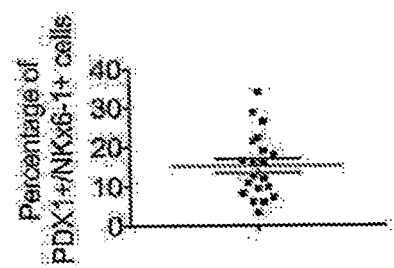
FIG. 4E
FIG. 4F
FIG. 4G

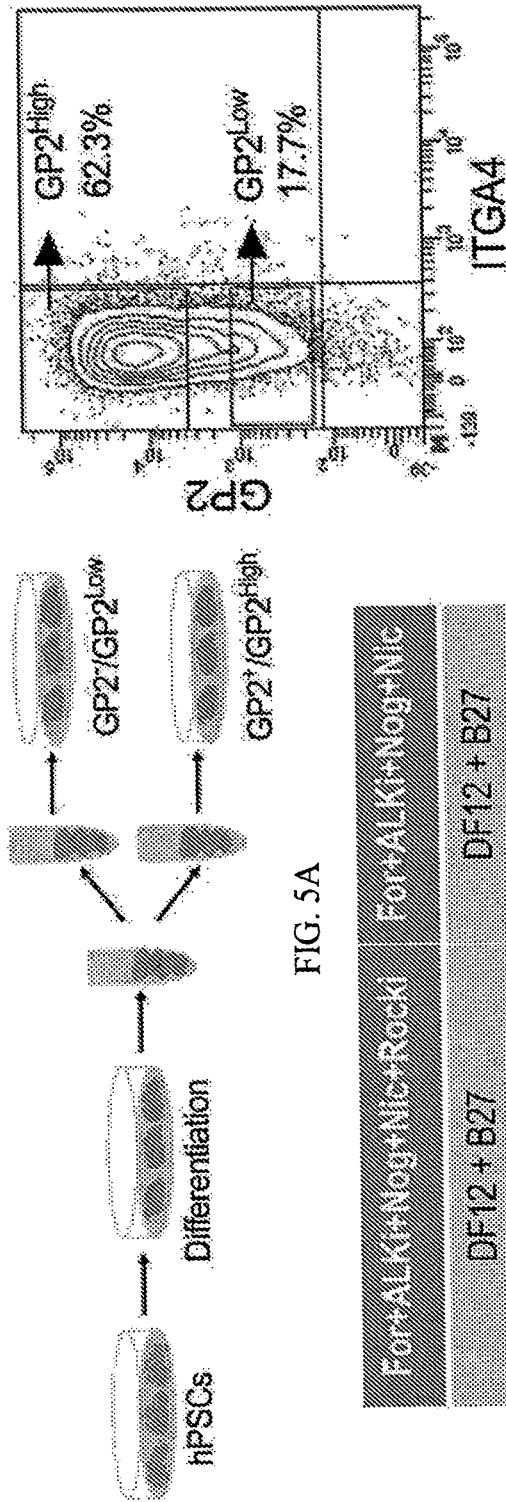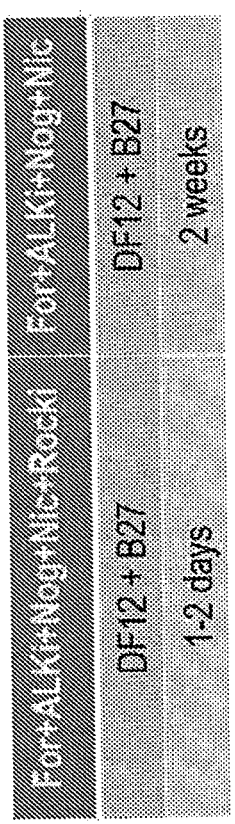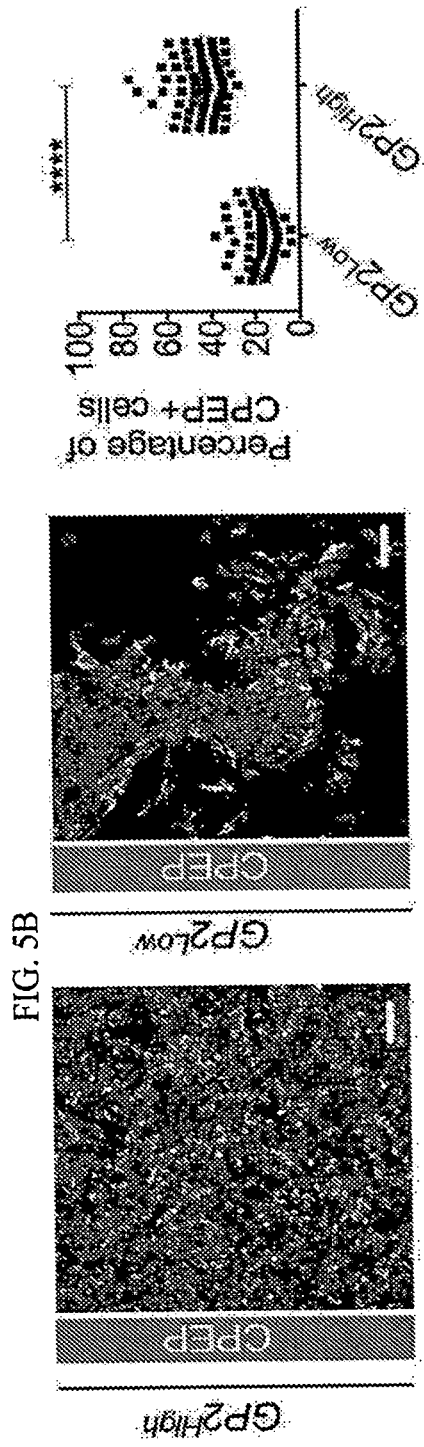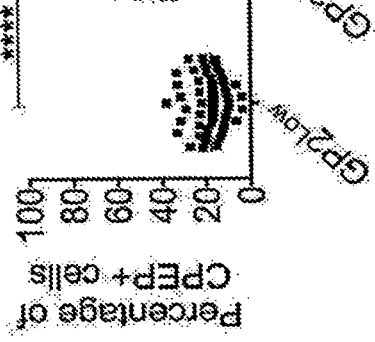
FIG. 5A
FIG. 5B
FIG. 5C
FIG. 5D
FIG. 5E FIG. 5F
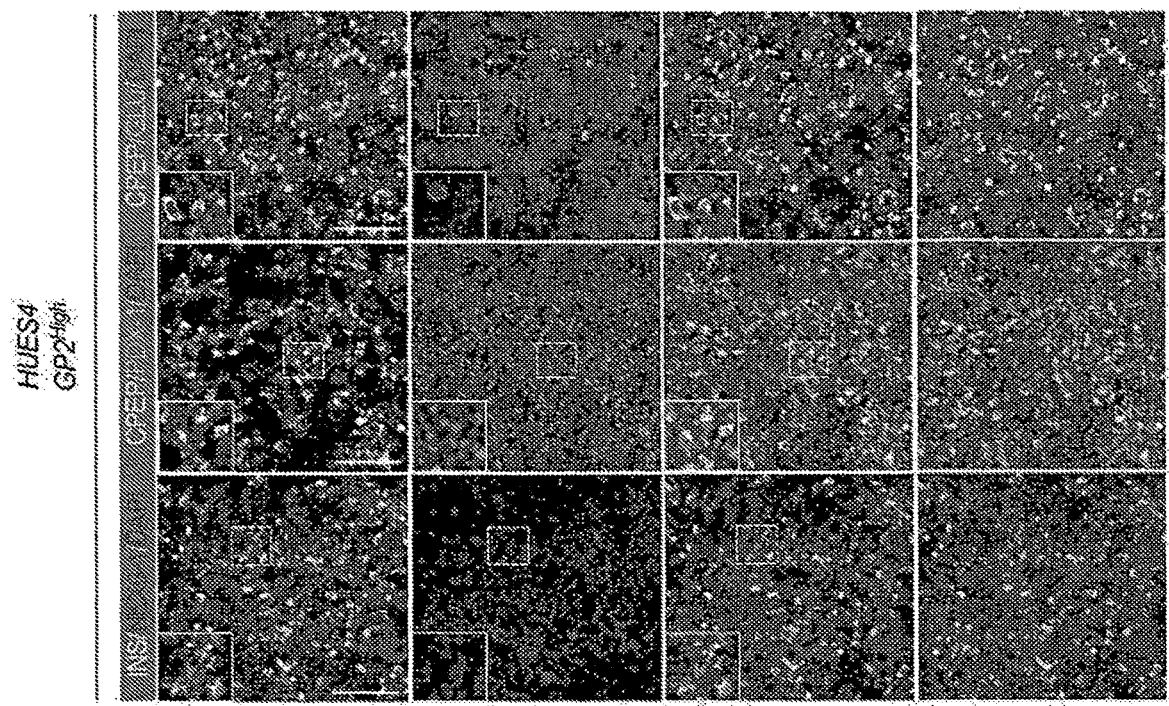
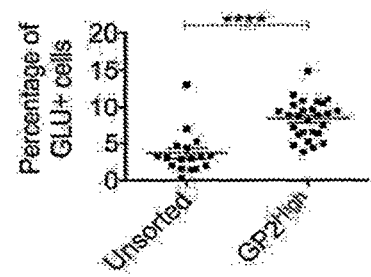
FIG. 5G
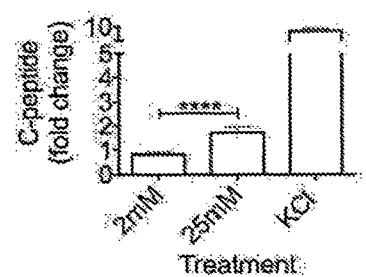
FIG. 5H

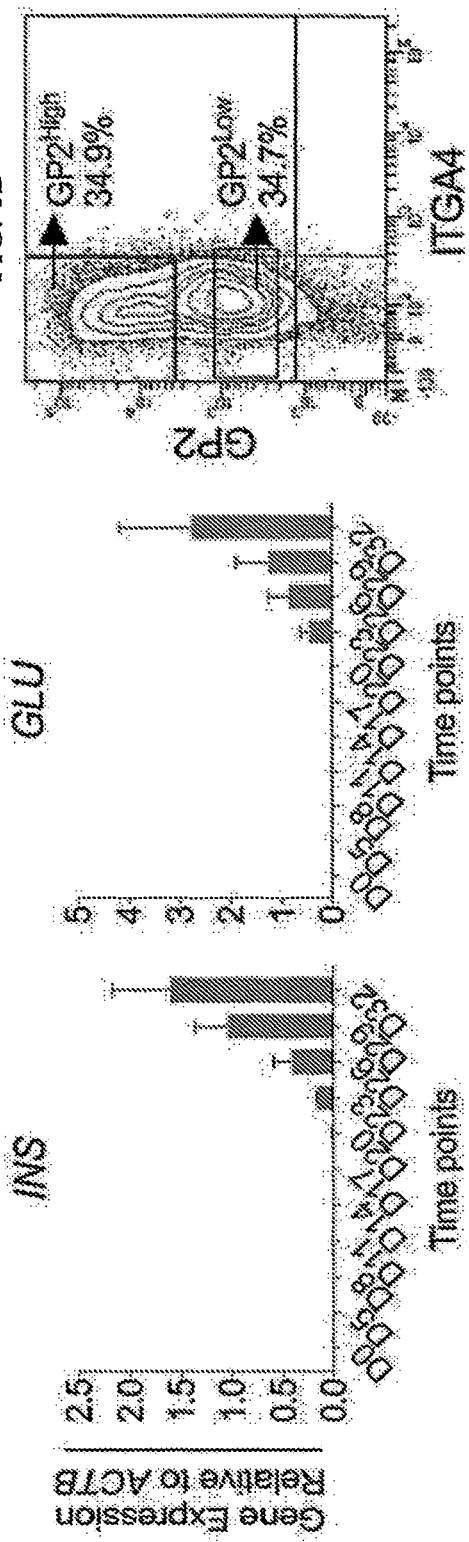
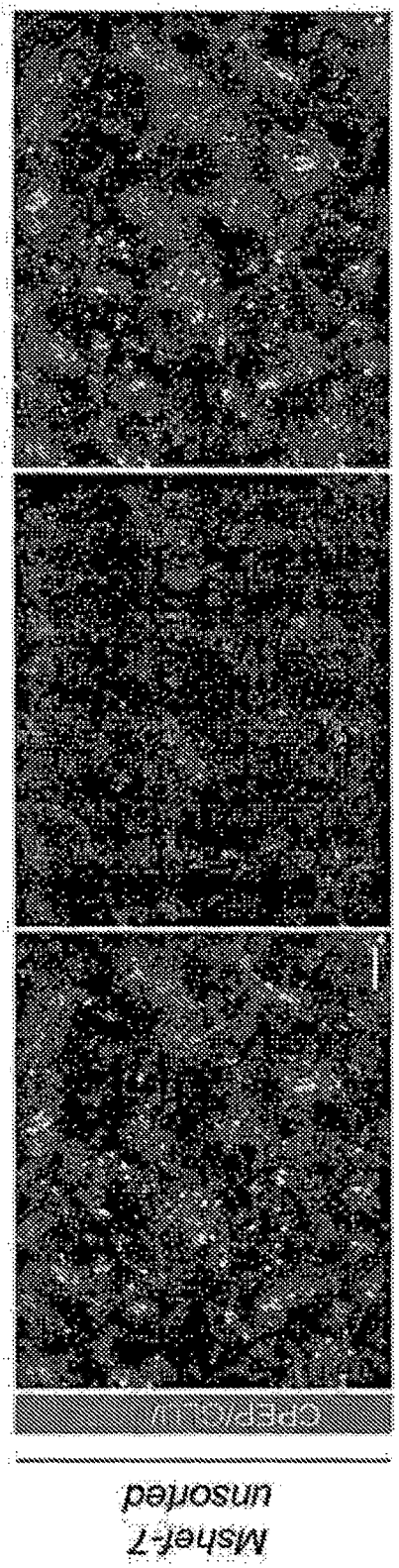
FIG. 6A
FIG. 6B
FIG. 6C

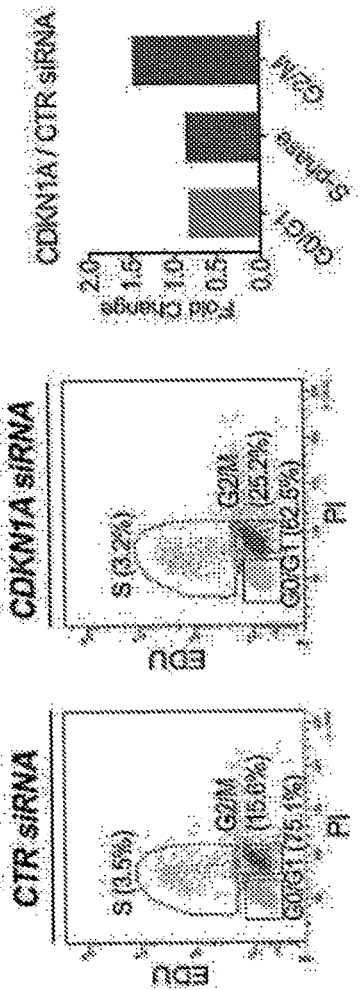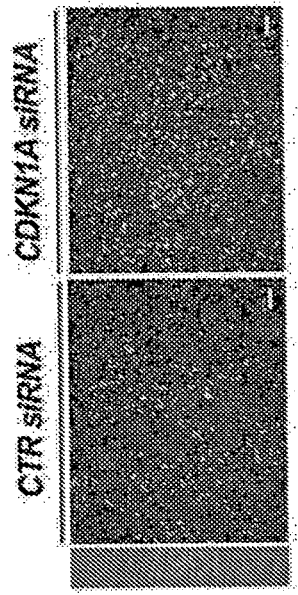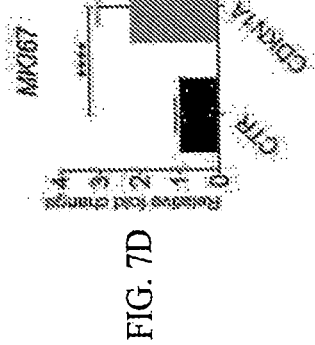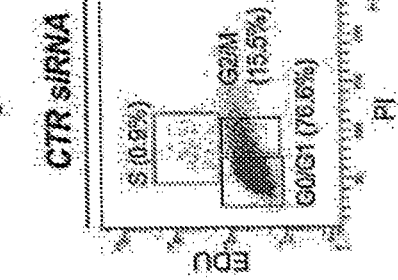

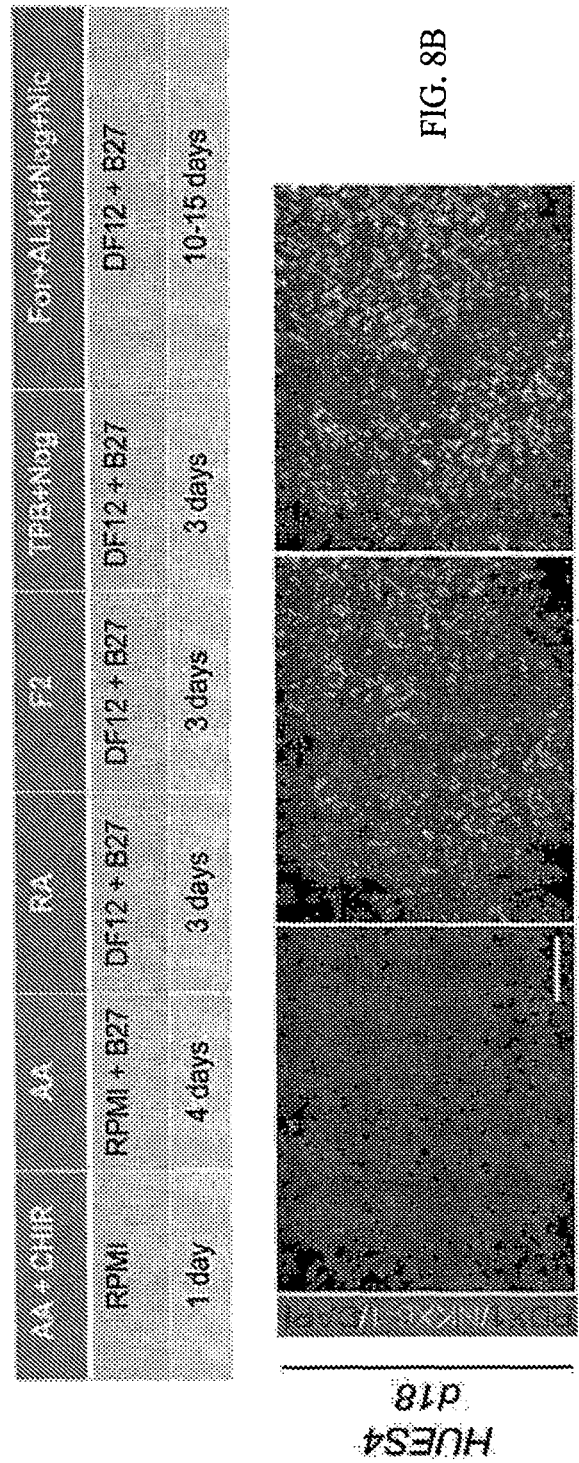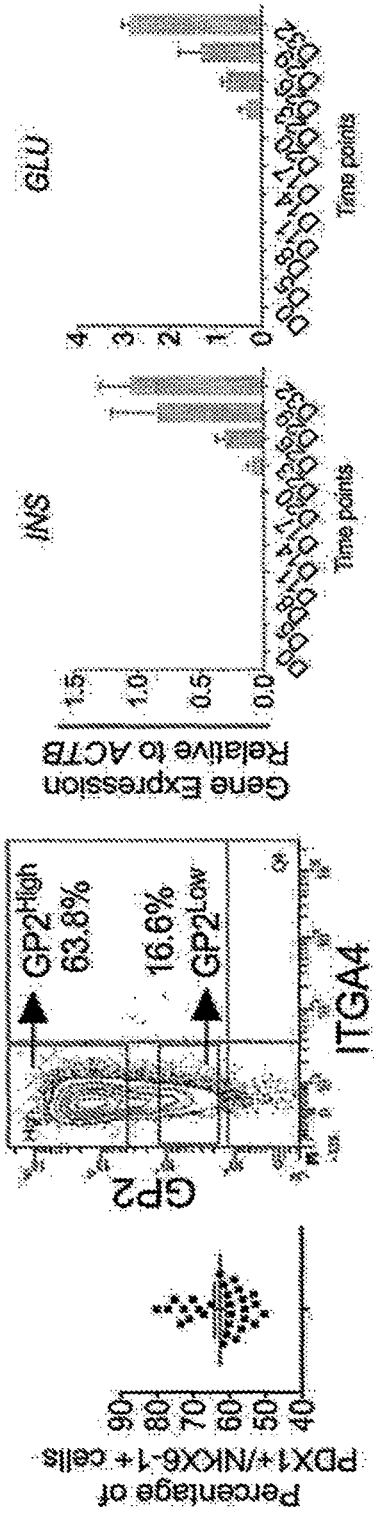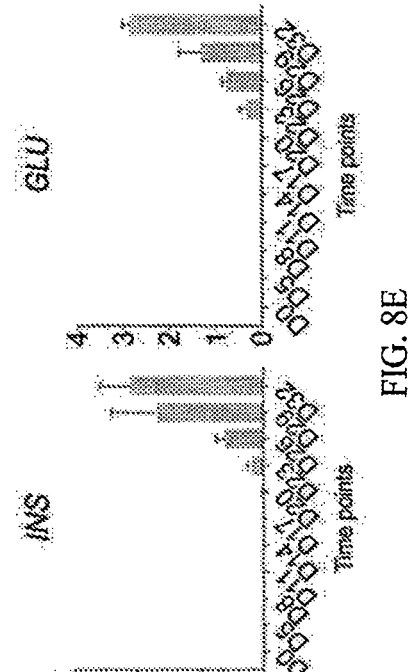
FIG. 8A
FIG. 8B
FIG. 8C
FIG. 8D
FIG. 8E

GENERATION OF GLUCOSE-RESPONSIVE BETA CELLS

RELATED APPLICATION(S)

This application claims priority under 35 U.S.C. § 119 or 365 to Canada, Application No. 2,983,845, filed Oct. 26, 2017. The entire teachings of the above application is incorporated herein by reference.

FIELD OF INVENTION

The present invention relates to a method for generating glucose-responsive beta cells from human pluripotent stem cells and human pancreatic progenitor cells.

BACKGROUND OF INVENTION

Cell therapy treatment of insulin dependent diabetes is facilitated by the production of unlimited numbers of pancreatic cells that can and will be able to function similarly to human islets. Accordingly, there is a need for producing these pancreatic cell types derived from human embryonic stem (hES) cells, as well as reliable methods for purifying such cells. For example, the use of insulin-producing β-cells derived from human embryonic stem cells (hESCs) would offer a vast improvement over current cell therapy procedures that utilize cells from donor pancreases. Currently cell therapy treatments for diabetes mellitus, such as type 1 or type 2 diabetes, which utilize cells from donor pancreases, are limited by the scarcity of high quality islet cells needed for transplant. For example, cell therapy for a single type 1 diabetic patient requires a transplant of approximately $8 \times 10^8$ pancreatic islet cells (Shapiro et al, 2000, N Engl J Med 343:230-238; Shapiro et al, 2001a, Best Pract Res Clin Endocrinol Metab 15:241-264; Shapiro et al, 2001b, British Medical Journal 322:861). As such, at least two healthy donor organs are required to obtain sufficient islet cells for a successful transplant.

Embryonic stem (ES) cells thus represent a powerful model system for the investigation of mechanisms underlying pluripotent stem cell biology and differentiation within the early embryo, as well as providing opportunities for genetic manipulation of mammals and resultant commercial, medical and agricultural applications. Furthermore, appropriate proliferation and differentiation of ES cells can potentially be used to generate an unlimited source of cells suited to transplantation for treatment of diseases that result from cell damage or dysfunction. Other pluripotent stem cells and cell lines including early primitive ectoderm-like (EPL) cells, in vivo or in vitro derived ICM/epiblast, in vivo or in vitro derived primitive ectoderm, primordial germ cells (EG cells), teratocarcinoma cells (EC cells), and pluripotent stem cells derived by dedifferentiation or by nuclear transfer can also be used.

Accordingly, there is a need for methods for generating glucose-responsive beta cells.

SUMMARY OF INVENTION

The present invention provides methods for generating glucose-responsive beta cells from pluripotent stem cells and human pancreatic progenitor cells.

In one aspect is provided a method of generating beta cells, comprising the steps of providing a starting cell population comprising at least one cell capable of differentiation; wherein the cell capable of differentiation is a pluripotent stem cell or a pancreatic progenitor cell expressing PDX1 and NKX6.1, wherein:

a. If the cell capable of differentiation is a pluripotent stem cell, the method comprises the steps of:
  i) Incubating said cell population in RPMI medium comprising Activin A and a glycogen synthase kinase (GSK3) inhibitor for a duration, thereby differentiating at least part of the cell population into definitive endoderm cells;
  ii) Incubating the cell population of i) in RPMI medium comprising B27–insulin, for a duration, thereby further differentiating the cell population into definitive endoderm cells;
  iii) Incubating the cell population of ii) in DMEM/F12 medium comprising B27+insulin and retinoic acid, for a duration, thereby differentiating at least part of the cell population into gut tube cells;
  iv) incubating the cell population of iii) in DMEM/F12 medium comprising B27+insulin and human FGF2, and optionally human Noggin, for a duration, thereby differentiating at least part of the cell population into posterior foregut cells;
  v) Incubating the cell population of iv) in DMEM/F12 medium comprising B27+insulin, ((2S,5S)-(E,E)-8-(5-(4-(Trifluoromethyl)phenyl)-2,4-pentadienoylamino)benzolactam) (TPB), and human Noggin for a duration, thereby differentiating at least part of the cell population into early pancreatic progenitor cells; and
  vi) Incubating the cell population of v) in DMEM/F12 medium comprising B27+insulin, Forskolin, Alk5 inhibitor, Nicotinamide, and human Noggin for a duration, thereby differentiating at least part of the cell population into mature pancreatic progenitor cells; and
  vii) Further incubating the cell population of vi) for an additional duration, thereby differentiating at least part of the cell population into beta cells;

or b. If the cell capable of differentiation is a pancreatic progenitor cell, the method comprises the steps of:
  viii) Incubating the starting cell population in DMEM/F12 medium comprising B27+insulin, Forskolin, Alk5 inhibitor, Nicotinamide, human Noggin and Rock inhibitor for a duration; and
  ix) Incubating the cell population obtained in step viii) in DMEM/F12 medium comprising B27+insulin, Forskolin, Alk5 inhibitor, Nicotinamide, human Noggin without Rock inhibitor for a duration.

In another aspect is provided a population of cells obtainable by the methods disclosed herein, for treatment of a metabolic disorder in an individual in need thereof.

In another aspect is provided a method of treatment of a metabolic disorder in an individual in need thereof, wherein the method comprises a step of providing a population of beta cells obtainable any of the methods disclosed herein and transplanting said population of beta cells into said individual.

The methods for obtaining glucose-responsive beta cells described herein present several advantages: they are faster and use fewer factors (such as differentiation factors) and are thus more reproducible than the protocols known in the art. They are versatile and can be used on different cell lines. The present methods are thus well suited for automation, and are thereby envisioned to significantly reduce manufacturing costs.

DESCRIPTION OF DRAWINGS

FIGS. 1A-1G. Analysis of in vitro differentiated PDXeG hESCs. FIG. 1A) Two differentiation protocols were used to obtain either pancreatic endoderm cells co-expressing PDX1 and NKX6.1 (protocol A (PEC)) or posterior foregut cells expressing PDX1 but lacking NKX6.1 (protocol B (PFG)). FIG. 1B) Schematic depicting the differentiation protocol referred to as "protocol A", generating PECs. FIG. 1C) FACS isolation of GFP$^+$ and GFP$^-$ fractions at day 17 in hESCs treated according to protocol A. FIG. 1D) Gene expression analysis of sorted GFP$^+$ and GFP$^-$ cells showed significant enrichment of PE markers (importantly PDX1 and NKX6.1) in the GFP$^+$ cells. The graphs depict mean expression±SEM (n=5) and represent the fold increase compared to control samples (GFP$^-$ cells) at day 17. The control sample was arbitrarily set to a value of one. p≤0.01, *p≤0.001, and ****p≤0.0001. FIG. 1E) Schematic depicting the differentiation protocol referred to as "protocol B", generating PFG cells. FIG. 1F) FACS isolation of GFP$^+$ and GFP$^-$ cells (from day 17) obtained by protocol B. FIG. 1G) Gene expression analysis of sorted GFP$^+$ and GFP$^-$ cells showed that whereas markers such as PDX1, CDH1, ONE-CUT1, and SOX9 were enriched in the GFP$^+$ cells, neither NKX6.1 nor MNX1 were significantly up-regulated in the GFP$^+$ cells. The graphs depict mean expression±SEM (n=2-4) and represent the fold increase compared to control samples (GFP$^-$ cells) at day 17. *p≤0.05, **p≤0.01. See also Figure S1 of Ameria et al. (2017).

FIGS. 2A-2E. Global gene expression analysis of in vitro derived PDX1+/NKX6.1+ PECs vs. PDX1$^+$/NKX6.1$^-$ cells. FIG. 2A) Heat-map displaying hierarchical clustering of genes differentially expressed in the PDX1$^+$/NKX6.1$^+$ (PEC, GFP$^+$) pancreatic progenitors generated using protocol A, PDX1$^+$/NKX6.1$^-$ (PFG, GFP$^+$) posterior foregut cells generated using protocol B, and PDX1$^-$ (GFP$^-$) cells from protocol A. FIG. 2B) Venn diagrams showing the distribution of genes up-regulated in PECs versus GFP$^-$ cells, PECs versus PFG cells, and PFG cells versus GFP$^-$ cells at day 17. FIG. 2C) Gene ontology (GO) analysis showing enrichment of genes in the PDX1$^+$/NKX6.1$^+$ pancreatic endoderm cells. Representative GO categories are shown and plotted against –log (p-value). FIG. 2D) Expression of common genes expressed in the PFG and PE was analyzed in the different sub-populations. FIG. 2E) Hierarchical clustering of the genes differentially expressed in the 3-comparison analysis depicted in A (average expression levels are shown). The bars indicate sub-clusters with relevant genes; nine different sub-clusters were created in total. Sub-cluster 3a shows genes enriched in the GFP$^-$ cell population, including the novel cell surface marker CD49d (ITGA4), whereas sub-cluster 5 displays genes enriched in the pancreatic endoderm cells (PEC cell fraction), also including the novel cell surface marker GP2. Sub-cluster 6 indicates genes enriched in PDX1$^+$ cells irrespective of NKX6.1 expression (PFG and PEC cells), such as CDH1 (ECAD), EPCAM, F3 (CD142) and the novel cell surface marker FOLR1. See also Table S1 of Ameri et al. (2017).

FIG. 3A) Flow cytometry analysis of the cell surface markers GP2, and ITGA4 performed on differentiated hESCs cultured on MEFs (day 17), confirmed that GP2 was highly expressed in the GFP$^+$ cells whereas ITGA4 was enriched in the GFP$^-$ cells. FIG. 3B) Gene expression analysis showed that PE markers were highly enriched in GP2$^+$/ITGA4$^-$ sorted cells. The data are shown as mean expression±SEM (n=3), *p≤0.05, p≤0.01, *p≤0.001. FIG. 3C) Flow cytometry analysis of GP2 and ITGA4 in genetically untagged HUES4 cells, cultured in a feeder-free system using protocol A depicted in FIG. 1. FIG. 3D) GP2$^+$ITGA4$^-$, ITGA4$^+$GP2$^-$, and GP2$^-$ITGA4$^-$ cells were sorted and the gene expression pattern was analyzed. PDX1, SOX9, MNX1, and NKX6.1 were significantly enriched in the GP2$^+$ITGA4$^-$ cell fractions. The remaining PDX1$^+$ cells in the GP2$^-$ITGA4$^-$ fraction express only low levels of NKX6.1, confirming that GP2 specifically enrich for PDX1$^+$/NKX6.1$^+$ cells. The data are shown as mean expression±SEM (n=5-6), *p≤0.05, p≤0.01, *p≤0.001, and ****p≤0.0001. FIG. 3E) Flow cytometry analysis of GP2 and ITGA4 expression in human fetal pancreas (9.1 WD) gated on non-hematopoietic and non-endothelial cells (CD45$^-$CD31$^-$). FIG. 3F) qPCR analysis of PDX1, and NKX6.1 expression in FACS sorted GP2$^+$ and ITGA4$^+$ cell populations, showed significant enrichment of PDX1 and NKX6.1 in the GP2$^+$ vs. the ITGA4$^+$ cells. Results are shown as mean expression±SD, presented in arbitrary units (AU) relative to expression of the control gene PPIA. *p=0.023 and **p=0.010. ND=Non-Detected. FIG. 3G) Flow cytometry analysis of PDX1 and NKX6.1 expression in GP2$^+$ and CD45$^+$/CD31$^+$ cells at 8.7 WD. 91% of the GP2$^+$/PDX1$^+$ cells co-expressed NKX6.1. CD45$^+$CD31$^+$ cells were used as a negative control for PDX1 and NKX6.1 expression. FACS plots are representative of 3 independent experiments. See also Figure S2 of Ameri et al. 2017.

FIGS. 4A-4G. Validation of GP2 using an independent and previously published differentiation protocol. FIG. 4A) Scheme for generation of hPSC-derived PECs according to a modified protocol by Rezania et. al, 2013. AA: Activin A, F7: FGF7, Nog: Noggin, DF12: DMEMF12, VitC: vitamin C. FIG. 4B) Characterization of GFP and GP2 expression by flow cytometry on differentiated PDXeG cells. FIG. 4C) qPCR analysis of the sorted populations: GP2$^-$GFP$^-$, GP2$^-$GPF$^+$, and GP2$^+$GFP$^+$ cells showed that NKX6.1 expression is significantly enriched in the GP2$^+$GFP$^+$ cell fraction in comparison to the GP2$^-$GFP$^+$ cell fraction. The data are shown as mean expression±SEM (n=3). FIG. 4D) Immunofluorescence stainings of the sorted cell populations confirmed significant enrichment of PDX1$^+$/NKX6.1$^+$ cells in the GP2$^+$/GFP$^+$ cells. Scale bars, 100 µm. FIG. 4E) Flow cytometry analysis of differentiated PDXeG cells on day 13. FIG. 4F) PDX1 and NKX6.1 expression in cultures at day 13 was analyzed by immunofluorescence. Scale bars, 100 µm. FIG. 4G) Percentage of PDX1$^+$/NKX6.1$^+$ quantified from day 13 cultures. See also Figure S3 of Ameri et al. 2017.

FIGS. 5A-5H. Differentiation of purified GP2$^+$/ITGA4$^-$ PECs into glucose responsive insulin expressing cells. FIG. 5A) Schematic illustrating differentiation of hESCs into PECs that are dissociated and stained with the cell surface markers ITGA4 and GP2. FIG. 5B) A table depicting the differentiation protocol to generate insulin expressing cells from PECs. Rocki is omitted when the protocol is applied to unsorted cultures. Rocki: Rock inhibitor, For: Forskolin, Alki: Alk5 inhibitor, Nog: Noggin, Nic: Nicotinamide, DF12: DMEM/F-12, B27: B27 Supplement. FIG. 5C) Flow cytometry analysis of differentiated PECs (from day 18) stained with GP2 and ITGA4. FIG. 5D) C-peptide staining of re-plated GP2$^{High}$ and GP2$^{Low}$ expressing cells. Scale bars, 100 µm. FIG. 5E) Percentage of CPEP$^+$ cells in the GP2$^{High}$ and GP2$^{Low}$ cells is shown. **p≤0.0001. FIG. 5F) Immunofluorescence analysis of FACS sorted GP2$^+$/ITGA4$^-$ pancreatic endoderm cells re-plated and differentiated to insulin expressing cells. Scale bars, 100 µm. FIG. 5G) Percentage of GLU$^+$ cells in the unsorted and GP2$^{High}$ cells is shown. p≤0.0001. FIG. 5H) The release of human C-peptide was measured in the differentiated GP2+/ITGA4− cells by a static glucose-stimulated insulin secretion assay (GSIS). Error bars represent mean expression±SEM (n=4), *p≤0.001, and ****p≤0.0001. See also FIGS. 8A-8H.

FIGS. 6A-6H. Validation of GP2 in the GMP graded cell line MShef-7. FIG. 6A) Time course analysis of INS and GLU expression in differentiated MShef-7 cells. The data are shown as mean expression±SEM (n=3). FIG. 6B) Flow cytometry analysis of differentiated PECs stained with GP2 and ITGA4. FIG. 6C) Co-staining of CPEP (white) and GLU (green) of unsorted cells. Scale bar, 100 μm D-E) Immunostainings of differentiated $GP2^{Low}$ cells (FIG. 6D) and $GP2^{High}$ cells (FIG. 6E) with CPEP (white), GLU (green), and NKX6.1 (red). Scale bars, 100 μm. FIG. 6F) Percentage of CPEP+ cells in unsorted, $GP2^{Low}$, $GP2^{High}$ cells. **p≤0.0001 FIG. 6G) Percentage of GLU+ cells in unsorted, $GP2^{Low}$, $GP^{High}$ cells. p≤0.0001. FIG. 6H) Static GSIS assay of differentiated $GP2^{High}$ cells showed a 2-fold change in CPEP response. Error bars represent mean expression±SEM p≤0.01. See also Figure S5 of Ameri et al. (2017).

FIGS. 7A-7M. CDKN1A and CDKN2A knockdown promote proliferation of hESC-derived PECs. FIGS. 7A-7B) Cell cycle analysis of differentiated hESCs at day 14 corresponding to early PECs. Cells from day 11 were transfected with CDKN1A siRNA and harvested 72 h later, stained with EDU and analyzed by flow cytometry (a representative analysis is shown). FIG. 7C) Summary of data depicted in A-B, where the corresponding ratio of CDKN1A/CTR siRNA for each cell cycle phase is shown. FIG. 7D) qPCR analysis of samples treated with scrambled and CDKN1A siRNA confirmed up-regulation of MKI67 expression 24 h after CDKN1A knockdown. The data are shown as mean expression±SEM, *p≤0.0001. FIG. 7E) Immunofluorescence analysis confirmed a significant increase of MKI67+ cells 72 h after knockdown of CDKN1A. Scale bars, 100 μm. FIG. 7F) Quantification of MKI67 expressing cells in the cultures showed there was a significant increase in the number of MKI67+ cells, p<0.0001. FIGS. 7G-7H) Cells from day 11 were transfected with CDKN2A siRNA and harvested 72 h later, stained with EDU and analyzed by flow cytometry (a representative analysis is shown). FIG. 7I) Summary of data depicted in FIGS. 7K-7L, where the corresponding ratio of CDKN2A/CTR siRNA for each cell cycle phase is shown. FIG. 7J) qPCR analysis showed no statistically significant up-regulation of MKI67 expression in the CDKN2A knocked down samples 24 h after transfection, error bars represent mean expression±SEM. However, immunofluorescence analysis showed a significant increase of MKI67+ cells (FIG. 7K) after 72 h of knockdown of CDKN2A. Scale bars, 100 μm. FIG. 7L) Quantification of MKI67 expressing cells in the cultures confirmed the significant increase in the number of MKI67+ cells, **p<0.0001. FIG. 7M) Schematic displaying PE formation during development. As the PE cells mature, CDKN1A (p21) and CDKN2A (p16) expression levels increase and MKI67 expression is downregulated (upper panel). Downregulation of p21 or p16 within early PECs prevents the decrease in proliferation during PE maturation (middle panel), whereas inhibition within late PE is unable to restore proliferation (lower panel). See also Figures S6 and S7 of Ameri et al. (2017).

FIGS. 8A-8H. Differentiation of hESCs into glucose responsive insulin expressing cells. FIG. 8A) Schematic illustrating the differentiation protocol (referred to as protocol C) for generating hPSC-derived insulin producing cells. AA: Activin A, CHIR: CHIR99021, RA: Retinoic acid, F2: FGF2, TPB: ((2S,5S)-(E,E)-8-(5-(4-(Trifluoromethyl) phenyl)-2,4-pentadienoylamino)benzolactam), Nog: Noggin, For: Forskolin, Alki: Alk5 inhibitor, Nic: Nicotinamide, RPMI: RPMI-1640 DF12: DMEM/F-12, B27: B27 Supplement. FIG. 8B) Immunofluorescence stainings of differentiated cells at the PE stage (day 18). Scale bar, 100 μm. FIG. 8C) Quantification of PDX1+/NKX6-1+ cells at day 18. FIG. 8D) GP2 and ITGA4 staining of PECs from day 18. FIG. 8E) Time course analysis of INS and GLU expression in differentiated HUES4 cells. The data are shown as mean expression±SEM (n=3). FIG. 8F) Immunofluorescence stainings of late stage cultures of differentiated hESCs. Scale bars, 100 μm. FIG. 8G) High magnification images of the immunofluorescence staining from FIG. 8F). Scale bars, 50 μm FIG. 8H) Released human C-peptide levels were measured by a static GSIS assay in differentiated hESCs at d32. Error bars represent±SEM. n=3), p<0.01, **p<0.0001.

DETAILED DESCRIPTION OF THE INVENTION

Figure 1A:
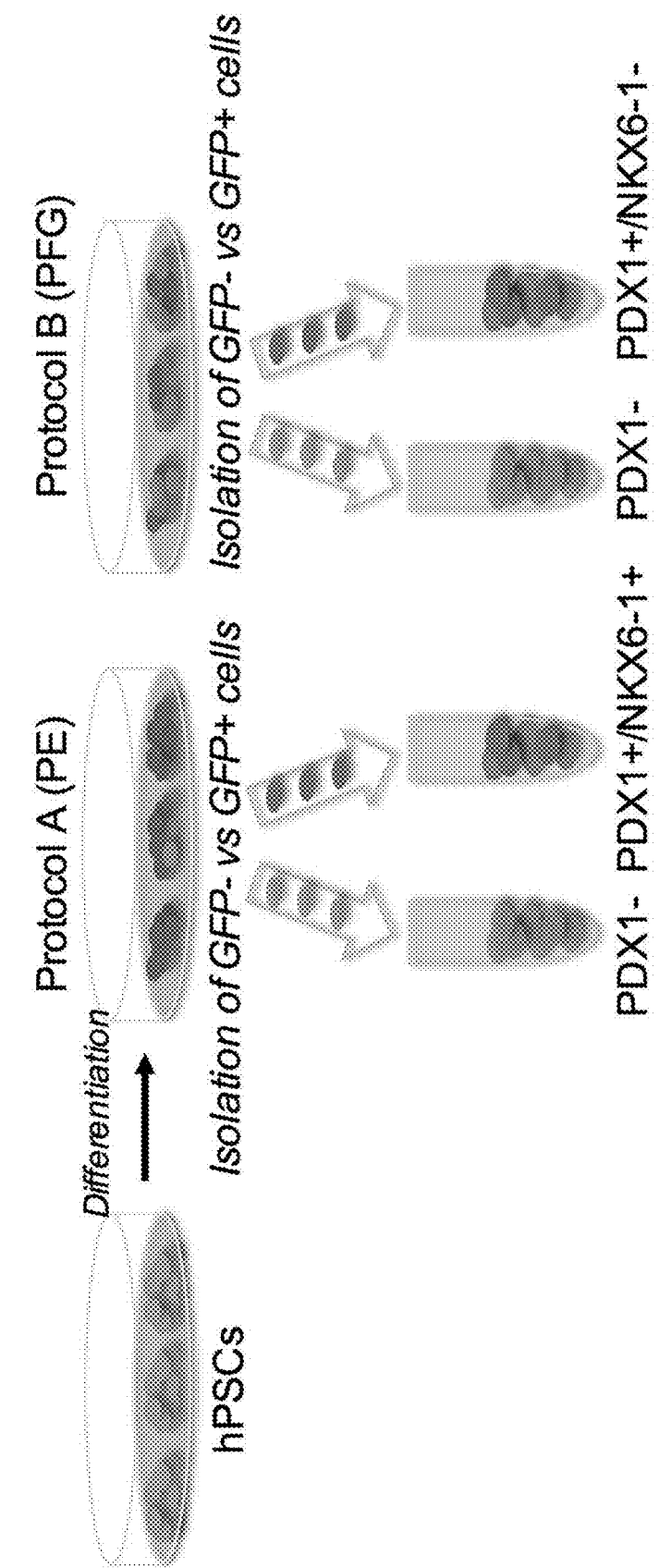

The present inventors have identified a method of generating beta cells.

The most recent success in generating hPSC-derived glucose responsive insulin-producing cells that share functional properties with normal beta cells (Pagliuca et al., 2014, Rezania et al., 2014), have made the implementation of a cell-based therapy for the treatment of type I diabetes a palpable reality. The therapeutic success of this approach will depend on the ability to upscale production of hPSC-derivatives. Estimates put the number of functional cells required for organ repair and disease recovery in the order of $10^9$ per patient (Pagliuca et al., 2014, Kempf et al., 2016). Thus, differentiation strategies will need to be adapted for mass production at an industrial scale. Currently, generation of glucose-responsive insulin-producing cells requires tedious and complicated multistep protocols, where undifferentiated hPSCs with tumorigenic propensity are used as the starting cell population. By establishing strategies where more mature cells are used for generating beta cells, the potential contamination with tumor-causing cells in the final cell preparation to be used for cell therapy could be prevented, and safer and more reproducible manufacturing procedures could be achieved. However, stage-specific surface markers that can be used to purify late stage cell populations during pancreatic differentiation are lacking.

During normal embryonic development the highly proliferative human and mouse pancreatic progenitors, recognized by their co-expression of the transcription factors Pancreatic duodenal homeobox 1 (PDX1) and NK6 homeobox 1 (NKX6.1), are responsible for the proper growth of the pancreatic epithelium and give rise to all the pancreatic cell types including exocrine, ductal, and endocrine cells. Consequently, pancreatic progenitor cells could serve as an ideal starting population for the generation of hormone producing endocrine cells such as the beta cells. Furthermore, previous publications support the notion that enrichment of pancreatic progenitors would reduce the risk of teratoma formation upon transplantation. Isolation of hPPCs could be obtained using tissue-specific cell surface molecules, and in fact markers for hPSC-derived pancreatic cell populations (CD142 for pancreatic progenitors and CD200/CD318 for endocrine cells) have been reported (Kelly 2011). However, the specificity of the pancreatic progenitor marker CD142 was questionable, as the populations enriched with this molecule were not exclusively composed of pancreatic progenitor cells as pointed out by the authors. Hence, the need for new and more specific markers to enrich for a progenitor population remains to be fulfilled.

Generation of tissue specific reporter cell lines could aid in the process of identifying pancreas-specific cell surface markers. Thus we established a PDX1-eGFP reporter cell line (PDXeG) by gene targeting in order to enable the isolation of pure PDX1+ pancreatic progenitor cells from hPSCs. By using the PDXeG reporter cell line as a genetic tool, we were able to isolate different subpopulations of PDX1+ cells and perform a genome wide expression analysis that allowed us to identify novel cell surface markers for isolation of hPPCs. Specifically, we identified three novel cell surface markers allowing us to separate true pancreatic progenitors from posterior foregut endoderm cells: glycoprotein 2 (zymogen granule membrane) (GP2) as a marker for isolation of PDX1+/NKX6.1+ hPPCs, Integrin Alpha-4 (ITGA4 or CD49d) as a negative selection marker labeling the PDX1− cell fraction, and finally a third marker, Folate receptor 1 (adult) (FOLR1) recognizing the PDX1+/NKX6.1− cells.

The specificity of these markers was demonstrated by using human fetal pancreas tissue, as described in patent application WO 2016/170069.

In one aspect is provided a method of generating beta cells, comprising the steps of providing a starting cell population comprising at least one cell capable of differentiation; wherein the cell capable of differentiation is a pluripotent stem cell or a pancreatic progenitor cell expressing PDX1 and NKX6.1, wherein:
  a. If the cell capable of differentiation is a pluripotent stem cell, the method comprises the steps of:
    i) Incubating said cell population in RPMI medium comprising Activin A and a glycogen synthase kinase (GSK3) inhibitor for a duration, thereby differentiating at least part of the cell population into definitive endoderm cells;
    ii) Incubating the cell population of i) in RPMI medium comprising B27−insulin, for a duration, thereby further differentiating the cell population into definitive endoderm cells;
    iii) Incubating the cell population of ii) in DMEM/F12 medium comprising B27+insulin and retinoic acid, for a duration, thereby differentiating at least part of the cell population into gut tube cells;
    iv) incubating the cell population of iii) in DMEM/F12 medium comprising B27+insulin and human FGF2, and optionally human Noggin, for a duration, thereby differentiating at least part of the cell population into posterior foregut cells;
    v) Incubating the cell population of iv) in DMEM/F12 medium comprising B27+insulin, ((2S,5S)-(E,E)-8-(5-(4-(Trifluoromethyl)phenyl)-2,4-pentadienoylamino)benzolactam) (TPB), and human Noggin for a duration, thereby differentiating at least part of the cell population into early pancreatic progenitor cells; and
    vi) Incubating the cell population of v) in DMEM/F12 medium comprising B27+insulin, Forskolin, Alk5 inhibitor, Nicotinamide, and human Noggin for a duration, thereby differentiating at least part of the cell population into mature pancreatic progenitor cells; and
    vii) Further incubating the cell population of vi) for an additional duration, thereby differentiating at least part of the cell population into beta cells; or
  b. If the cell capable of differentiation is a pancreatic progenitor cell, the method comprises the steps of:
    viii) Incubating the starting cell population in DMEM/F12 medium comprising B27+insulin, Forskolin, Alk5 inhibitor, Nicotinamide, human Noggin and Rock inhibitor for a duration; and
    ix) Incubating the cell population obtained in step viii) in DMEM/F12 medium comprising B27+insulin, Forskolin, Alk5 inhibitor, Nicotinamide, human Noggin without Rock inhibitor for a duration.

Also disclosed is a method of generating beta cells, comprising the steps of providing a starting cell population comprising at least one cell capable of differentiation; wherein the cell capable of differentiation is a pluripotent stem cell or a pancreatic progenitor cell expressing PDX1 and NKX6.1, wherein:
  a. If the cell capable of differentiation is a pluripotent stem cell, the method comprises the steps of:
    i) Incubating said cell population in RPMI medium comprising Activin A and a glycogen synthase kinase (GSK3) inhibitor for a duration of one day, thereby differentiating at least part of the cell population into definitive endoderm cells;
    ii) Incubating the cell population of i) in RPMI medium comprising B27−insulin, for a duration of between 3 and 6 days, thereby further differentiating the cell population into definitive endoderm cells;
    iii) Incubating the cell population of ii) in DMEM/F12 medium comprising B27+insulin and retinoic acid, for a duration of between 3 and 6 days, thereby differentiating at least part of the cell population into gut tube cells;
    iv) incubating the cell population of iii) in DMEM/F12 medium comprising B27+insulin and human FGF2, and optionally human Noggin, for a duration of between 3 and 6 days, thereby differentiating at least part of the cell population into posterior foregut cells;
    v) Incubating the cell population of iv) in DMEM/F12 medium comprising B27+insulin, ((2S,5S)-(E,E)-8-(5-(4-(Trifluoromethyl)phenyl)-2,4-pentadienoylamino)benzolactam) (TPB), and human Noggin for a duration of between 3 and 6 days, thereby differentiating at least part of the cell population into early pancreatic progenitor cells; and
    vi) Incubating the cell population of v) in DMEM/F12 medium comprising B27+insulin, Forskolin, Alk5 inhibitor, Nicotinamide, and human Noggin for a duration of between 3 and 6 days, thereby differentiating at least part of the cell population into mature pancreatic progenitor cells; and
    vii) Further incubating the cell population of vi) for an additional 7 to 23 days, thereby differentiating at least part of the cell population into beta cells; or
  b. If the cell capable of differentiation is a pancreatic progenitor cell, the method comprises the steps of:
    viii) Incubating the starting cell population in DMEM/F12 medium comprising B27+insulin, Forskolin, Alk5 inhibitor, Nicotinamide, human Noggin and Rock inhibitor for a duration of between 1 and 2 days; and
  Incubating the cell population obtained in step viii) in DMEM/F12 medium comprising B27+insulin, Forskolin, Alk5 inhibitor, Nicotinamide, human Noggin without Rock inhibitor for a duration of between 7 and 14 days.

Accordingly, a method of generating beta cells is disclosed, said method comprising the steps of providing a starting cell population comprising at least one cell capable of differentiation, wherein the cell capable of differentiation is a pluripotent stem cell, and further comprising the steps of:
- i) Incubating said cell population in RPMI medium comprising Activin A and a glycogen synthase kinase (GSK3) inhibitor for a duration of one day, thereby differentiating at least part of the cell population into definitive endoderm cells;
- ii) Incubating the cell population of i) in RPMI medium comprising B27−insulin, for a duration of between 3 and 6 days, thereby further differentiating the cell population into definitive endoderm cells;
- iii) Incubating the cell population of ii) in DMEM/F12 medium comprising B27+insulin and retinoic acid, for a duration of between 3 and 6 days, thereby differentiating at least part of the cell population into gut tube cells;
- iv) incubating the cell population of iii) in DMEM/F12 medium comprising B27+insulin and human FGF2, and optionally human Noggin, for a duration of between 3 and 6 days, thereby differentiating at least part of the cell population into posterior foregut cells;
- v) Incubating the cell population of iv) in DMEM/F12 medium comprising B27+insulin, ((2S,5S)-(E,E)-8-(5-(4-(Trifluoromethyl)phenyl)-2,4-pentadienoylamino) benzolactam) (TPB), and human Noggin for a duration of between 3 and 6 days, thereby differentiating at least part of the cell population into early pancreatic progenitor cells; and
- vi) Incubating the cell population of v) in DMEM/F12 medium comprising B27+insulin, Forskolin, Alk5 inhibitor, Nicotinamide, and human Noggin for a duration of between 3 and 6 days, thereby differentiating at least part of the cell population into mature pancreatic progenitor cells; and
- vii) Further incubating the cell population of vi) for an additional 7 to 23 days, thereby differentiating at least part of the cell population into beta cells.

Also disclosed is a method of generating beta cells, comprising the steps of providing a starting cell population comprising a pancreatic progenitor cell expressing PDX1 and NKX6.1, wherein the method further comprises the steps of:
- viii) Incubating the starting cell population in DMEM/F12 medium comprising B27+insulin, Forskolin, Alk5 inhibitor, Nicotinamide, human Noggin and Rock inhibitor for a duration of between 1 and 2 days; and
- ix) Incubating the cell population obtained in step viii) in DMEM/F12 medium comprising B27+insulin, Forskolin, Alk5 inhibitor, Nicotinamide, human Noggin without Rock inhibitor for a duration of between 7 and 14 days.

In some embodiments, the method of generating beta cells comprises the steps of providing a starting cell population comprising at least one cell capable of differentiation, wherein the cell capable of differentiation is a pluripotent stem cell, and further comprising the steps of:
- i) Incubating said cell population in RPMI medium comprising Activin A and a glycogen synthase kinase (GSK3) inhibitor for a duration, thereby differentiating at least part of the cell population into definitive endoderm cells;
- ii) Incubating the cell population of i) in RPMI medium comprising B27−insulin, for a duration, thereby further differentiating the cell population into definitive endoderm cells;
- iii) Incubating the cell population of ii) in DMEM/F12 medium comprising B27+insulin and retinoic acid, for a duration, thereby differentiating at least part of the cell population into gut tube cells;
- iv) incubating the cell population of iii) in DMEM/F12 medium comprising B27+insulin and human FGF2, and optionally human Noggin, for a duration, thereby differentiating at least part of the cell population into posterior foregut cells;
- v) Incubating the cell population of iv) in DMEM/F12 medium comprising B27+insulin, ((2S,5S)-(E,E)-8-(5-(4-(Trifluoromethyl)phenyl)-2,4-pentadienoylamino) benzolactam) (TPB), and human Noggin for a duration, thereby differentiating at least part of the cell population into early pancreatic progenitor cells, and enriching the obtained cell population for cells expressing PDX1 and NKX6.1 as described herein, thereby obtaining an enriched cell population;
- vi) Incubating the enriched cell population of step v) in DMEM/F12 medium comprising B27+insulin, Forskolin, Alk5 inhibitor, Nicotinamide, human Noggin and Rock inhibitor for a duration; and
- vii) Incubating the cell population obtained in step vi) in DMEM/F12 medium comprising B27+insulin, Forskolin, Alk5 inhibitor, Nicotinamide, human Noggin without Rock inhibitor for a duration.

In some embodiments, the method of generating beta cells comprises the steps of providing a starting cell population comprising at least one cell capable of differentiation, wherein the cell capable of differentiation is a pluripotent stem cell, and further comprising the steps of:
- i) Incubating said cell population in RPMI medium comprising Activin A and a glycogen synthase kinase (GSK3) inhibitor for a duration of one day, thereby differentiating at least part of the cell population into definitive endoderm cells;
- ii) Incubating the cell population of i) in RPMI medium comprising B27−insulin, for a duration of between 3 and 6 days, thereby further differentiating the cell population into definitive endoderm cells;
- iii) Incubating the cell population of ii) in DMEM/F12 medium comprising B27+insulin and retinoic acid, for a duration of between 3 and 6 days, thereby differentiating at least part of the cell population into gut tube cells;
- iv) incubating the cell population of iii) in DMEM/F12 medium comprising B27+insulin and human FGF2, and optionally human Noggin, for a duration of between 3 and 6 days, thereby differentiating at least part of the cell population into posterior foregut cells;
- v) Incubating the cell population of iv) in DMEM/F12 medium comprising B27+insulin, ((2S,5S)-(E,E)-8-(5-(4-(Trifluoromethyl)phenyl)-2,4-pentadienoylamino) benzolactam) (TPB), and human Noggin for a duration of between 3 and 6 days, thereby differentiating at least part of the cell population into early pancreatic progenitor cells, and enriching the obtained cell population for cells expressing PDX1 and NKX6.1 as described herein, thereby obtaining an enriched cell population;
- vi) Incubating the enriched cell population of step v) in DMEM/F12 medium comprising B27+insulin, Forskolin, Alk5 inhibitor, Nicotinamide, human Noggin and Rock inhibitor for a duration of between 1 and 2 days; and
- vii) Incubating the cell population obtained in step vi) in DMEM/F12 medium comprising B27+insulin, Forskolin, Alk5 inhibitor, Nicotinamide, human Noggin without Rock inhibitor for a duration of between 7 and 14 days.

In other embodiments, the method of generating beta cells comprises the steps of providing a starting cell population comprising at least one cell capable of differentiation, wherein the cell capable of differentiation is a pluripotent stem cell, and further comprising the steps of:

i) Incubating said cell population in RPMI medium comprising Activin A and a glycogen synthase kinase (GSK3) inhibitor for a duration, thereby differentiating at least part of the cell population into definitive endoderm cells;

ii) Incubating the cell population of i) in RPMI medium comprising B27−insulin, for a duration, thereby further differentiating the cell population into definitive endoderm cells;

iii) Incubating the cell population of ii) in DMEM/F12 medium comprising B27+insulin and retinoic acid, for a duration, thereby differentiating at least part of the cell population into gut tube cells;

iv) incubating the cell population of iii) in DMEM/F12 medium comprising B27+insulin and human FGF2, and optionally human Noggin, for a duration, thereby differentiating at least part of the cell population into posterior foregut cells;

v) Incubating the cell population of iv) in DMEM/F12 medium comprising B27+insulin, ((2S,5S)-(E,E)-8-(5-(4-(Trifluoromethyl)phenyl)-2,4-pentadienoylamino) benzolactam) (TPB), and human Noggin for a duration, thereby differentiating at least part of the cell population into early pancreatic progenitor cells, and further incubating the early pancreatic progenitor cell population in DMEM/F12 medium comprising B27+insulin, Forskolin, Alk5 inhibitor, Nicotinamide, and human Noggin for a duration, thereby differentiating at least part of the cell population into mature pancreatic progenitor cells, and enriching the obtained cell population for cells expressing PDX1 and NKX6.1 as described herein, thereby obtaining an enriched cell population;

vi) Incubating the enriched cell population of step v) in DMEM/F12 medium comprising B27+insulin, Forskolin, Alk5 inhibitor, Nicotinamide, human Noggin and Rock inhibitor for a duration; and vii) Incubating the cell population obtained in step vi) in DMEM/F12 medium comprising B27+insulin, Forskolin, Alk5 inhibitor, Nicotinamide, human Noggin without Rock inhibitor for a duration.

In other embodiments, the method of generating beta cells comprises the steps of providing a starting cell population comprising at least one cell capable of differentiation, wherein the cell capable of differentiation is a pluripotent stem cell, and further comprising the steps of:

i) Incubating said cell population in RPMI medium comprising Activin A and a glycogen synthase kinase (GSK3) inhibitor for a duration of one day, thereby differentiating at least part of the cell population into definitive endoderm cells;

ii) Incubating the cell population of i) in RPMI medium comprising B27−insulin, for a duration of between 3 and 6 days, thereby further differentiating the cell population into definitive endoderm cells;

iii) Incubating the cell population of ii) in DMEM/F12 medium comprising B27+insulin and retinoic acid, for a duration of between 3 and 6 days, thereby differentiating at least part of the cell population into gut tube cells;

iv) incubating the cell population of iii) in DMEM/F12 medium comprising B27+insulin and human FGF2, and optionally human Noggin, for a duration of between 3 and 6 days, thereby differentiating at least part of the cell population into posterior foregut cells;

v) Incubating the cell population of iv) in DMEM/F12 medium comprising B27+insulin, ((2S,5S)-(E,E)-8-(5-(4-(Trifluoromethyl)phenyl)-2,4-pentadienoylamino) benzolactam) (TPB), and human Noggin for a duration of between 3 and 6 days, thereby differentiating at least part of the cell population into early pancreatic progenitor cells, and further incubating the early pancreatic progenitor cell population in DMEM/F12 medium comprising B27+insulin, Forskolin, Alk5 inhibitor, Nicotinamide, and human Noggin for a duration of between 3 and 6 days, thereby differentiating at least part of the cell population into mature pancreatic progenitor cells, and enriching the obtained cell population for cells expressing PDX1 and NKX6.1 as described herein, thereby obtaining an enriched cell population;

vi) Incubating the enriched cell population of step v) in DMEM/F12 medium comprising B27+insulin, Forskolin, Alk5 inhibitor, Nicotinamide, human Noggin and Rock inhibitor for a duration of between 1 and 2 days; and vii) Incubating the cell population obtained in step vi) in DMEM/F12 medium comprising B27+insulin, Forskolin, Alk5 inhibitor, Nicotinamide, human Noggin without Rock inhibitor for a duration of between 7 and 14 days.

In another aspect is provided a population of cells obtainable by the methods disclosed herein, for treatment of a metabolic disorder in an individual in need thereof.

In another aspect is provided a method of treatment of a metabolic disorder in an individual in need thereof, wherein the method comprises a step of providing a population of beta cells obtainable any of the methods disclosed herein and transplanting said population of beta cells into said individual.

Definitions

Antibody. The term 'antibody' describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulins. The terms antibody or antibodies as used herein is used in the broadest sense and covers intact antibodies, chimeric, humanized, fully human and single chain antibodies, as well as binding fragments of antibodies, such as Fab, F(ab')$_2$, Fv fragments or scFv fragments, as well as multimeric forms such as dimeric IgA molecules or pentavalent IgM.

Antigen. An antigen is a molecule comprising at least one epitope. The antigen may for example be a polypeptide, polysaccharide, protein, lipoprotein or glycoprotein.

Definitive endoderm. As used herein, "definitive endoderm" or "DE" refers to a multipotent cell that can differentiate into cells of the gut tube or organs derived from the gut tube. In accordance with certain embodiments, the definitive endoderm cells and cells derived therefrom are mammalian cells, and in a preferred embodiment, the definitive endoderm cells are human cells. In some embodiments, definitive endoderm cells express or fail to significantly express certain markers. In some embodiments, one or more markers selected from SOX17, CXCR4, MIXLI, GAT A4, FOXA2, GSC, FGF 17, VWF, CALCR, FOXQI, CMKORI, CER and CRIPI are expressed in definitive endoderm cells. In other embodiments, one or more markers selected from OCT4, HNF4A, alpha-fetoprotein (AFP), Thrombomodulin (TM), SPARC and SOX7 are not significantly expressed in definitive endoderm cells. Definitive endoderm cells do not express PDX-1.

Differentiable or differentiated cell. As used herein, the phrase, "differentiable cell" or "differentiated cell" or "hES-derived cell" can refer to pluripotent, multipotent, oligopotent or even unipotent cells, as defined in detail below. In certain embodiments, the differentiable cells are pluripotent differentiable cells. In more specific embodiments, the pluripotent differentiable cells are selected from the group consisting of embryonic stem cells, ICM/epiblast cells, primitive ectoderm cells, primordial germ cells, and teratocarcinoma cells. In one particular embodiment, the differentiable cells are mammalian embryonic stem cells. In a more particular embodiment, the differentiable cells are human embryonic stem cells. Certain embodiments also contemplate differentiable cells from any source within an animal, provided the cells are differentiable as defined herein. For example, differentiable cells can be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

Differentiation. As used herein, the term "differentiation" refers to the production of a cell type that is more differentiated than the cell type from which it is derived. The term therefore encompasses cell types that are partially and terminally differentiated. Similarly, "produced from hESCs," "derived from hESCs," "differentiated from hESCs," "hES derived cell" and equivalent expressions refer to the production of a differentiated cell type from hESCs in vitro and in vivo.

Embryonic. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

Expression level. As used herein, the term "expression level" can refer to the level of transcript (mRNA) or to the level of protein for a particular gene or protein, respectively. Expression levels can thus be determined by methods known in the art, by determining transcription level or protein level. Transcription levels can be measured by quantifying the amount of transcript by methods such as, but not limited to, Northern blot, RT-PCR or microarray-based methods. Protein levels can be measured by methods such as, but not limited to, Western blot and immunostaining.

Human embryonic stem cells. The human embryonic stem cells are derived from the undifferentiated inner cell mass of the human embryo. These cells are pluripotent and are able to differentiate into all derivatives of the three primary germ layers namely: ectoderm, endoderm and mesoderm (Thomson et al., 1998). As used herein, the term "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in literature often denoted as human embryonic stem (hES) cells (see, e.g., Thomson et al. (1998), Heins et. al. (2004), as well as induced pluripotent stem cells (see, e.g. Yu et al. (2007) Science 318:5858; Takahashi et al. (2007) Cell 131 (5):861). The various methods and other embodiments described herein may require or utilise hPS cells (hPSCs) from a variety of sources. For example, hPS cells suitable for use may be obtained from developing embryos. Additionally or alternatively, suitable hPS cells may be obtained from established cell lines and/or human induced pluripotent stem (hiPS) cells by methods, which do not require the destruction of embryos (Chung et al. 2008).

As used herein "hiPS cells" refers to human induced pluripotent stem cells. As used herein, the term "blastocyst-derived stem cell" is denoted BS cell, and the human form is termed "hBS cells". In literature the cells are often referred to as embryonic stem cells, and more specifically human embryonic stem cells (hESCs). The pluripotent stem cells used in the present invention can thus be embryonic stem cells prepared from blastocysts, as described in e.g. WO 03/055992 and WO 2007/042225, or be commercially available hBS cells or cell lines. However, it is further envisaged that any human pluripotent stem cell can be used in the present invention, including differentiated adult cells which are reprogrammed to pluripotent stem cells by e.g. the treating adult cells with certain transcription factors, such as OCT4, SOX2, NANOG, and LIN28 as disclosed in Yu, et al., 2007, Takahashi et al. 2007 and Yu et al 2009.

Inactivation: The term 'inactivation' is herein used in connection with inactivation of the function of a given protein in a cell and refers to manipulations of the cell in order to obtain a loss of function. Inactivation may be achieved as known in the art, e.g. by using an inhibitor capable of inhibiting the function of the protein. Inactivation can also be achieved by mutation or deletion of the gene encoding the protein. Silencing, for example by using siRNAs, can also be used to achieve inactivation, as known to the person skilled in the art. Inactivation may be transient or permanent. Inactivation may also be reversible or irreversible. For example, incubation of a cell population with an inhibitor will typically result in transient inactivation for as long as the inhibitor is effective or present. Removing the inhibitor from the environment will generally result in alleviation of the inactivation. Likewise, siRNAs will typically only have a silencing effect for as long as they are expressed or present. Deletion or mutation of a gene on the other hand will typically result in permanent inactivation, although the person skilled in the art will know how to reverse the effects of deletion or mutation, for example by gene editing methods.

Induced pluripotent stem cell. Induced pluripotent stem cells (or iPSCs) can be derived directly from adult cells by reprogramming (Takashashi et al., 2006). iPSCs can be induced by proteins and are then termed protein-induced pluripotent stem cells (piPSCs).

Ligand. As used herein, "ligand" refers to a moiety or binding partner that specifically binds or cross-reacts to the marker or target or receptor or membrane protein on the cell or to the soluble analyte in a sample or solution. The target on the cell includes but is not limited to a marker. Examples of such ligands include, but are not limited to, an antibody that binds a cellular antigen, an antibody that binds a soluble antigen, an antigen that binds an antibody already bound to the cellular or soluble antigen; a lectin that binds to a soluble carbohydrate or to a carbohydrate moiety which is a part of a glycoprotein or glycolipid; or functional fragments of such antibodies and antigens that are capable of binding; a nucleic acid sequence sufficiently complementary to a target nucleic acid sequence of the cellular target or soluble analyte to bind the target or analyte sequence, a nucleic acid sequence sufficiently complementary to a ligand nucleic acid sequence already bound to the cellular marker or target or soluble analyte, or a chemical or proteinaceous compound, such as biotin or avidin. Ligands can be soluble or can be immobilized on the capture medium (i.e., synthetically covalently linked to a bead), as indicated by the assay format, e.g., antibody affinity chromatography. As defined herein, ligands include, but are not limited to, various agents that detect and react with one or more specific cellular markers or targets or soluble analytes.

Marker. As used herein, "marker", "epitope", "target", "receptor" or equivalents thereof can refer to any molecule that can be observed or detected. For example, a marker can include, but is not limited to, a nucleic acid, such as a transcript of a specific gene, a polypeptide product of a gene, such as a membrane protein, a non-gene product polypeptide, a glycoprotein, a carbohydrate, a glycolipid, a lipid, a lipoprotein or a small molecule (for example, molecules having a molecular weight of less than 10,000 amu). A "cell surface marker" is a marker present at the cell surface.

Multipotent cell. As used herein, "multipotent" or "multipotent cell" refers to a cell type that can give rise to a limited number of other particular cell types. Multipotent cells are committed to one or more embryonic cell fates, and thus, in contrast to pluripotent stem cells, cannot give rise to each of the three germ layer lineages as well as extraembryonic cells.

Naïve stem cell and primed stem cell. Naïve stem cells have the potential to develop into any kind of cell, unlike primed stem cells, which are able to differentiate into several types of cells but are already predetermined to some extent. Naïve stem cells have been known to exist in mice but human naïve stem cells have only been described recently (Takashima et al., 2014). Naïve stem cells can self-renew continuously without ERK signalling, are phenotypically stable, and are karyotypically intact. They differentiate in vitro and form teratomas in vivo. Metabolism is reprogrammed with activation of mitochondrial respiration as in ESC. The pluripotent state of human cells can be reset by short-term expression of two components, NANOG and KLF2, as described in Takashima et al., 2014. Naive PSCs share many properties with the inner cell mass of the blastocyst, while the primed PSCs resemble epiblast cells of a more advanced, pregastrulating stage embryo. In the mouse, the naive state is represented by embryonic stem cells (mESCs) and the primed state by epiblast stem cells (EpiSCs). In humans, blastocyst derived ESCs have been regarded until recently as the human equivalent of mESCs. However, without being bound by theory, based on multiple characteristics such as flat morphology, dependence on growth factors, or X-chromosome inactivation, hESCs (and human induced pluripotent stem cell (hiPSCs)) are closer to mouse EpiSCs than to mESCs and, as such, more likely correspond to the primed rather than the naive state of pluripotency (Tesar et al. 2007; Stadtfeld and Hochedlinger 2010).

Naturally occurring antibody. The term 'naturally occurring antibody' refers to heterotetrameric glycoproteins capable of recognising and binding an antigen and comprising two identical heavy (H) chains and two identical light (L) chains inter-connected by disulfide bonds. Each heavy chain comprises a heavy chain variable region (abbreviated herein as $V_H$) and a heavy chain constant region (abbreviated herein as $C_H$). Each light chain comprises a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Antibodies may comprise several identical heterotetramers.

Pancreatic progenitor cell (PPC) or multipotent pancreatic progenitor cell. A progenitor cell is a cell that is committed to differentiate into a certain type of cell. Pancreatic progenitor cells are thus multipotent and can differentiate and give rise to all cell types of the pancreas. The term 'pancreatic progenitor cell' or 'true pancreatic progenitor' refers herein to a cell, which is capable of differentiating into all pancreatic lineages, including acinar, duct and endocrine, such as insulin-producing cells. The term is herein used interchangeably with the term pancreatic endoderm cells (PECs).

Partially mature cell. As used herein, "partially mature cells" refer to cells that exhibit at least one characteristic of the phenotype, such as morphology or protein expression, of a mature cell from the same organ or tissue. Some embodiments contemplate using differentiable cells from any animal capable of generating differentiable cells, e.g., pancreatic type cells such as beta cells. The animals from which the differentiable cells are harvested can be vertebrate or invertebrate, mammalian or non-mammalian, human or non-human. Examples of animal sources include, but are not limited to, primates, rodents, canines, felines, equines, bovines and porcines.

Pluripotent stem cell. By "pluripotent" is meant that the cell can give rise to each of the three germ layer lineages. Pluripotent stem cells, however, may not be capable of producing an entire organism. In certain embodiments, the pluripotent stem cells used as starting material are stem cells, including human embryonic stem cells. Pluripotent stem cells can be derived by explanting cells from embryos at different stages of development. PSCs (pluripotent stem cells) can be classified into two distinct states, naive and primed, depending on which stage they are during embryonic development.

Stem cell. A stem cell is an undifferentiated cell that can differentiate into specialized cells and can divide to produce more stem cells. The term stem cell comprises embryonic stem cells, adult stem cells, naïve stem cells as well as induced pluripotent stem cells. Stem cells are defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Totipotent stem cell: The term refers to a cell having the potential to give rise to any and all types of human cells such as all three germ layer lineages and extraembryonic lineages. It can give rise to an entire functional organism.

In the present disclosure, any gene or protein name can refer to the gene or the protein in any species. For example, PDX1 or Pdx1 are used interchangeably and can refer to either murine Pdx1 or human PDX1 or to Pdx1 in another species.

In the present disclosure, a "−" sign after a gene or protein name means that the gene or protein is not expressed, while a "+" sign after a gene or protein name means that the gene or protein is expressed. Thus PDX1− or PDX1− cells are cells that do not express PDX1, while PDX1+ or PDX1+ cells are cells that express PDX1.

Generation of Beta Cells

The present methods allow generation of glucose-responsive beta cells from a starting cell population comprising at least one cell capable of differentiation. In one embodiment, the cell capable of differentiation is a pluripotent stem cell, such as a pluripotent stem cell, for example a human pluripotent stem cell. In another embodiment, the cell capable of differentiation is a pancreatic progenitor cell.

The present methods provide a protocol for differentiating a cell population comprising pluripotent stem cells into beta cells. This can be done by following the following steps:
i) Incubating said cell population in RPMI medium comprising Activin A and a glycogen synthase kinase (GSK3) inhibitor for a duration of one day, thereby differentiating at least part of the cell population into definitive endoderm cells;
ii) Incubating the cell population of i) in RPMI medium comprising B27−insulin, for a duration of between 3 and 6 days, thereby further differentiating the cell population into definitive endoderm cells;
iii) Incubating the cell population of ii) in DMEM/F12 medium comprising B27+insulin and retinoic acid, for a duration of between 3 and 6 days, thereby differentiating at least part of the cell population into gut tube cells;
iv) incubating the cell population of iii) in DMEM/F12 medium comprising B27+insulin and human FGF2, and optionally human Noggin, for a duration of between 3 and 6 days, thereby differentiating at least part of the cell population into posterior foregut cells;
v) Incubating the cell population of iv) in DMEM/F12 medium comprising B27+insulin, ((2S,5S)-(E,E)-8-(5-(4-(Trifluoromethyl)phenyl)-2,4-pentadienoylamino) benzolactam) (TPB), and human Noggin for a duration of between 3 and 6 days, thereby differentiating at least part of the cell population into early pancreatic progenitor cells; and
vi) Incubating the cell population of v) in DMEM/F12 medium comprising B27+insulin, Forskolin, Alk5 inhibitor, Nicotinamide, and human Noggin for a duration of between 3 and 6 days, thereby differentiating at least part of the cell population into mature pancreatic progenitor cells; and
vii) Further incubating the cell population of vi) for an additional 7 to 23 days, thereby differentiating at least part of the cell population into beta cells.

In all embodiments, the medium used in step vii) is preferably the same as the medium used in step vi). For all steps, the medium may be refreshed every day or every second day, as is known to the skilled person.

In some embodiments of the invention, the cell population obtained in step v) may be enriched for cells expressing PDX1 and NKX6.1 to obtain an enriched cell population. In this case, steps vi) and vii) above may be replaced by steps viii) and ix) below:
viii) Incubating the enriched cell population in DMEM/F12 medium comprising B27+insulin, Forskolin, Alk5 inhibitor, Nicotinamide, human Noggin and Rock inhibitor for a duration of between 1 and 2 days; and
ix) Incubating the cell population obtained in step viii) in DMEM/F12 medium comprising B27+insulin, Forskolin, Alk5 inhibitor, Nicotinamide, human Noggin without Rock inhibitor for a duration of between 7 and 14 days.

In some embodiments of the invention, the cell population obtained in step vi) may be enriched for cells expressing PDX1 and NKX6.1 to obtain an enriched cell population. In this case, step vii) above may be replaced by steps viii) and ix) below:
viii) Incubating the enriched cell population in DMEM/F12 medium comprising B27+insulin, Forskolin, Alk5 inhibitor, Nicotinamide, human Noggin and Rock inhibitor for a duration of between 1 and 2 days; and
ix) Incubating the cell population obtained in step viii) in DMEM/F12 medium comprising B27+insulin, Forskolin, Alk5 inhibitor, Nicotinamide, human Noggin without Rock inhibitor for a duration of between 7 and 14 days.

In other embodiments, the starting cell population comprising at least one cell capable of differentiation is a population comprising pancreatic progenitor cells expressing PDX1 and NKX6.1. In such embodiments, the method of differentiating these cells into beta cells comprises the steps of:
viii) Incubating the starting cell population in DMEM/F12 medium comprising B27+insulin, Forskolin, Alk5 inhibitor, Nicotinamide, human Noggin and Rock inhibitor for a duration of between 1 and 2 days; and
ix) Incubating the cell population obtained in step viii) in DMEM/F12 medium comprising B27+insulin, Forskolin, Alk5 inhibitor, Nicotinamide, human Noggin without Rock inhibitor for a duration of between 7 and 14 days.

The starting population of cells may be as described herein below. In some embodiments, the starting cell population comprises pancreatic progenitor cells and has been enriched for cells expressing PDX1 and NKX6.1 as described herein below, for example by taking advantage of cell surface markers. The present methods can then be applied to such "sorted" cell populations to further differentiate them. In some embodiments, the starting cell population has not been enriched for cells expressing PDX1 and NKX6.1.

In one embodiment, the starting cell population comprises pancreatic progenitor cells and has been enriched for cells expressing PDX1 and NKX6.1 by being contacted with a first ligand which binds to a first marker specific for PDX1− cells and selecting the cells that do not bind to said first ligand from said cell population.

In another embodiment, the starting cell population comprises pancreatic progenitor cells and has been enriched for cells expressing PDX1 and NKX6.1 by being contacted with a second ligand which binds to a second marker specific for PDX1+ cells and selecting the cells that bind to said second ligand from the cells that do not bind to said second ligand, thereby enriching the cell population for PDX1+ cells.

In another embodiment, the starting cell population comprises pancreatic progenitor cells and has been enriched for cells expressing PDX1 and NKX6.1 by being contacted with a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells.

In another embodiment, the starting cell population comprises pancreatic progenitor cells and has been enriched for cells expressing PDX1 and NKX6.1 by being contacted with, in either order:
 a) a first ligand which binds to a first marker specific for PDX1− cells and selecting the cells that do not bind to said first ligand from said cell population; and
 b) a second ligand which binds to a second marker specific for PDX1+ cells and selecting the cells that bind to said second ligand from the cells that do not bind to said second ligand, thereby enriching the cell population for PDX1+ cells.

In another embodiment, the starting cell population comprises pancreatic progenitor cells and has been enriched for cells expressing PDX1 and NKX6.1 by being contacted with, in either order:
 a) a first ligand which binds to a first marker specific for PDX1− cells and selecting the cells that do not bind to said first ligand from said cell population; and
 b) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells.

In another embodiment, the starting cell population comprises pancreatic progenitor cells and has been enriched for cells expressing PDX1 and NKX6.1 by being contacted with, in either order:
 a) a second ligand which binds to a second marker specific for PDX1+ cells and selecting the cells that bind to said second ligand from the cells that do not bind to said second ligand, thereby enriching the cell population for PDX1+ cells; and
 b) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells.

In another embodiment, the starting cell population comprises pancreatic progenitor cells and has been enriched for cells expressing PDX1 and NKX6.1 by being contacted with, in either order:
 a) a first ligand which binds to a first marker specific for PDX1− cells and selecting the cells that do not bind to said first ligand from said cell population; and
 b) a second ligand which binds to a second marker specific for PDX1+ cells and selecting the cells that bind to said second ligand from the cells that do not bind to said second ligand, thereby enriching the cell population for PDX1+ cells; and
 c) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells.

For any of the above embodiments, CD49d/ITGA4 is a preferred first ligand. For any of the above embodiments, FOLR1, CDH1/ECAD, F3/CD142, PDX1, FOXA2, EPCAM, HES1 and GATA4 are preferred second ligands. FOLR1 is even more preferred. For any of the above embodiments, GP2, SCN9A, MPZ, NAALADL2, KCNIP1, CALB1, SOX9, NKX6.2 and NKX6.1 are preferred third ligands. More preferred are GP2, SCN9A, MPZ, NAALADL2, KCNIP1 and CALB1. Even more preferred is GP2.

In some embodiments, the starting cell population comprises pancreatic progenitor cells, and may have been obtained as described herein by providing a cell population comprising pluripotent stem cells and performing steps i) to v) above. In other embodiments, the starting cell population comprises pancreatic progenitor cells, and may have been obtained as described herein by providing a cell population comprising pluripotent stem cells and performing steps i) to vi) above.

Starting Cell Population

In a first step, a cell population (the starting cell population) comprising at least one cell capable of differentiation is provided. In some embodiments, the cell capable of differentiation is a pancreatic progenitor cell expressing PDX1 and NKX6.1.

In some embodiments, the starting cell population comprises at least 5% pancreatic progenitor cells, such as at least 10% pancreatic progenitor cells, such as at least 15% pancreatic progenitor cells, such as at least 20% pancreatic progenitor cells, such as at least 25% pancreatic progenitor cells, such as at least 30% pancreatic progenitor cells, such as at least 35% pancreatic progenitor cells, such as at least 40% pancreatic progenitor cells, such as at least 45% pancreatic progenitor cells, such as at least 50% pancreatic progenitor cells, such as at least 55% pancreatic progenitor cells, such as at least 60% pancreatic progenitor cells, such as at least 65 pancreatic progenitor cells, such as at least 70% pancreatic progenitor cells, such as at least 75% pancreatic progenitor cells, such as at least 80% pancreatic progenitor cells, such as at least 85% pancreatic progenitor cells, such as at least 90% pancreatic progenitor cells, such as at least 95% pancreatic progenitor cells.

In order to determine the fraction of progenitor cells comprised in a cell population, for example in the starting population, methods known in the art can be employed, such as, but not limited to, immunostaining or flow cytometry methods.

Without being bound by theory, the percentage of pancreatic progenitor cells in the starting cell population can be estimated by the expression of GP2. Thus in some embodiments, the starting cell population comprises at least 5% cells expressing GP2, such as at least 10% cells expressing GP2, such as at least 15% cells expressing GP2, such as at least 20% cells expressing GP2, such as at least 25% cells expressing GP2, such as at least 30% cells expressing GP2, such as at least 35% cells expressing GP2, such as at least 40% cells expressing GP2, such as at least 45% cells expressing GP2, such as at least 50% cells expressing GP2, such as at least 55% cells expressing GP2, such as at least 60% cells expressing GP2, such as at least 65% cells expressing GP2, such as at least 70% cells expressing GP2, such as at least 75% cells expressing GP2, such as at least 80% cells expressing GP2, such as at least 85% cells expressing GP2, such as at least 90% pancreatic progenitor cells, such as at least 95% pancreatic progenitor cells. GP2 expression can be determined by methods known in the art, such as immunostaining methods, flow cytometry methods or quantitative measurements of transcription levels.

Likewise, without being bound by theory, the percentage of PDX1+NKX6.1+ cells in the starting cell population can be estimated by the expression of GP2. Thus in some embodiments, the starting cell population comprises at least 5% cells expressing GP2, such as at least 10% cells expressing GP2, such as at least 15% cells expressing GP2, such as at least 20% cells expressing GP2, such as at least 25% cells expressing GP2, such as at least 30% cells expressing GP2, such as at least 35% cells expressing GP2, such as at least 40% cells expressing GP2, such as at least 45% cells expressing GP2, such as at least 50% cells expressing GP2, such as at least 55% cells expressing GP2, such as at least 60% cells expressing GP2, such as at least 65% cells expressing GP2, such as at least 70% cells expressing GP2, such as at least 75% cells expressing GP2, such as at least 80% cells expressing GP2, such as at least 85% cells expressing GP2, such as at least 90% pancreatic progenitor cells, such as at least 95% pancreatic progenitor cells. GP2 expression can be determined by methods known in the art, such as immunostaining methods, flow cytometry methods or quantitative measurements of transcription levels.

In some embodiments, the cell population may be derived or isolated from an individual, such as, but not limited to, a mammal, for example a human.

In some embodiments, the cells capable of differentiation are pluripotent stem cells, for example human pluripotent stem cells (hPSCs). hPSCs include human induced pluripotent stem cells (hiPSCs), human embryonic stem cells (hESCs) and naïve human stem cells (NhSCs).

In one embodiment, the starting cell population is obtained from a pancreas, including a foetal pancreas or an adult pancreas. In one aspect, the pancreas is from a mammal, such as a human.

In another embodiment, the starting cell population is a somatic cell population. In some embodiments, the starting cell population comprises at least one pancreatic progenitor cell expressing PDX1 and NKX6.1 and is obtained from a somatic cell population. In a further aspect of the invention, the somatic cell population has been induced to de-differentiate into an embryonic-like stem cell (ESC, e.g. a pluripotent stem cell, or hESCs for human ESCs). Such dedifferentiated cells are also termed induced pluripotent stem cells (IPSCs, or hIPSCs for human IPSCs).

In yet another embodiment, the starting cell population is ESCs or hESCs. In one embodiment, the starting cell population is obtained from ESCs or hESCs. In some embodiments, the starting cell population is a population of pluripotent stem cells such as ESC like-cells.

In some embodiments, a cell population comprising at least one pancreatic progenitor cell may be obtained by methods known in the art, before steps viii) and ix) as described herein are performed. For example, differentiation can be induced in embryoid bodies and/or in monolayer cell cultures or a combination thereof.

In one aspect of the invention, the starting cell population is of mammalian origin. In one aspect of the invention, the starting cell population is of human origin.

In one aspect of the invention, the starting cell population is obtained from one or more donated pancreases. The methods described herein are not dependent on the age of the donated pancreas. Accordingly, pancreatic material isolated from donors ranging in age from embryos to adults can be used.

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissociated into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, lipase preparations and other enzymes are contemplated for use with the methods disclosed herein.

Isolated source material can be further processed to enrich for one or more desired cell populations prior to performing the present methods. In some aspects unfractionated pancreatic tissue, once dissociated for culture, can also be used directly in the culture methods of the invention without further separation. However, unfractionated pancreatic tissue, once dissociated for culture, can also be used directly in the culture methods of the invention without further separation, and will yield the intermediate cell population. In one embodiment the isolated pancreatic cellular material is purified by centrifugation through a density gradient (e. g., Nycodenz, Ficoll, or Percoll). The mixture of cells harvested from the donor source will typically be heterogeneous and thus contain alpha cells, beta cells, delta cells, ductal cells, acinar cells, facultative progenitor cells, and other pancreatic cell types.

A typical purification procedure results in the separation of the isolated cellular material into a number of layers or interfaces. Typically, two interfaces are formed. The upper interface is islet-enriched and typically contains 10 to 100% islet cells in suspension.

The second interface is typically a mixed population of cells containing islets, acinar, and ductal cells. The bottom layer is the pellet, which is formed at the bottom of the gradient. This layer typically contains primarily acinar cells, some entrapped islets, and some ductal cells. Ductal tree components can be collected separately for further manipulation.

The cellular constituency of the fractions selected for further manipulation will vary depending on which fraction of the gradient is selected and the final results of each isolation. When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In one embodiment, intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped islet cells, respectively, can also be used in culture. While both layers contain cells capable of giving rise to the enriched pancreatic progenitor cell population described herein, each layer may have particular advantages for use with the disclosed methods.

In one embodiment, the starting cell population is a population of stem cells. In one embodiment, the starting cell population is a population of stem cells that is obtained without the destruction of an embryo. Methods for obtaining stem cells without destroying embryos are known in the art (Chung et al., 2008).

A protocol for obtaining pancreatic cells from stem cells is exemplified by, but not limited to, the protocols described in D'Amour, K. A. et al. (2006); Jiang, J. et al. (2007); and Kroon, E. et al. (2008), Rezania et al (2012, 2014), Felicia W. Pagliuca et al (2014). Pancreatic progenitor cells obtained using such protocols can be further differentiated to beta cells using the methods disclosed herein, in particular steps viii) and ix).

A protocol for obtaining pancreatic cells from somatic cells or somatic cells induced to dedifferentiate into pluripotent stem cells such as ES like-cells is exemplified by, but not limited to, the protocols described in Aoi, T. et al. (2008), Jiang, J. et al. (2007), Takahashi, K. et al. (2007),Takahashi and Yamanaka (2006), and Wernig, M. et al. (2007). Other protocols have been described by D'Amour, K. A. et al. (2006) or Kroon, E. et al. (2008). Pancreatic progenitor cells obtained using such protocols can be further differentiated to beta cells using the methods disclosed herein, in particular steps viii) and ix).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In some aspects "differentiate" or "differentiation" as used herein refers to a process where cells progress from an immature state to a less immature state. In another aspect "differentiate" or "differentiation" as used herein refers to a process where cells progress from an undifferentiated state to a differentiated state or from an immature state to a mature state. For example, undifferentiated pancreatic cells may be able to proliferate and express characteristics markers, like PDX1. Early undifferentiated embryonic pancreatic cells may be able to proliferate and express characteristics markers, like PDX1. In one embodiment mature or differentiated pancreatic cells do not proliferate and secrete high levels of pancreatic endocrine hormones. In some embodiments mature or differentiated pancreatic cells do not proliferate and secrete high levels of pancreatic endocrine hormones or digestive enzymes. In one embodiment, e.g., mature beta cells secrete insulin at high levels. In some embodiments e.g., mature beta cells secrete insulin at high levels in response to glucose. Changes in cell interaction and maturation occur as cells lose markers of undifferentiated cells or gain markers of differentiated cells. In one embodiment loss or gain of a single marker can indicate that a cell has "matured or differentiated". In some embodiments loss or gain of a single marker can indicate that a cell has "matured or fully differentiated". The term "differentiation factors" refers to a compound added to pancreatic cells to enhance their differentiation to mature endocrine cells also containing insulin producing beta cells. Exemplary differentiation factors include hepatocyte growth factor, keratinocyte growth factor, exendin-4, basic fibroblast growth factor, insulin-like growth factor-I, nerve growth factor, epidermal growth factor platelet-derived growth factor, and glucagon-like-peptide 1. In one embodiment, differentiation of the cells comprises culturing the cells in a medium comprising one or more differentiation factors.

In some embodiments, the cell population comprising at least one pancreatic progenitor cell is analysed to identify whether at least one of the cells of the starting population expresses markers characteristic of the pancreatic endocrine lineage and selected from the group consisting of NGN3, NEUROD, ISL1, PDX1, NKX6.1, NKX2.2, MAFA, MAFB, ARX, BRN4, PAX4 and PAX6, GLUT2, INS, GCG, SST, pancreatic poly-peptide (PP). In some embodiments markers characteristic of the pancreatic endocrine lineage are selected from the group consisting of PDX1 and NKX6.1. In one embodiment, a pancreatic endocrine cell is capable of expressing at least one of the following hormones: insulin, glucagon, somatostatin, and PP. In some embodiments, a pancreatic endocrine cell is capable of expressing at least one of the following hormones: insulin, glucagon, somatostatin, PP and ghrelin. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one embodiment, the pancreatic endocrine cell is a cell expressing markers characteristic of the beta cell lineage. A cell expressing markers characteristic of the beta cell lineage expresses PDX1 and may further express at least one of the following transcription factors: NGN3, NKX2-2, NKX6.1, NEUROD, ISL1, FOXA2, MAFA, PAX4, and PAX6. In one embodiment, a cell expressing markers characteristic of the beta cell lineage is a beta cell. In one embodiment, the pancreatic endocrine cell is a cell expressing the marker NKX6.1. In another aspect of the invention, the pancreatic endocrine cell is a cell expressing the marker PDX1. In a further aspect of the invention, the pancreatic endocrine cell is a cell expressing the markers NKX6.1 and PDX1.

PDX1 is homeodomain transcription factor implicated in pancreas development. Pax-4 is a beta cell specific factor and Pax-6 is a pancreatic islet cell (specific) transcription factor; both are implicated in islet development. Hnf-3 beta (also known as FoxA2) belongs to the hepatic nuclear factor family of transcription factors, which is characterized by a highly conserved DNA binding domain and two short carboxy-terminal domains. NeuroD is basic helix-loop-helix (bHLH) transcription factor implicated in neurogenesis. Ngn3 is a member of the neurogenin family of basic loop-helix-loop transcription factors. NKX2-2 and NKX6.1 as used herein are members of the Nkx transcription factor family. Islet-1 or ISL-1 is a member of the LIM/homeodomain family of transcription factors, and is expressed in the developing pancreas. MAFA is a transcription factor expressed in the pancreas, and controls the expression of genes involved in insulin biosynthesis and secretion. NKX6.1 and PDX1 are co-expressed with PTF1a in the early pancreatic multipotent cell that can develop into all cell types found in the adult pancreas (e.g., acinar, ductal, and endocrine cells). Within this cell population cells that also transiently express NGN3 are found. Once a cell expresses or has expressed NGN3 it will be part of the endocrine lineage, giving rise to endocrine cells (one type being the insulin producing beta cell) that will later form the Islets of Langerhans. In the absence of NGN3 no endocrine cells form during pancreas development. As development progress NKX6.1 and PDX1 are co-expressed in the more central domain of the pancreas, which now becomes devoid of PTF1a expression and the NKX6.1 and PDX1 positive cells can no longer give rise to acinar cells. Within this NKX6.1 and PDX1 positive cell population a significant number of cells transiently co-express NGN3, marking them for the endocrine lineage like earlier in development.

In one embodiment, the cells comprised in the starting cell population are derived from cells capable of differentiation. In a specific embodiment, the cells capable of differentiation are human pluripotent stem cells. In some embodiments, the cells capable of differentiation are selected from the group consisting of human iPS cells (hIPSCs), human ES cells (hESCs) and naive human stem cells (NhSCs).

The cells capable of differentiation may be derived from cells isolated from an individual.

CDKN1a, also dubbed P21, and CDKN2a, also P16, are cell cycle specific genes. CDKN1a (cyclin-dependent kinase inhibitor 1 or CDK-interacting protein 1), is a cyclin-dependent kinase inhibitor that inhibits the complexes of CDK2 and CDK1. CDKN1 thus functions as a regulator of cell cycle progression at G1 and S phase. CDKN2a (cyclin-dependent kinase inhibitor 2A, multiple tumor suppressor 1) is a tumor suppressor protein. It plays an important role in cell cycle regulation by decelerating cells progression from G1 phase to S phase, and therefore acts as a tumor suppressor that is implicated in the prevention of cancers.

The inventors have surprisingly found that inactivation of CDKN1a or CDKN2a in the starting cell population facilitates entry of the cell population in a replicating state corresponding to the G2/M phase, in particular when the starting cell population is PDX1 expressing pancreatic progenitor cells. Inactivation of CDKN1a or CDKN2a in the starting cell population may also facilitate entry of the cell population in the S phase. Thus inactivation of CDKN1a or CDKN2a may be useful for obtaining mature beta cells from expanded pancreatic progenitor cells.

In some embodiments, expression of CDKN1a and/or CDKN2a in the starting cell population is inactivated. In some embodiments, the starting cell population is a population of pancreatic progenitor cells expressing PDX1. The starting cell population may also be any of the populations described above. The skilled person knows how to inactivate expression of CDKN1a and/or CDKN2a. This may be done for instance by mutating or deleting the corresponding genes, by known gene editing methods. Alternatively, silencing means may be employed such as siRNA in order to prevent expression of CDKN1a and/or CDKN2a. Alternatively, inhibitors preventing correct function of CDKN1a and/or CDKN2a may be used.

Pancreatic Progenitor Cells

In the pancreas several different types of pancreatic cells may be found. The pancreatic cells include for example multi-potent pancreatic progenitor cells, ductal/acinar progenitor cells, fully differentiated acinar/exocrine cells, ductal/endocrine progenitor cells, endocrine progenitor cells, early endocrine cells, and/or fully differentiated endocrine cells. Pancreatic endoderm progenitor cells expressing PDX1 and NKX6.1 have the capacity to differentiate into acinar cells, ductal cells or endocrine cells. The term 'pancreatic progenitor cell' or 'true pancreatic progenitor' refers herein to a cell, which is capable of differentiating into all pancreatic lineages, including acinar, duct and endocrine, such as insulin-producing cells.

Pancreatic early endocrine cells are cells, which have initiated expression of one of the pancreatic endocrine hormones (insulin, glucagon, somatostatin and pancreatic polypeptide) but do not share all the characteristics of fully mature pancreatic endocrine cells found in the Islet of Langerhans in the adult pancreas. These cells may be endocrine cells which have turned off Ngn3 but do not share all the characteristics of fully differentiated pancreatic endocrine cells found in the Islet of Langerhans in the adult pancreas, such as responsiveness to glucose, and are positive for one of the pancreatic endocrine hormones (insulin, glucagon, somatostatin, pancreatic polypeptide, and ghrelin).

Pancreatic endocrine cells, or pancreatic hormone-producing cells, are cells capable of expressing at least one of the following hormones: insulin, glucagon, somatostatin, pancreatic polypeptide and ghrelin.

"Pancreatic fully differentiated endocrine cells" (also termed "fully differentiated endocrine cells", "pancreatic mature endocrine cells", "pancreatic endocrine cells" or "pancreatic adult endocrine cells") are cells, which share all the characteristics of fully differentiated pancreatic endocrine cells found in the Islet of Langerhans in the adult pancreas.

The methods disclosed herein can be used to differentiate pancreatic progenitor cells at the pancreatic endoderm stage into pancreatic hormone-producing cells such as β-cells and/or insulin-producing cells. The insulin-producing cells may be responsive to glucose.

Cell Population Enriched in Pancreatic Progenitor Cells

In embodiments where the starting cell population comprises pancreatic progenitor, the starting cell population may have been enriched by:

providing a cell population comprising at least one pancreatic progenitor cell, wherein the pancreatic progenitor cell expresses PDX1 and NKX6.1; and exposing said cell population to:
  a) a first ligand which binds to a first marker specific for PDX1− cells and selecting the cells that do not bind to said first ligand from said cell population, thereby enriching the cell population for PDX1+ cells;
  and/or
  b) a second ligand which binds to a second marker specific for PDX1+ cells and selecting the cells that bind to said second ligand from the cells that do not bind to said second ligand, thereby enriching the cell population for PDX1+ cells;
  and/or
  c) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;

thereby obtaining a starting cell population enriched for pancreatic progenitor cells.

The cell population thus enriched can then be differentiated into beta cells by a method comprising:
  viii) Incubating the enriched cell population in DMEM/F12 medium comprising B27+insulin, Forskolin, Alk5 inhibitor, Nicotinamide, human Noggin and Rock inhibitor for a duration of between 1 and 2 days; and
  ix) Incubating the cell population obtained in step viii) in DMEM/F12 medium comprising B27+insulin, Forskolin, Alk5 inhibitor, Nicotinamide, human Noggin without Rock inhibitor for a duration of between 7 and 14 days.

In some embodiments, the starting cell population comprising at least one pancreatic progenitor cell expressing PDX1 and NKX6.1, is enriched for cells expressing PDX1 and NKX6.1 by taking advantage of surface markers and ligands thereto, as described herein below. Such methods are also described in detail in application WO 2016/170069.

Markers and Ligands

PDX1 (Pancreatic and duodenal homeobox 1), also known as insulin promoter factor 1, is a transcription factor necessary for pancreatic development and β-cell maturation. In embryonic development, PDX1 is expressed by a population of cells in the posterior foregut region of the definitive endoderm, and PDX1+ epithelial cells give rise to the developing pancreatic buds, and eventually, the whole of the pancreas—its exocrine, endocrine, and ductal cell populations. Pdx1 is also necessary for β-cell maturation: developing β-cells co-express PDX1, NKX6.1, and insulin, a process that results in the silencing of MafB and the expression of MafA, a necessary switch in maturation of β-cells. PDX1+ pancreatic progenitor cells also co-express Hlxb9, Hnf6, Ptf1a and NKX6.1 (homeobox protein Nkx-6.1), and these progenitor cells form the initial pancreatic buds, which may further proliferate. Pancreatic endocrine cells express PDX1 and NKX6.1 (PDX1+ NKX6.1+ cells).

The inventors have previously identified surface markers specific for cells that do not express PDX1 (PDX1− cells), while other markers were identified as being specific for cells that express PDX1 (PDX1+), and yet others as being specific for cells that express PDX1 and NKX6.1. Molecules capable of binding to such markers shall herein be referred to as "ligands" and can be used to isolate true pancreatic progenitor cells.

Accordingly, a starting cell population may be enriched for pancreatic progenitor cell by a method comprising the steps of providing a cell population comprising at least one pancreatic progenitor cell, wherein the pancreatic progenitor cell expresses PDX1 and NKX6.1; and exposing said cell population to:
  a) a first ligand which binds to a first marker specific for PDX1− cells and selecting the cells that do not bind to said first ligand from said cell population, thereby enriching the cell population for PDX1+ cells;
  and/or
  b) a second ligand which binds to a second marker specific for PDX1+ cells and selecting the cells that bind to said second ligand from the cells that do not bind to said second ligand, thereby enriching the cell population for PDX1+ cells;
  and/or
  c) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;

thereby obtaining a cell population enriched for pancreatic progenitor cells.

It will be understood that a cell population can be exposed to any of the first and/or second and/or third ligand in simultaneous steps or in subsequent steps and that the steps can be performed in any order. In some embodiments, the cell population is exposed only to only one of the first, second or third ligand. In other embodiments, the cell population is exposed to two or three of the first, second or third ligand. In some embodiments, the cell population is exposed to the first, the second and the third ligand simultaneously. In some embodiments, the cell population is exposed to the first ligand and to the second ligand in separate steps. In other embodiments, the cell population is exposed to the first ligand and to the third ligand in separate steps. In other embodiments, the cell population is exposed to the first ligand and to the second or third ligand simultaneously. In other embodiments, the cell population is exposed to the first ligand and in a separate step is exposed to the second and third ligand simultaneously. In other embodiments, the cell population is exposed simultaneously to the first and second or third ligand. In other embodiments, the cell population is exposed simultaneously to the first and second ligand, and is exposed to the third ligand in a separate step. In other embodiments, the cell population is exposed simultaneously to the first and third ligand, and is exposed to the second ligand in a separate step.

Cell populations enriched for cells expressing PDX1 and NKX6.1 using any of these methods can be differentiated into beta cells by:
  viii) Incubating the enriched cell population in DMEM/F12 medium comprising B27+insulin, Forskolin, Alk5 inhibitor, Nicotinamide, human Noggin and Rock inhibitor for a duration of between 1 and 2 days; and
  ix) Incubating the cell population obtained in step viii) in DMEM/F12 medium comprising B27+insulin, Forskolin, Alk5 inhibitor, Nicotinamide, human Noggin without Rock inhibitor for a duration of between 7 and 14 days.

Ligands

After a cell population comprising at least one pancreatic progenitor cell has been provided, said population may be exposed to a first ligand which binds to a first marker specific for PDX1− cells and the cells that do not bind to said first ligand are selected. This negative separation results in a cell population enriched for PDX1+ cells. The cell population is exposed to a second ligand which binds a marker specific for PDX1+ cells and/or to a third ligand binding a third marker specific for PDX1+ NKX6.1+ cells and the cells binding to the second and/or third ligand are selected. It will be understood that exposure to each of the first and second and/or third ligand can be performed simultaneously or in separate steps.

Accordingly, in one embodiment, the cell population is exposed to a first ligand which binds to a first marker specific for PDX1− cells. After the cells that do not bind to the first ligand have been selected, the cell population, now enriched for PDX1+ cells, is exposed to a second ligand which binds a marker specific for PDX1+ cells and/or to a third ligand binding a third marker specific for PDX1+ NKX6.1+ cells and the cells binding to the second and/or third ligand are selected.

In another embodiment, the cell population is exposed to the first ligand, to the second ligand and/or to the third ligand simultaneously, and the cells that do not bind the first ligand but that bind to the second and/or third ligand are selected.

Each of the ligands disclosed herein is a moiety that specifically binds or cross-reacts to a marker, i.e. a marker specific for PDX1+ cells, PDX1− cells or PDX1+ NKX6.1+ cells. The term ligand or ligands' will be used as a generic term to refer to any of the first, second or third ligand.

Such ligands and markers are described in more detail in application WO 2016/170069, in particular in the section entitled "Ligands".

First Ligand

The present method for enriching a cell population for pancreatic progenitor cell comprises the steps of:
providing a cell population comprising at least one pancreatic progenitor cell, wherein the pancreatic progenitor cell expresses PDX1 and NKX6.1; and
exposing said cell population to:
  a) a first ligand which binds to a first marker specific for PDX1− cells and selecting the cells that do not bind to said first ligand from said cell population, thereby enriching the cell population for PDX1+ cells;
and/or
  b) a second ligand which binds to a second marker specific for PDX1+ cells and selecting the cells that bind to said second ligand from the cells that do not bind to said second ligand, thereby enriching the cell population for PDX1+ cells;
and/or
  c) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
thereby obtaining a cell population enriched for pancreatic progenitor cells.

Accordingly, after providing a starting cell population comprising at least one pancreatic progenitor cell, wherein the pancreatic progenitor cell expresses PDX1 and NKX6.1, the cell population may be exposed to a first ligand which binds a first marker specific for PDX1− cells and the cells that do not bind to said first ligand may be selected, thereby enriching for PDX1-expressing (PDX1+) cells.

The first ligand can be a ligand as described above. In some embodiments, the first ligand is a ligand capable of recognising and binding a cell surface marker. In some embodiments, the cell surface marker is CD49d. In some embodiments, the first ligand is a monoclonal or polyclonal antibody or fragment thereof directed against CD49d. The first ligand may be conjugated to a label, for example in order to facilitate selection of the cells that do not bind to the first ligand, as detailed above.

Selection of the cells that do not bind to the first ligand may be performed by methods known in the art such as flow cytometry. Accordingly, in some embodiments, expression of the first marker may be detected by flow cytometry.

Second Ligand

The method may further comprise the step of exposing the starting population (or the cells that do not express PDX1 after selection with a first ligand as described above) to a second ligand which binds to a second marker specific for PDX1+ cells and selecting the cells that bind to said second ligand from the cells that do not bind to said second ligand, thereby obtaining a cell population enriched for PDX1+ cells. As a result, a population enriched for pancreatic progenitor is obtained. The enriched population may in particular be enriched for posterior foregut PDX1+ cells.

The second ligand can be a ligand as described above. In some embodiments, the second ligand is a ligand capable of recognising and binding a cell surface marker. In some embodiments, the second ligand can recognise and bind to a second target selected from the group consisting of FOLR1, CDH1/ECAD, F3/CD142, PDX1, FOXA2, EPCAM, HES1, and GATA4. In some embodiments, the second ligand is a monoclonal or polyclonal antibody or fragment thereof directed against a second target selected from the group consisting of FOLR1, CDH1/ECAD, F3/CD142, PDX1, FOXA2, EPCAM, HES1, and GATA4. The second ligand may be conjugated to a label, for example in order to facilitate selection of the cells that bind to the second ligand, as detailed above. In a preferred embodiment, the second ligand is capable of recognising and binding to FOLR1.

Selection of the cells that bind to the second ligand may be performed by methods known in the art such as flow cytometry. Accordingly, in some embodiments, expression of the second marker may be detected by flow cytometry.

Exposure of the cell population to the second ligand may occur at the same time as exposure to the first ligand and optionally to the third ligand, or it may occur in a separate step.

Third Ligand

The method may comprise the step of exposing the cell population to a third ligand which binds to a third marker specific for PDX1+ NKX6.1+ cells and the cells that bind to said third ligand are selected, in order to obtain a cell population enriched for pancreatic progenitor cells expressing both PDX1 and NKX6.1. Exposure to the third ligand may be performed instead of exposure to the second ligand. In some embodiments, the cell population is exposed to the first and third ligand, where the exposure to the ligands can occur simultaneously or in separate steps. In other embodiments, the cell population is exposed to the first, the second and the third ligand, where the exposure to the ligands can occur simultaneously or in separate steps. As a result, a population enriched for pancreatic progenitor cells is obtained.

The third ligand can be a ligand as described above. In some embodiments, the third ligand is a ligand capable of recognising and binding a cell surface marker. In some embodiments, the third ligand can recognise and bind to a third target, where the third target is selected from the group consisting of GP2, SCN9A, MPZ, NAALADL2, KCNIP1, CALB1, SOX9, NKX6.2, and NKX6.1. In a preferred embodiment, the third target is GP2. In some embodiments, the third ligand is a monoclonal or polyclonal antibody or fragment thereof directed against a third target selected from the group consisting of GP2, SCN9A, MPZ, NAALADL2, KCNIP1, CALB1, SOX9, NKX6.2 and NKX6.1. In a preferred embodiment, the third ligand is a monoclonal or polyclonal antibody or fragment thereof directed against GP2. The third ligand may be conjugated to a label, for example in order to facilitate selection of the cells that bind to the third ligand, as detailed above.

Selection of the cells that bind to the third ligand may be performed by methods known in the art such as flow cytometry. Accordingly, in some embodiments, expression of the third marker may be detected by flow cytometry.

Accordingly, in some embodiments, a cell population, which may be obtained by steps i) to v) or by steps i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to:
  a) a first ligand which binds to a first marker specific for PDX1− cells and selecting the cells that do not bind to said first ligand from said cell population, thereby enriching the cell population for PDX1+ cells;
and/or
  b) a second ligand which binds to a second marker specific for PDX1+ cells and selecting the cells that bind to said second ligand from the cells that do not bind to said second ligand, thereby enriching the cell population for PDX1+ cells;
and/or
  c) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
wherein
  the first ligand recognises and binds to CD49d,
  the second ligand recognises and binds to a second marker selected from the group consisting of FOLR1, CDH1/ECAD, F3/CD142, PDX1, FOXA2, EPCAM, HES1, and GATA4, and
  the third ligand recognises and binds to a third marker selected from the group consisting of GP2, SCN9A, MPZ, NAALADL2, KCNIP1, CALB1, SOX9, NKX6.2 and NKX6.1,
thereby obtaining a cell population enriched for pancreatic progenitor cells.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to:
  a) a first ligand which binds to a first marker specific for PDX1− cells and selecting the cells that do not bind to said first ligand from said cell population, thereby enriching the cell population for PDX1+ cells;
and
  b) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
wherein
  the first ligand recognises and binds to CD49d, and
  the third ligand recognises and binds to a third marker selected from the group consisting of GP2, SCN9A, MPZ, NAALADL2, KCNIP1, CALB1, SOX9, NKX6.2 and NKX6.1,
thereby obtaining a cell population enriched for pancreatic progenitor cells.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to:
  a) a first ligand which binds to a first marker specific for PDX1− cells and selecting the cells that do not bind to said first ligand from said cell population, thereby enriching the cell population for PDX1+ cells;
and
  b) a second ligand which binds to a second marker specific for PDX1+ cells and selecting the cells that bind to said second ligand from the cells that do not bind to said second ligand, thereby enriching the cell population for PDX1+ cells;
wherein
  the first ligand recognises and binds to CD49d, and
  the second ligand recognises and binds to a second marker selected from the group consisting of FOLR1, CDH1/ECAD, F3/CD142, PDX1, FOXA2, EPCAM, HES1, and GATA4,
thereby obtaining a cell population enriched for pancreatic progenitor cells.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to:
  a) a first ligand which binds to a first marker specific for PDX1− cells and selecting the cells that do not bind to said first ligand from said cell population, thereby enriching the cell population for PDX1+ cells;
  b) a second ligand which binds to a second marker specific for PDX1+ cells and selecting the cells that bind to said second ligand from the cells that do not bind to said second ligand, thereby enriching the cell population for PDX1+ cells;
and
  c) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
wherein
  the first ligand recognises and binds to CD49d,
  the second ligand recognises and binds to FOLR1, and
  the third ligand recognises and binds to GP2, thereby obtaining a cell population enriched for pancreatic progenitor cells.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to:
a) a first ligand which binds to a first marker specific for PDX1− cells and selecting the cells that do not bind to said first ligand from said cell population, thereby enriching the cell population for PDX1+ cells; and
b) a second ligand which binds to a second marker specific for PDX1+ cells and selecting the cells that bind to said second ligand from the cells that do not bind to said second ligand, thereby enriching the cell population for PDX1+ cells;
wherein
the first ligand recognises and binds to CD49d,
the second ligand recognises and binds to FOLR1,
thereby obtaining a cell population enriched for pancreatic progenitor cells.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
Exposing said cell population to a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
wherein
the third ligand recognises and binds to a marker selected from the group consisting of SCN9A, MPZ, NAALADL2, KCNIP1, CALB1, SOX9, NKX6.2 and NKX6.1,
thereby obtaining a cell population enriched for pancreatic progenitor cells.

In a preferred embodiment, the marker is SCN9A, MPZ, NAALADL2, KCNIP1, GP2 or CALB1. In a specific embodiment, the marker is GP2.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
thereby obtaining a cell population enriched for pancreatic progenitor cells.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
wherein the third ligand recognises and binds to GP2,
thereby obtaining a cell population enriched for pancreatic progenitor cells.

In some embodiments, a cell population, which may be obtained by steps i) to v) or i) to vi) described herein, is enriched for pancreatic progenitor cells by:
providing a cell population comprising at least one pancreatic progenitor cell, wherein the pancreatic progenitor cell expresses PDX1 and NKX6.1; and
exposing said cell population to:
a) a second ligand which binds to a second marker specific for PDX1+ cells and selecting the cells that bind to said second ligand from the cells that do not bind to said second ligand, thereby enriching the cell population for PDX1+ cells;
and
b) a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells;
wherein
the second ligand recognises and binds to FOLR1,
the third ligand recognises and binds to GP2,
thereby obtaining a cell population enriched for pancreatic progenitor cells.

It will be understood that methods for generating hormone producing beta cells such as insulin-producing beta cells include sorting GP2 positive cells isolated by flow cytometry or other similar methods and differentiating said sorted cells further using the methods described herein.

The present methods allow differentiation of a population of at least part of a starting cell population comprising at least one pancreatic progenitor cell expressing PDX1 and NKX6.1 into beta cells, preferably glucose-responsive and/or insulin-producing beta cells. In some embodiments, the starting cell population has been enriched for pancreatic progenitor cells as described herein above.

Preferably, at least one cell of the starting cell population cells has the capability to differentiate further. The population may have the capability to differentiate further into pancreatic hormone-producing cells. In some embodiments, at least one of the pancreatic hormone-producing cells is an insulin-producing cell. In some embodiments, at least one of the pancreatic hormone-producing cells is responsive to glucose. In some embodiments, at least one of the pancreatic hormone-producing cells is an insulin-producing cell, which is also responsive to glucose. In some embodiments, at least one cell of the cell population enriched for pancreatic progenitor cells can produce insulin-producing islet cells.

In some embodiments, the at least one of the pancreatic hormone-producing cells has increased expression of at least one of insulin, C-peptide, Insm-1, Isl-1, MafA and MafB compared to a cell population that has been incubated in the absence of the Yap1 inhibitor. In one embodiment, the pancreatic hormone-producing cell is a mature β cell.

In some embodiments, CDKN1a and/or CDKN2a is inactivated in the starting cell population. In one embodiment, CDKN1a is inactivated. In another embodiment, CDKN2a is inactivated. In another embodiment, CDKN1a and CDKN2a are both inactivated. In another embodiment, CDKN1a and CDKN2 are inactivated sequentially, i.e. one of CDKN1a and CDKN2a is inactivated in a first step, and the other of CDKN1a and CDKN2a is inactivated in a second step; the first and second steps may overlap in time or be independent.

Treatment of Metabolic Disorder

Also disclosed herein is a cell population comprising beta cells, obtainable any of the methods disclosed herein, for treatment of a metabolic disorder in an individual in need thereof. The beta cells are preferably glucose-responsive and/or capable of producing a pancreatic hormone such as insulin.

Also disclosed herein is a method of treatment of a metabolic disorder in an individual in need thereof, wherein the method comprises a step of providing a population of beta cells obtainable by the methods disclosed herein and transplanting said population of beta cells into said individual.

The cell populations described herein can be used for treatment of metabolic disorders. Glucose-responsive beta cells obtained by the methods described herein are used for treating a metabolic disorder. The starting cell population may have been further enriched for pancreatic progenitors as described above, for example by the use of ligands binding markers as detailed above and isolation by flow cytometry. These isolated cells can be stored prior to use, or they can be used immediately. The cells may be differentiated further as described herein. Once a cell population with the desired characteristics is obtained, the cells are transplanted into an individual in need thereof. As an example, such cell-based therapy is useful for transplanting insulin-producing β-cells in individuals suffering from diabetes, whereby insulin production may be restored in vivo. If the starting cell population is derived from the patient him/herself, the risks of adverse immune reactions such as rejection of the transplanted cells may be reduced. As an alternative to transplanting insulin-producing β-cells into a patient, pancreatic progenitor cells, such as the cells obtainable by the methods described herein, can also be transplanted.

The term 'metabolic disorder' as used herein shall be construed to refer to endocrine, nutritional and metabolic diseases. Preferably, the disorder is related to a pancreatic disorder. Examples of metabolic disorders are: diabetes mellitus, including type 1 and type 2 diabetes.

Diabetes mellitus, commonly referred to as diabetes, is a group of metabolic diseases in which there are high blood sugar levels over a prolonged period. Several types of diabetes exist, including type 1 diabetes, type 2 diabetes and gestational diabetes. Type 1 diabetes is characterized by loss of the insulin-producing β cells of the islets of Langerhans in the pancreas, leading to insulin deficiency. Type 2 diabetes is characterized by insulin resistance, which may be combined with relatively reduced insulin secretion. The defective responsiveness of body tissues to insulin is believed to involve the insulin receptor. Gestational diabetes, which resembles type 2 diabetes, occurs in about 2-10% of all pregnancies. The type of diabetes can also be classified as insulin-dependent diabetes mellitus, non-insulin dependent diabetes mellitus, malnutrition-related diabetes mellitus or unspecified diabetes mellitus.

The methods disclosed herein can be used to generate beta cells, in particular glucose-responsive beta cells. In some embodiments, the beta cells produce insulin. Accordingly, in some embodiments there is provided a population of beta cells for treatment of a metabolic disorder in an individual in need thereof. In some embodiments, the metabolic disorder is selected from the group consisting of diabetes mellitus such as insulin-dependent diabetes mellitus, non-insulin dependent diabetes mellitus, malnutrition-related diabetes mellitus or unspecified diabetes mellitus.

In some embodiments, the cell population for treatment of a metabolic disorder is obtained by the methods described above.

The cell population may have been further enriched for cells expressing PDX1 and NKX6.1 by any of the following steps:
- exposing a cell population comprising at least one pancreatic progenitor cell, wherein the pancreatic progenitor cell expresses PDX1 and NKX6.1, to a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells; wherein the third ligand recognises and binds to GP2; or
- exposing a cell population comprising at least one pancreatic progenitor cell, wherein the pancreatic progenitor cell expresses PDX1 and NKX6.1, to a second ligand which binds to a second marker specific for PDX1+ cells and selecting the cells that bind to said second ligand from the cells that do not bind to said second ligand, thereby enriching the cell population for PDX1+ cells and to a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells, wherein the second ligand recognises and binds to FOLR1, and the third ligand recognises and binds to GP2; or
- exposing a cell population comprising at least one pancreatic progenitor cell, wherein the pancreatic progenitor cell expresses PDX1 and NKX6.1, to a first ligand which binds to a first marker specific for PDX1– cells and selecting the cells that do not bind to said first ligand from said cell population, thereby enriching the cell population for PDX1+ cells; and to a second ligand which binds to a second marker specific for PDX1+ cells and selecting the cells that bind to said second ligand from the cells that do not bind to said second ligand, thereby enriching the cell population for PDX1+ cells; and to a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells, wherein the first ligand recognises and binds to CD49d, the second ligand recognises and binds to FOLR1, and the third ligand recognises and binds to GP2;

or any of the methods described herein elsewhere.

In one aspect is provided a method of treatment of a metabolic disorder in an individual in need thereof, wherein the method comprises a step of providing a beta cell population obtainable by the methods described herein. In some embodiments, the beta cell population produces insulin. In some embodiments, the beta cell population is glucose-responsive.

In some embodiments, the present methods comprise a step of transplanting at least part of said cell population into the individual suffering from a metabolic disorder.

EXAMPLES

Stem cell-based therapy for type 1 diabetes would benefit from implementing a cell purification step at the pancreatic endoderm stage. This will increase the safety of the final cell product, allow the establishment of an intermediate stage stem cell bank, and provide new means for up-scaling β-cell manufacturing. Comparative gene expression analysis revealed glycoprotein 2 (GP2) as a specific cell surface marker for isolating pancreatic endoderm cells (PECs) from differentiated hESCs and human fetal pancreas. Importantly, isolated GP2+ PECs efficiently differentiated into glucose responsive insulin-producing cells in vitro. We discovered that PECs' proliferation in vitro declines due to enhanced expression of the CDK inhibitors CDKN1A and CDKN2A. However, we identified a time-window when reducing CDKN1A or CDKN2A expression increased proliferation and yield of GP2+ PECs. Altogether, our results contribute with new tools and concepts for the isolation and use of PECs as a source for safe production of hPSC-derived β-cells.

INTRODUCTION

The recent success in generating human pluripotent stem cell (hPSC)-derived glucose responsive insulin-producing cells that share functional properties with normal beta cells (Pagliuca et al., 2014, Rezania et al., 2014, Russ et al., 2015), has made the implementation of a cell-based therapy for the treatment of type 1 diabetes a tangible reality. The number of islet cells required for disease recovery has been estimated to around 300-750 million cells per patient (Bruni et al., 2014, Pagliuca et al., 2014). Thus, to be able to generate a sufficient number of hPSC-derived beta cells that is useful for a larger number of patients it will be necessary to implement expansion steps. Towards this end, expansion of either undifferentiated hPSCs (Schulz et al., 2012) or proliferative intermediate endodermal progenitors (Cheng et al., 2012, Zhu et al., 2016) has been explored.

During pancreas development, multipotent pancreatic endoderm cells (PECs) with inherent proliferative capacity, co-expressing PDX1, NKX6.1, and SOX9, are responsible for the proper growth of the organ (Kopp et al., 2011, Schaffer et al., 2010, Seymour et al., 2007). The pancreatic epithelium proliferates and expands between E8.5-E11.5 in the mouse (Stanger et al., 2007) corresponding to 25-35 days post conception in human development (Jennings et al., 2013, Nair and Hebrok, 2015). In contrast to more committed cells with limited to no proliferative capacity, such as the NEUROG3 (NGN3)+ endocrine progenitors (Castaing et al., 2005), PECs give rise to all mature pancreatic epithelial derivatives, including acinar, ductal, and endocrine cells (Gu et al., 2002, Herrera, 2002, Kawaguchi et al., 2002).

Previous attempts have identified putative markers for hESC-derived PECs (CD142) and endocrine cells (CD200/CD318) (Kelly et al., 2011). However, more specific PEC markers remain to be identified since CD142 labels additional cell types (Kelly et al., 2011).

Proliferation of pancreatic progenitors (both human and mouse) can be induced by co-culture with mesenchymal or endothelial cells (Cheng et al., 2012, Sneddon et al., 2012) or by the addition of mitogenic signals such as FGFs, or EGF (Bonfanti et al., 2015, Elghazi et al., 2002, Zhu et al., 2016). However, it remains unclear whether the proliferative capacity of PECs in vitro corresponds to the self-renewal of PE that underlies organ growth in vivo (Stanger et al., 2007). Thus, to develop new strategies for expanding pure populations of PECs, it is necessary to both improve methods for isolating pure populations of PECs and understand how PEC proliferation is regulated. In this study, we identified glycoprotein 2 (GP2) as a specific cell surface marker for the isolation of human PECs from differentiated hESCs and the human fetal pancreas. Furthermore, we showed that re-plated GP2+ PECs retain the capacity to differentiate with high efficiency into glucose-responsive insulin producing beta-like cells. In addition, we discovered that as PECs mature into PDX1+/NKX6.1$^{high}$ cells in vitro, the expression of the negative cell cycle regulators CDKN1a (also known as p21) and CDKN2a (also known as p16) increase. Specifically, we identified a temporal window in which the proliferation and yield of early PDX1+/NKX6.1$^{low}$ PECs can be enhanced through reduced expression of CDKN1A or CDKN2A. Altogether, our study provides key elements towards a novel strategy where isolated GP2+ PECs can be used as a new source for production of beta cells for future cell replacement therapy in type 1 diabetes.

Results

Figures 1B, 1C:
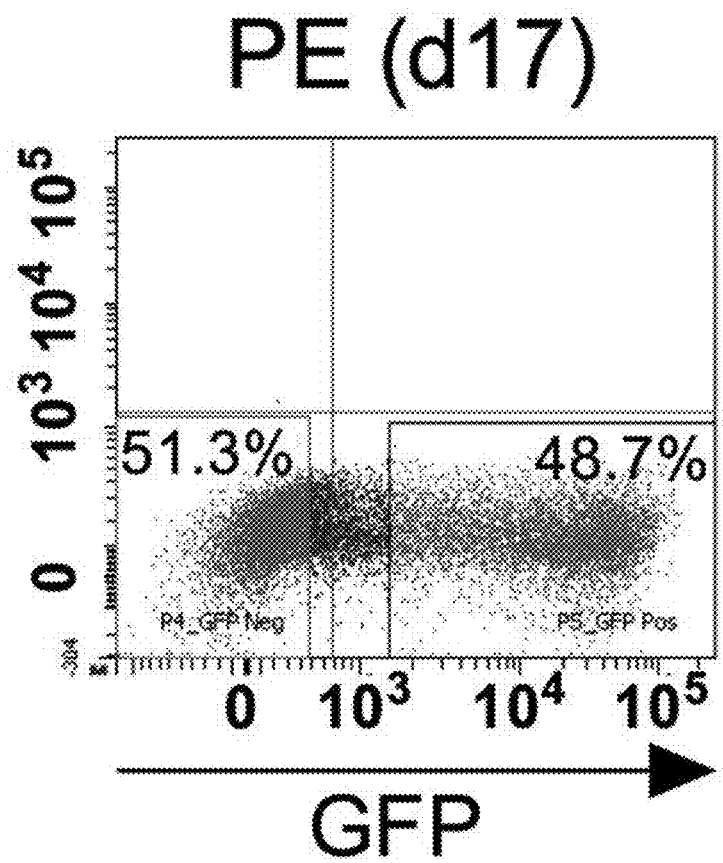
Figure 1D:
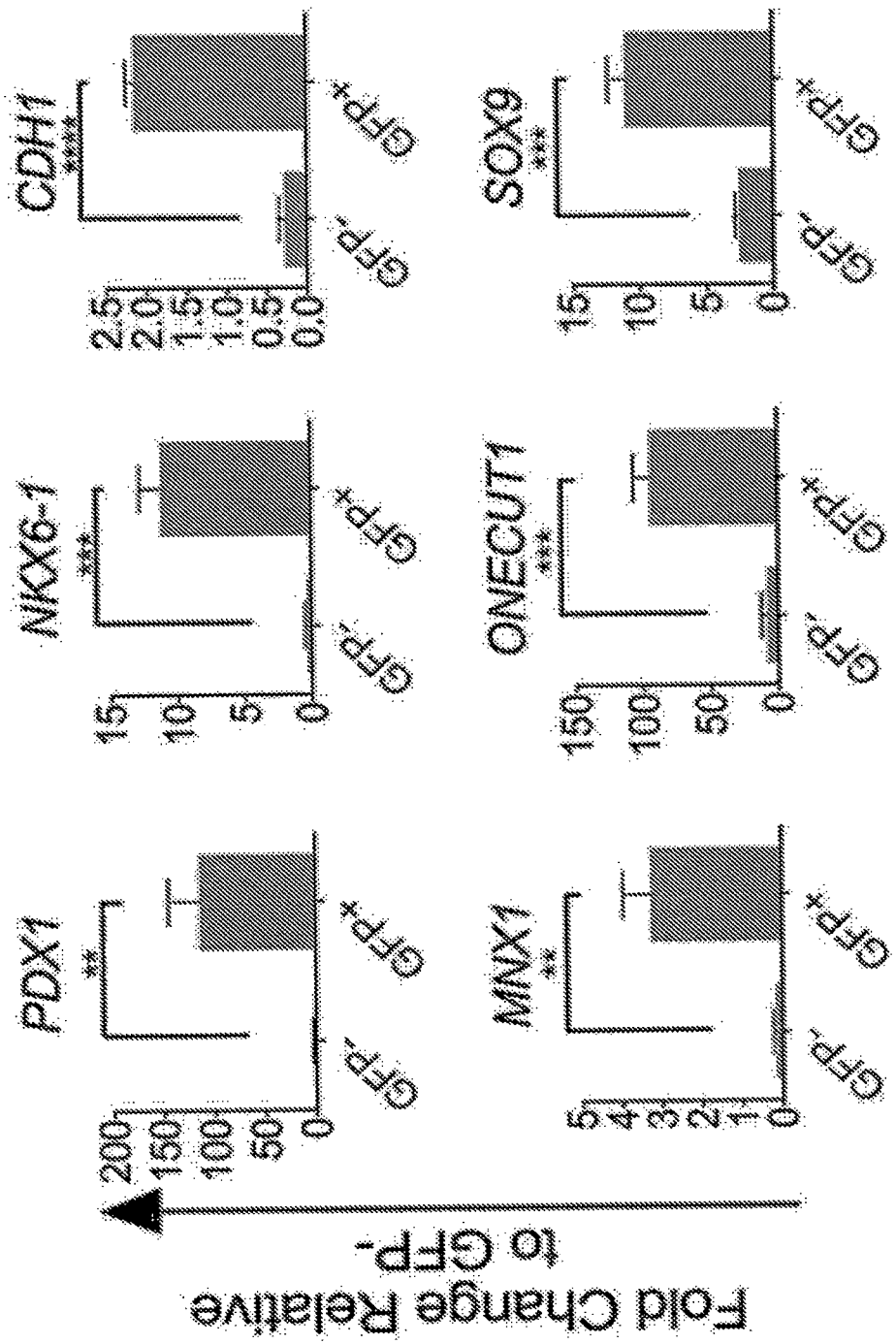
Figures 1E, 1F:
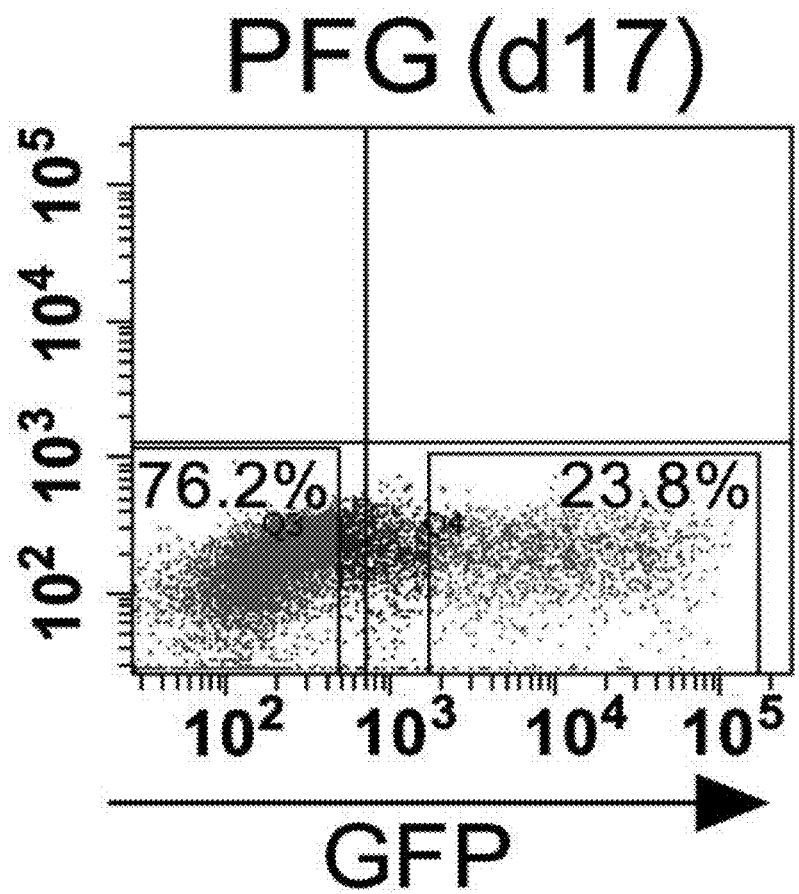

Comparative Gene Expression Analysis of Pancreatic and Posterior Foregut Endoderm To define the specific gene expression signature of PECs and identify PEC-specific cell surface markers, we first designed a strategy for generating putative PECs (PDX1+/NKX6.1+, protocol A, FIGS. 1A, 1B) and posterior foregut endoderm (PFG) cells (PDX1+/NKX6.1+, protocol B, FIGS. 1A, 1E). Analysis of the gene expression pattern of known pancreatic endoderm markers in PDX1+ and PDX1− cells (GFP+ and GFP− cells using a PDX1-eGFP hESC reporter (PDXeG)) (Figure S1A-F of Ameri et al. 2017) demonstrated that PDX1, CDH1, ONECUT1, and SOX9 were all significantly up-regulated in the GFP+ cells generated by both protocols (FIGS. 1C, 1D, 1F and 1G). However, while protocol A generated GFP+ cells with significant PDX1, NKX6.1 and MNX1 upregulation, the GFP+/PDX1+ cells from protocol B expressed lower levels of NKX6.1 and MNX1 (FIGS. 1D, 1G). Immunostainings at day 17 confirmed the expression of NKX6.1, SOX9, CDH1, and HES1 in the pancreatic endoderm cells obtained with protocol A (Figure S1G of Ameri et al. 2017 and data not shown). Altogether, these results suggest that the GFP+ cells obtained with protocol A represent bona fide PECs, while GFP+ cells obtained with protocol B correspond to PFG cells.

Figure 2A:
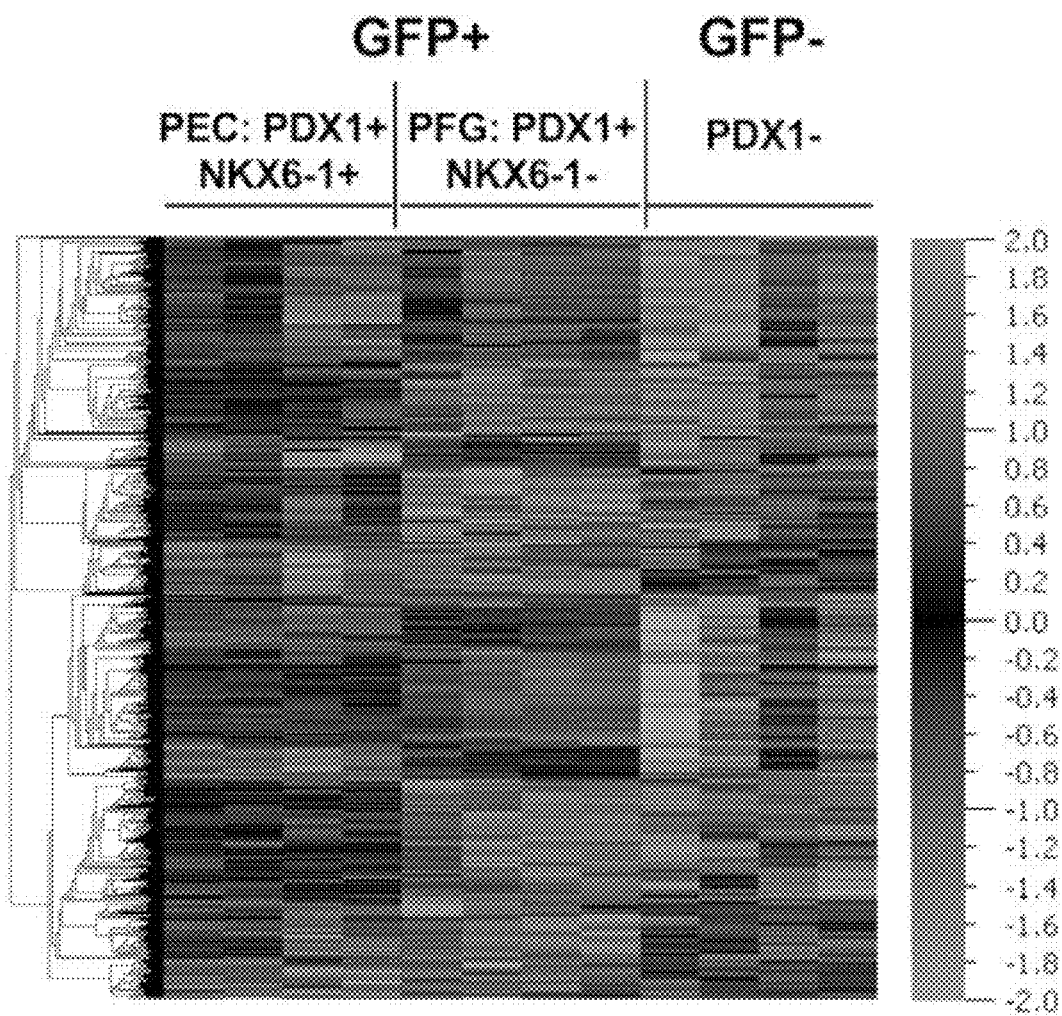
Figure 2B:
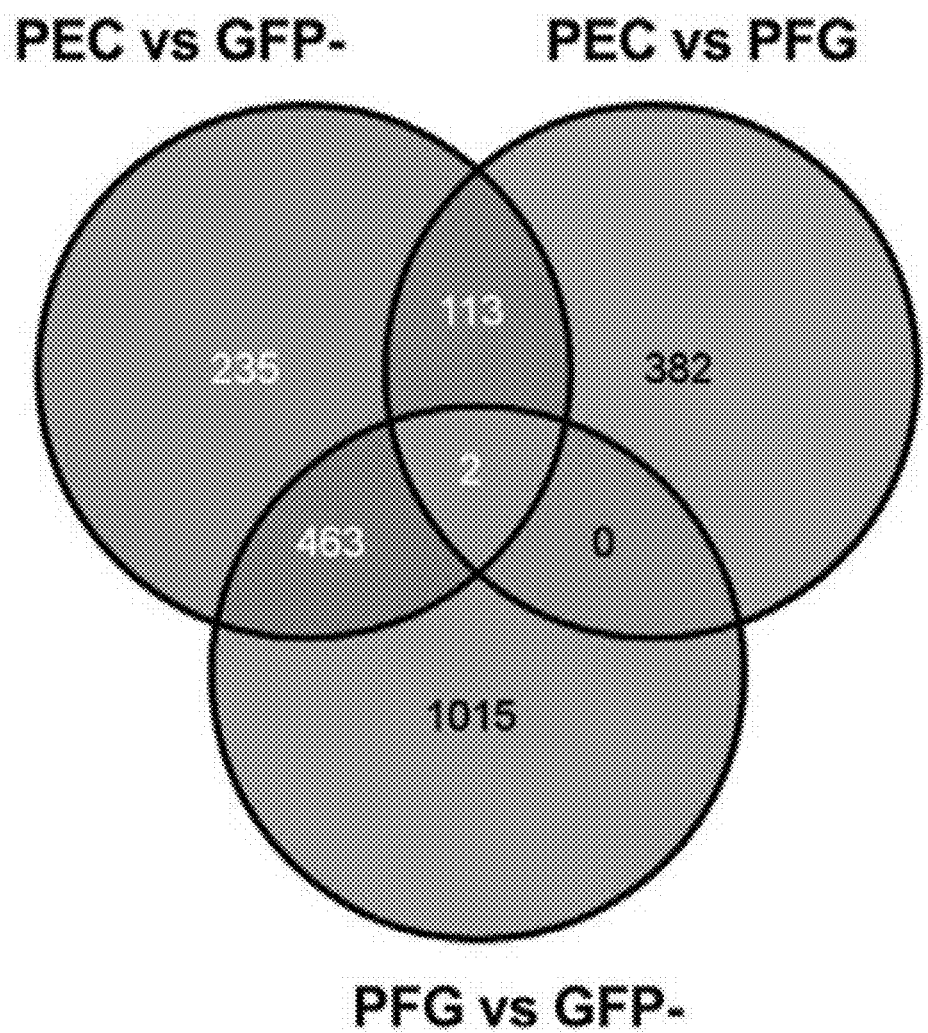
Figure 2D:
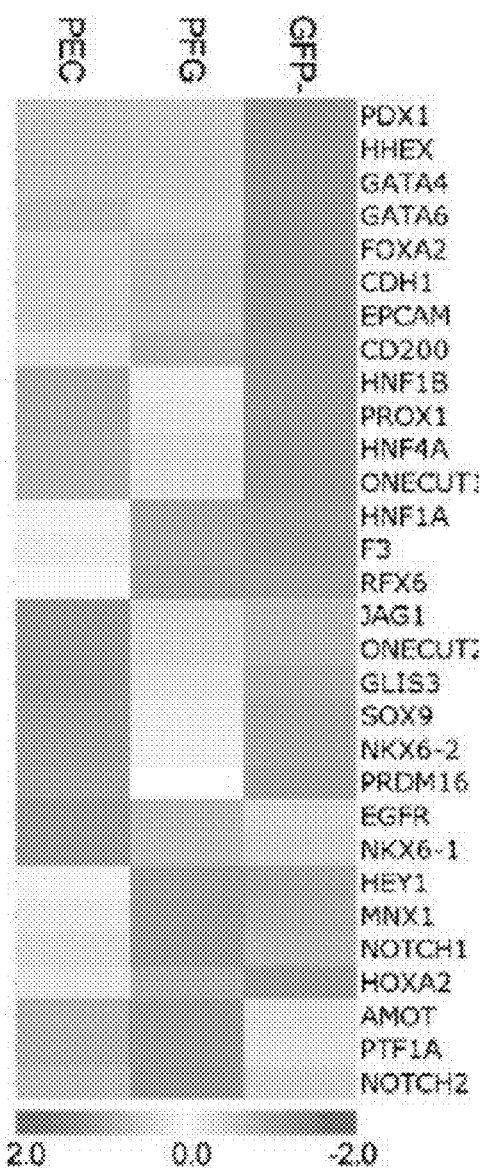

Identification of Novel Cell Surface Markers for Prospective Isolation of PECs To identify PEC-specific cell surface markers, we performed microarray analysis to compare the gene expression pattern in PDX1+/NKX6.1+ (GFP+ PECs), PDX1+/NKX6.1− (GFP+ PFG) and PDX1− (GFP−) cells (FIG. 2A). Only genes with a fold change above 1.4 (P<0.005) were selected for further analysis. A total of 3403 genes (3791 probe sets) were differentially expressed among the three sample groups. Hierarchical clustering revealed 382 genes enriched in PECs compared to PFG cells, while 698 genes were enriched in the PECs compared to GFP− cells. Interestingly, 115 genes were specifically enriched in PECs compared to PFG and GFP− cells (FIG. 2B and Table S1). Gene ontology analysis showed that processes related to proliferation (e.g. cell cycle, epithelial cell proliferation, DNA replication) were significantly enriched in the PDX1+/NKX6.1+ PECs (FIG. 2C). Consistent with our initial analysis, genes that are induced early during pancreatic endoderm specification such as PDX1, HHEX, GATA4 and FOXA2 were present in both PECs and PFG cells, while markers of late PECs, such as NKX6.1, SOX9, ONECUT1/2, and PRDM16 were specifically enriched in the PEC population (FIG. 2D). Of note, CD142 (also known as F3) and CD200, two cell surface markers previously shown to enrich for pancreatic endoderm cells and endocrine progenitors (Kelly et al., 2011), were expressed in both PECs and PFG cells (FIG. 2D).

Figure 2E:
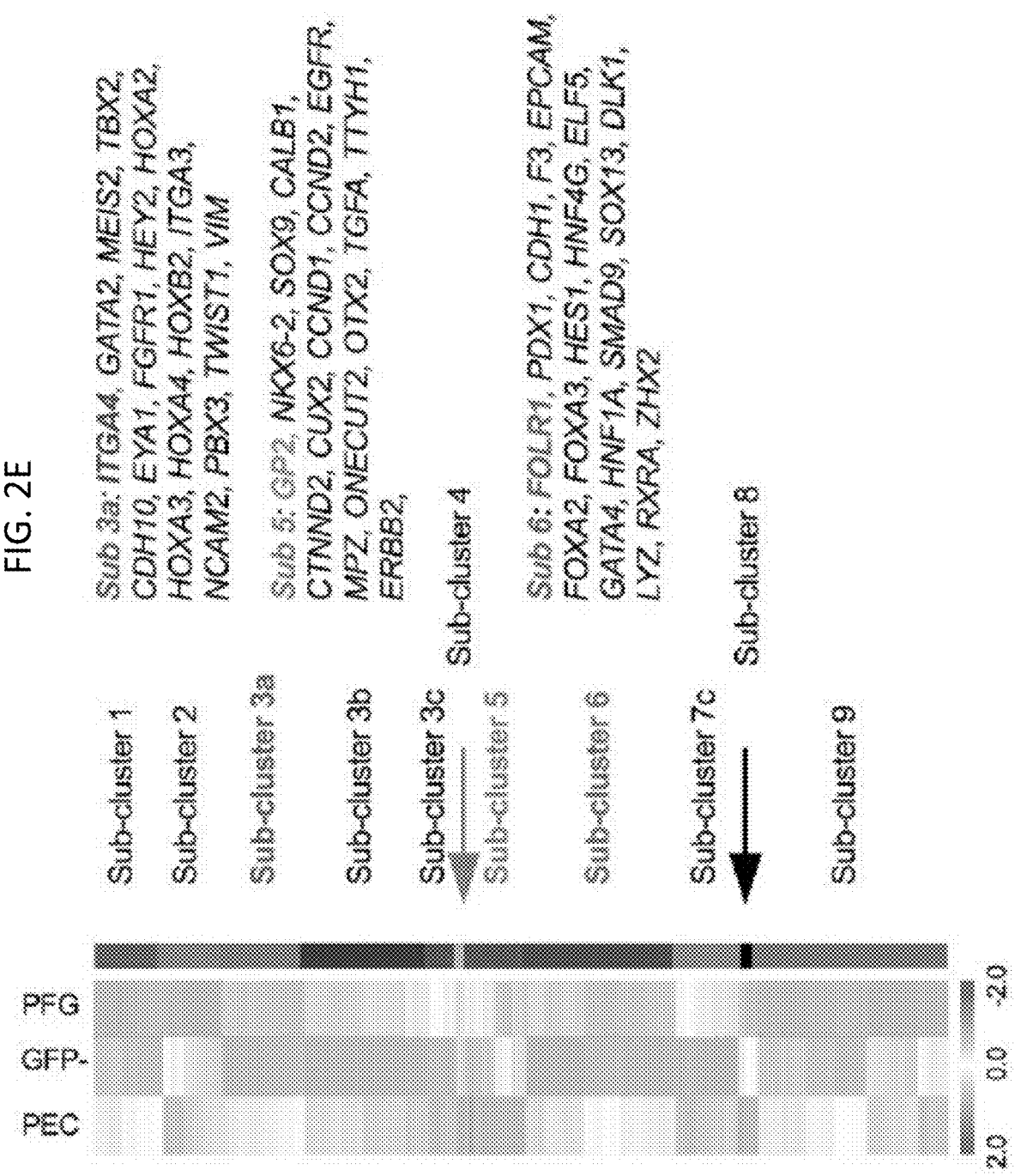

For a more in depth analysis, nine different sub-clusters were created by hierarchical clustering. Sub-cluster 3a represents genes enriched in the GFP$^-$ cells, including the mesenchymal markers GATA2, MEIS2, TBX2, EYA1, FGFR1, HEY2, HOXA2, and VIM. Genes enriched in both PECs and PFG cells were confined to sub-cluster 6: PDX1, CDH1, GATA4, HNF1a, F3, EPCAM, FOXA2, and HES, whereas pancreatic endoderm associated genes in sub-cluster 5, such as NKX6.2, SOX9, EGFR, ERBB2, and ONECUT2, were up-regulated in PECs (FIG. 2E). Importantly, we identified cell surface makers that could potentially be used for the isolation of PECs. Specifically, glycoprotein 2 (zymogen granule membrane GP2) was enriched in PDX1$^+$/NKX6.1$^+$ PECs (Sub-cluster 5), Folic receptor 1 (FOLR1) in all PDX1$^+$ cells (Sub-cluster 6), and Integrin alpha 4 (ITGA4 or CD49d) was enriched in GFP$^-$ cells (Sub-cluster 3a) (FIG. 2E). Overall, our expression analysis not only reveals a new set of genes uniquely expressed in PECs, but also provides putative new cell surface markers for isolation of PECs.

Functional Validation of Novel Cell Surface Markers

Figure 3A:
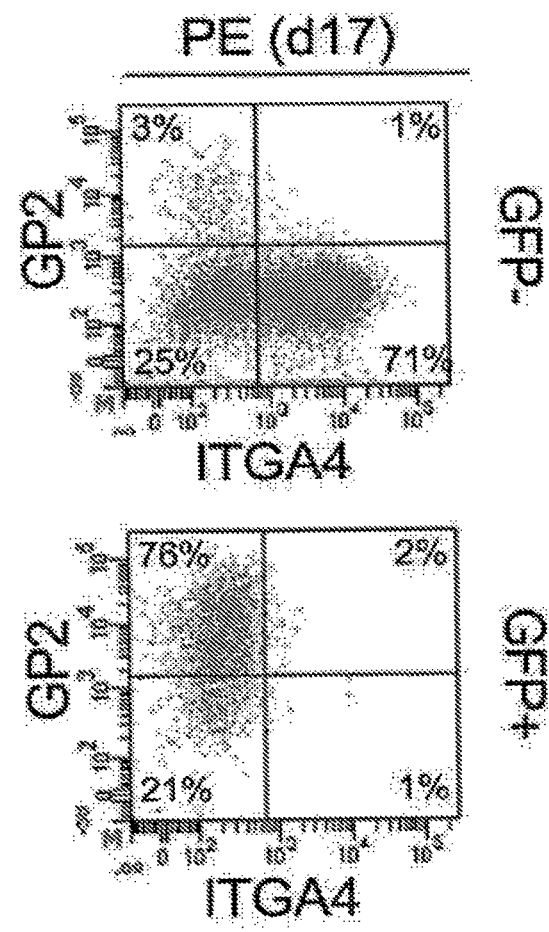
FIGS. 3A-3G. Validation of the novel cell surface markers GP2 and ITGA4 in hESCs and human fetal pancreas.
Figure 3B:
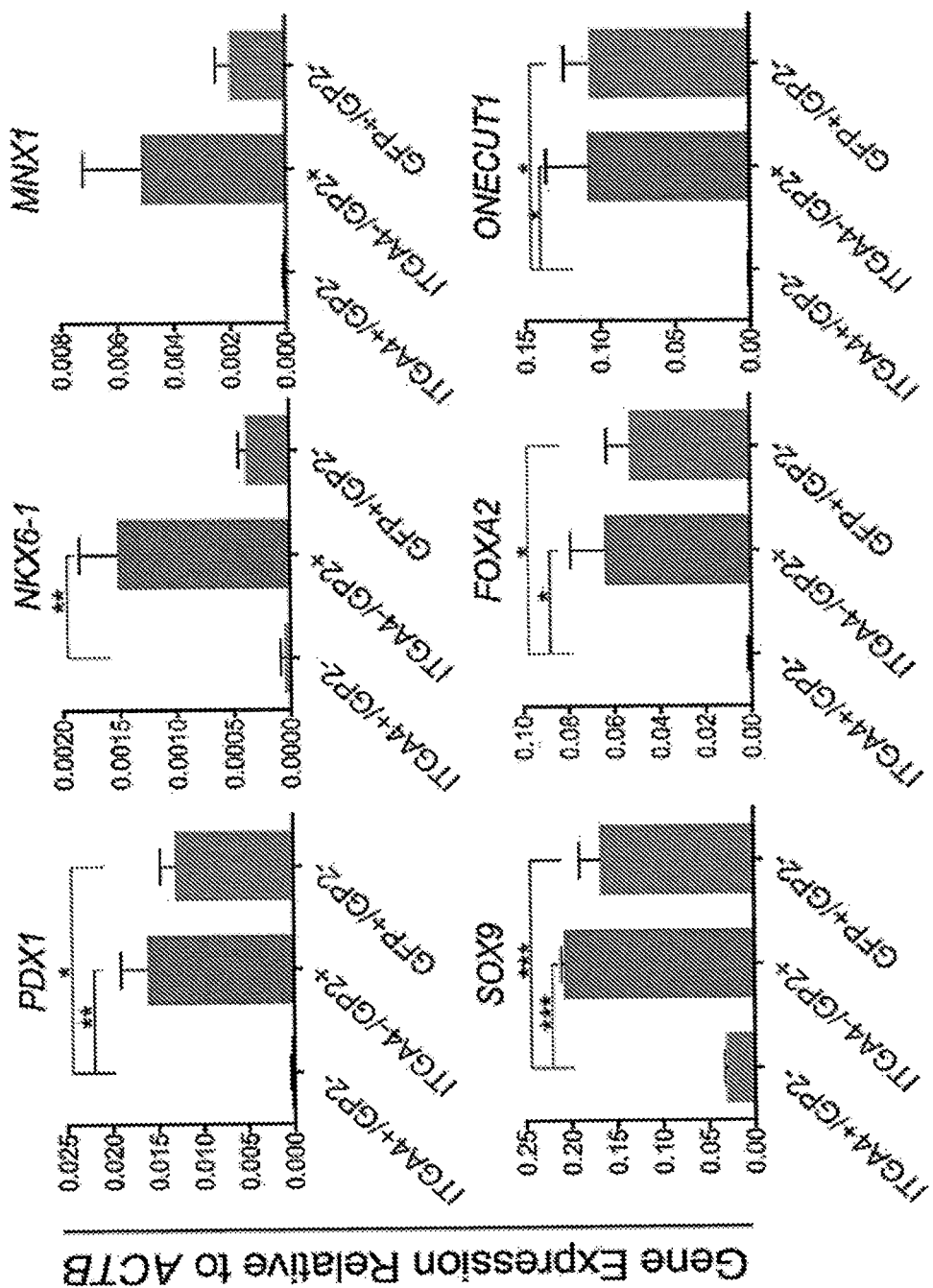

To validate GP2, FOLR1, and ITGA4 for the isolation of PECs, flow cytometry analysis of differentiated PDXeG cells was carried out (FIG. 3A). Double staining with antibodies against GP2 and ITGA4 showed that the majority of the GFP$^+$ cells (76%) co-expressed GP2, while 71% of the GFP$^-$ cells expressed ITGA4 at day 17. Importantly, only a low fraction of the GFP$^-$ cells (3%) expressed GP2 and basically none (1%) of the GFP$^+$ cells expressed ITGA4 (FIG. 3A). To confirm GP2's specificity in labeling the PDX1$^+$/NKX6.1$^+$ cells, gene expression analysis on sorted cell fractions (ITGA4$^+$/GP2$^-$, ITGA4$^-$/GP2$^+$, and GFP$^+$/GP2$^-$) was performed. This analysis revealed that the pancreas associated markers PDX1, NKX6.1, MNX1, SOX9, FOXA2, and ONECUT1 were all significantly enriched in the ITGA4$^-$/GP2$^+$ cells compared to the ITGA4$^+$/GP2$^-$ cells. Furthermore, while similar levels of PDX1, SOX9, FOXA2, and ONECUT1 were expressed in GFP$^+$/GP2$^-$ and ITGA4$^-$/GP2$^+$ cells, NKX6.1 and MNX1 were exclusively enriched in ITGA4$^-$/GP2$^+$ cells (FIG. 3B). As expected, both GP2 and FOLR1 were enriched in the ITGA4$^-$/GP2$^+$ cells, whereas ITGA4 was enriched in the ITGA4$^+$/GP2$^-$ cells (Figure S2A of Ameri et al. 2017). Similar results were obtained from the gene expression analysis performed on the cell fractions stained with FOLR1 and ITGA4, (Figure S2B,C of Ameri et al. 2017). Altogether, these results suggest that GP2 and FOLR1 represent specific markers for PECs.

Figure 3C:
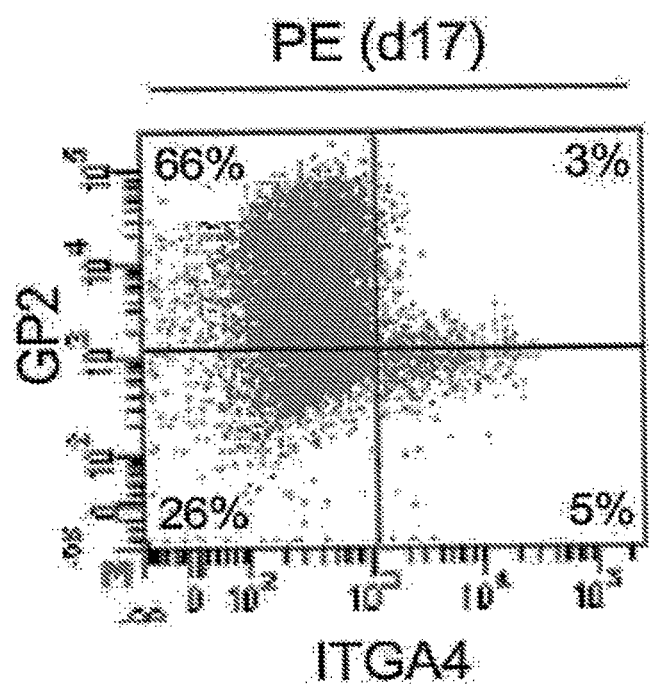
Figure 3D:
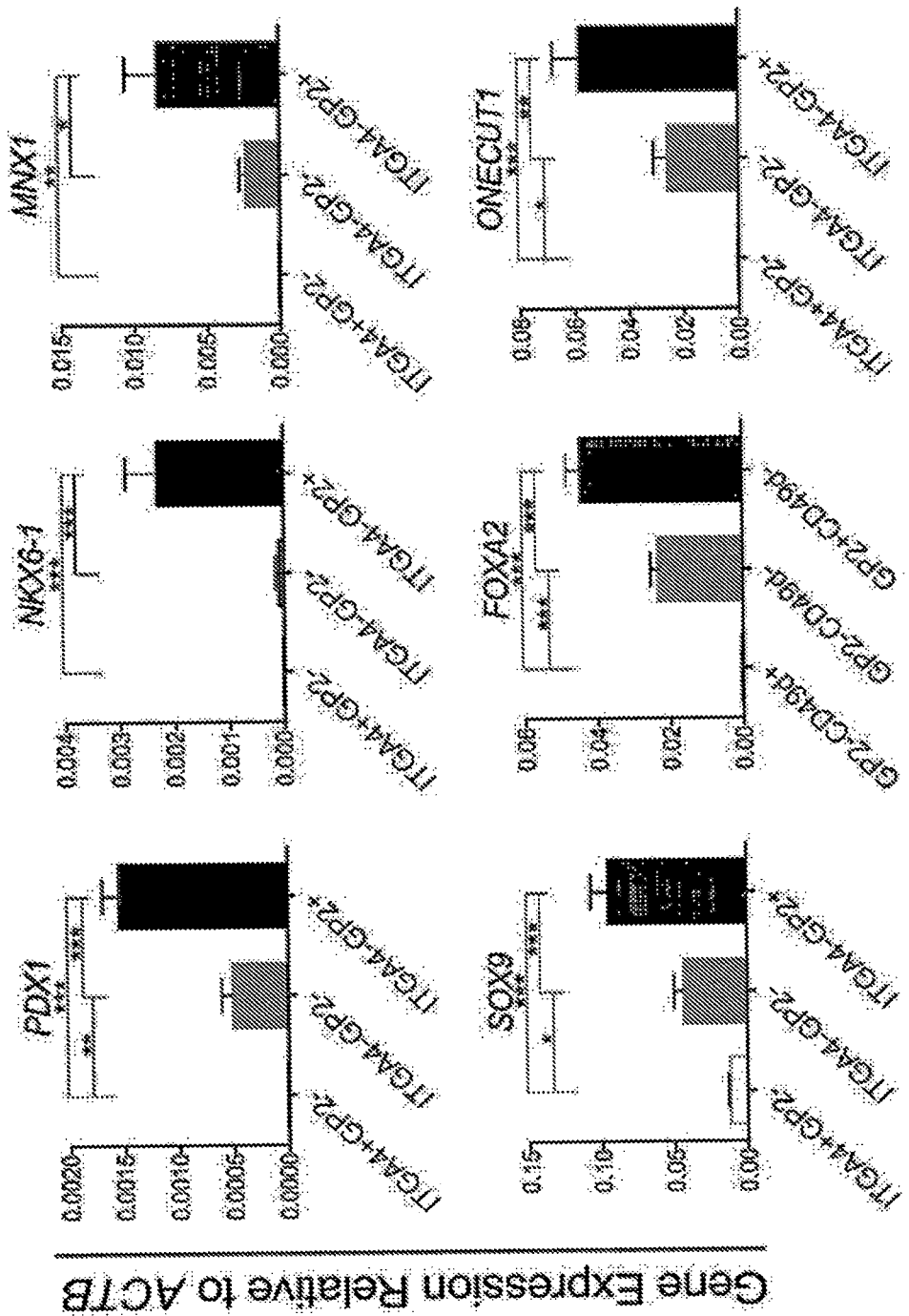

Next, we confirmed the cell surface markers in genetically unmodified hESCs under feeder-free conditions. This adaptation resulted in few ITGA4$^+$ cells (FIG. 3C and Figure S2E of Ameri et al. 2017). Consistent with the previous results, the pancreatic markers PDX1, NKX6.1, SOX9, ONECUT1, FOXA2, MNX1 were all significantly enriched in ITGA4$^-$/GP2$^+$ cells in comparison to ITGA4$^+$/GP2$^-$ and ITGA4$^-$/GP2$^-$ cells (FIG. 3D). PDX1 expression was still detectable in the ITGA4$^-$/GP2$^-$ cells; however, these cells expressed low levels of NKX6.1 (FIG. 3D), and GP2 (Figure S2D of Ameri et al. 2017), suggesting that these cells most likely represent PDX1$^+$ PFG cells. Consistently, FOLR1 was also expressed in the ITGA4$^-$/GP2$^-$ cell fraction (Figure S2F of Ameri et al. 2017). Moreover, although pancreatic markers were enriched in the ITGA4$^-$/FOLR1$^+$ cells, ITGA4$^-$/FOLR1$^-$ cells still expressed PDX1, NKX6.1, and GP2 (Figure S2F of Ameri et al. 2017). These data underscore that while GP2 is highly specific for hPSC-derived PDX1$^+$/NKX6.1$^+$ PECs, FOLR1 recognizes both PECs and PFG cells.

GP2 Enables Isolation of Bona Fide PECs from Human Fetal Pancreas

Figures 3E, 3F:
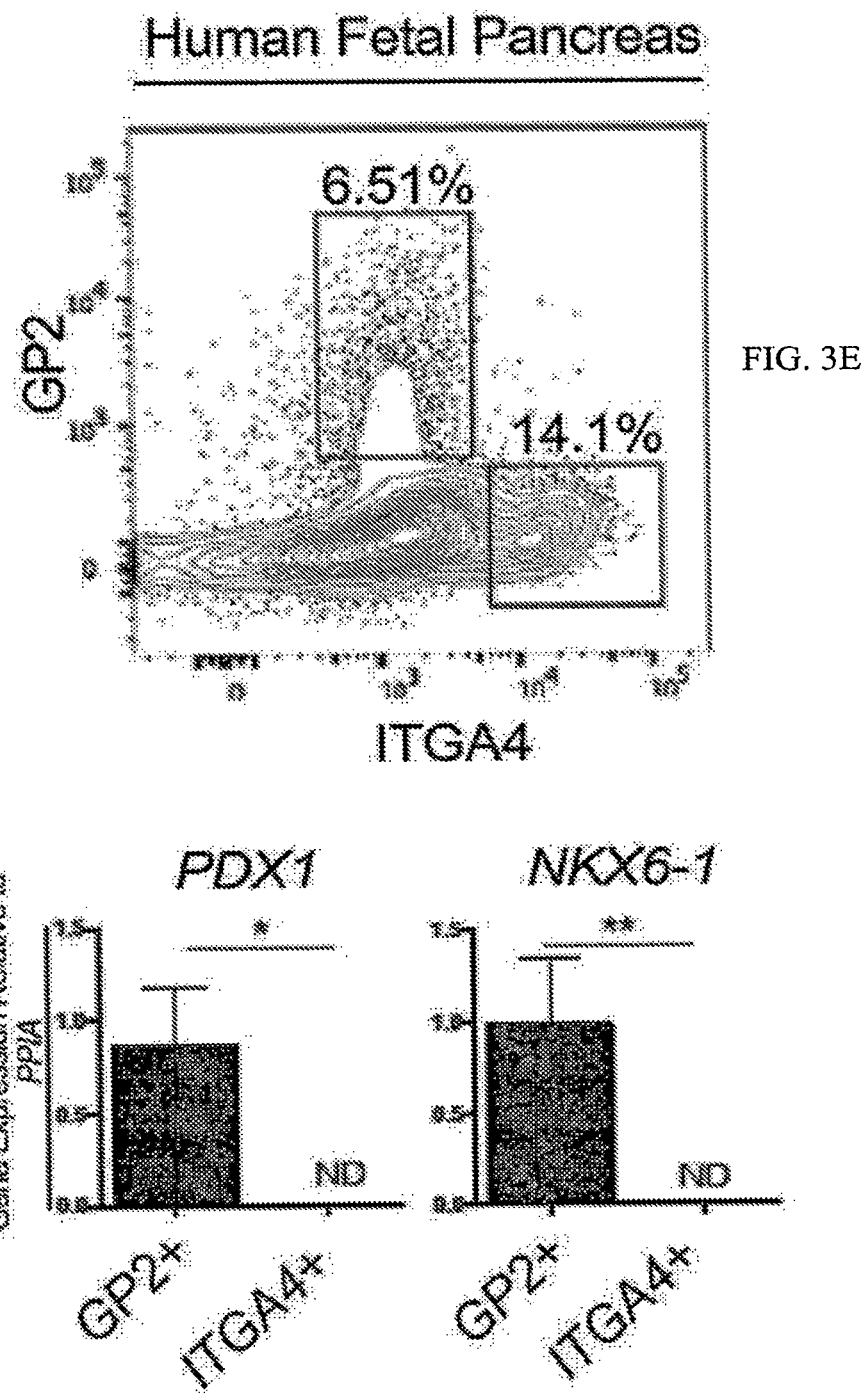
Figure 3G:
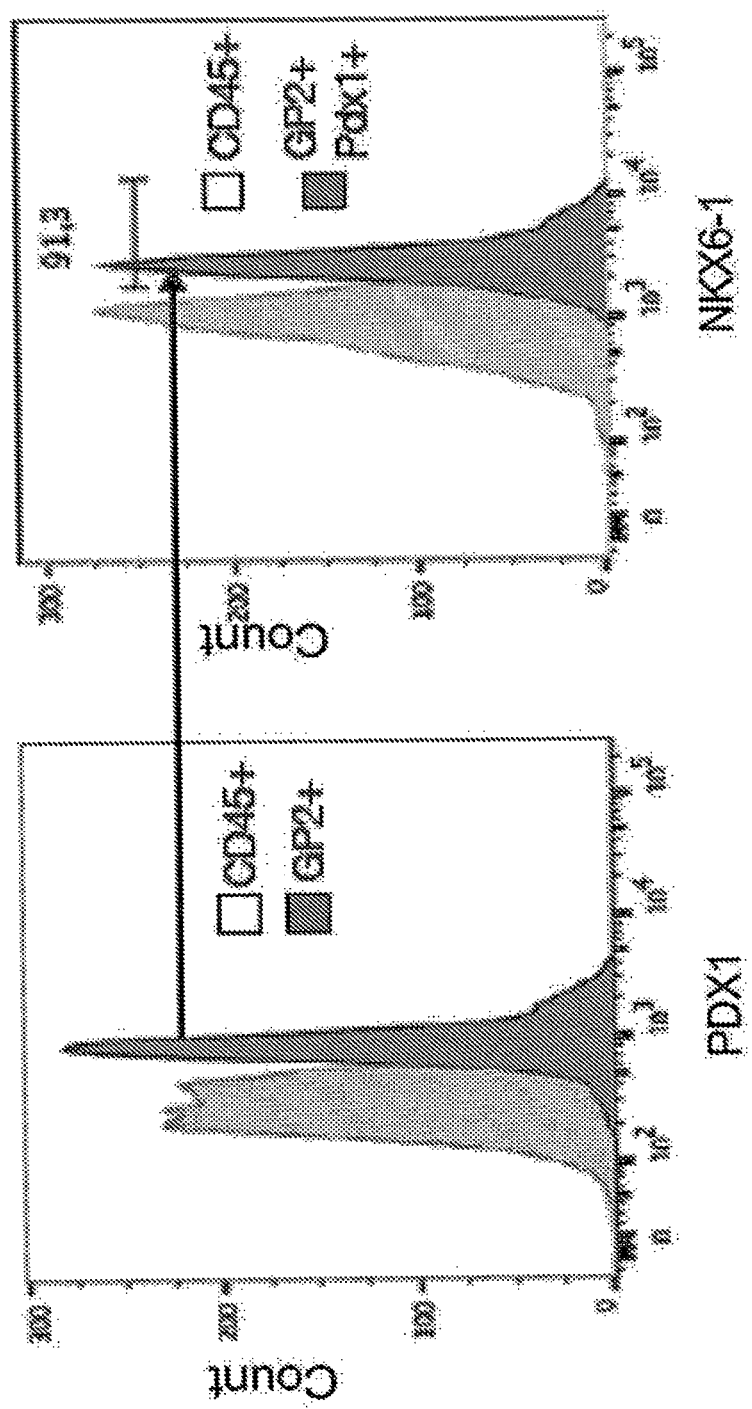

To corroborate the relevance of GP2 as a specific PEC marker, we examined the expression of GP2 and ITGA4 in human fetal pancreas at 9.1 weeks in development. Consistent with differentiated hESCs, GP2 and ITGA4 showed no overlap in the human fetal pancreas (FIG. 3E). While ITGA4 is expressed in the mesenchyme, GP2 is confined to the epithelium (data not shown). qPCR analysis showed that GP2$^+$ cells are significantly enriched for PDX1 and NKX6.1 (FIG. 3F). PDX1 and NKX6.1 co-expression was also confirmed in the GP2$^+$ cells by flow cytometry (FIG. 3G). Collectively, our results demonstrate that GP2 can be utilized for isolation of PDX1$^+$/NKX6.1$^+$ PECs from heterogeneous populations of differentiated hPSCs, as well as from human fetal pancreas in vivo.

Validation of GP2 Using an Independent Differentiation Protocol

Figures 4A, 4B, 4C:
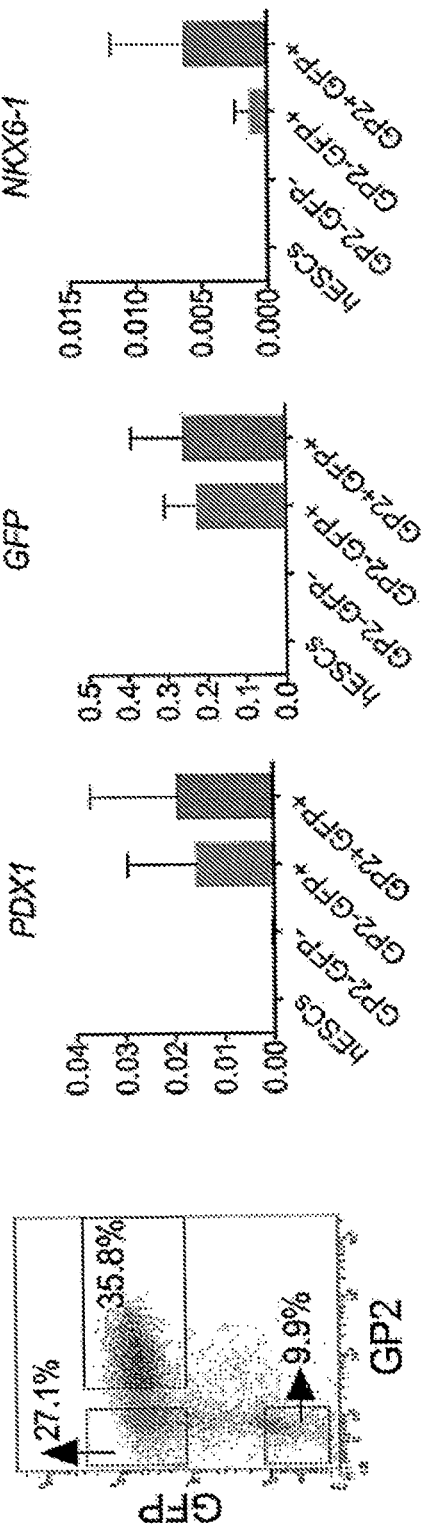
Figure 4C:
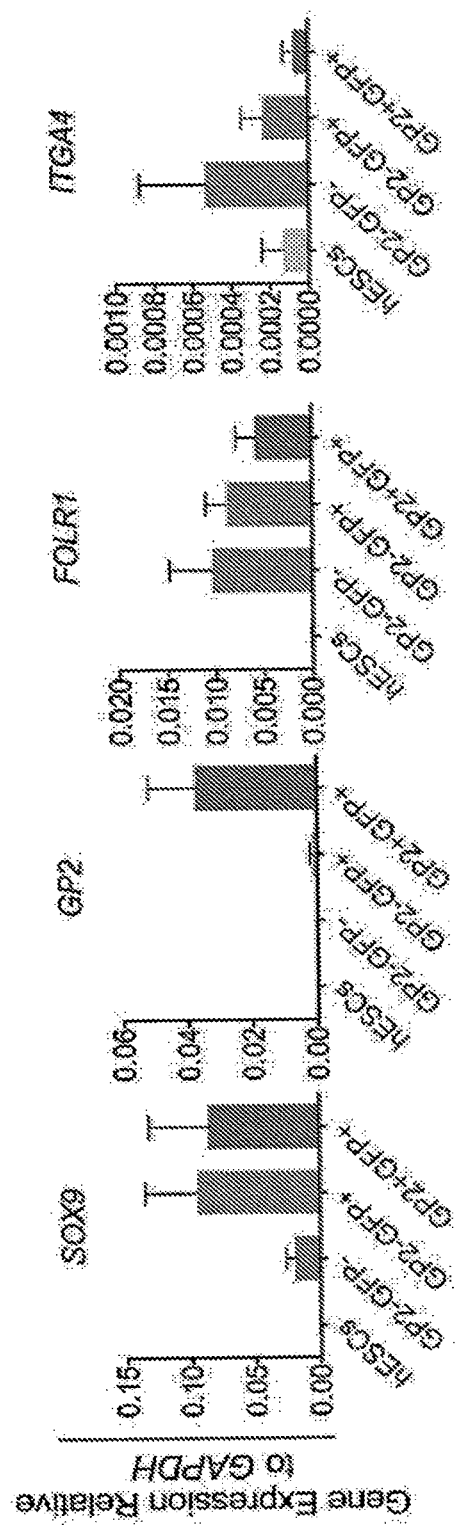

To further substantiate the ability of GP2 to specifically recognize PECs, we used a slightly modified version of a published feeder-free differentiation protocol (Rezania et al., 2013) (FIG. 4A-4D). This protocol generates a more heterogeneous cell population with less GP2$^+$ cells (FIG. 4B) in comparison to our modified protocol (FIGS. 4A, 5B). Consistent with the results shown above, GP2$^+$/GFP$^+$ cells expressed high levels of the PEC-associated genes PDX1, NKX6.1, SOX9, and GP2 (FIG. 4C). FOLR1 expression was detected in all sorted populations (GP2$^-$/GFP$^-$, GP2$^-$/GFP$^+$ and GP2$^+$/GFP$^+$ cells), highlighting again that GP2 is a more specific marker for PECs compared to FOLR1 (FIG. 4C). As expected, the highest level of ITGA4 was expressed in the GP2$^-$/GFP$^-$ cells (FIG. 4C). GP2-mediated enrichment of PECs was also confirmed at the protein level by co-staining the different cell fractions with antibodies against PDX1 and NKX6.1 (FIG. 4D). Finally, independent quantification analysis showed a similar percentage of GP2$^+$ and PDX1$^+$/NKX6.1$^+$ cells at the PE stage (14.8% GP2$^+$ cells vs 15% PECs) (FIGS. 4E-4G). Taken together, these results unambiguously show that GP2 specifically labels PDX1$^+$/NKX6.1$^+$ PECs.

Comparative Analysis of GP2 with CD142 and CD200

Analysis of the expression pattern of the previously reported cell surface markers CD142, CD200, and CD318 (Kelly et al., 2011) revealed that CD318 was significantly enriched in the PDX1$^-$/GFP$^-$ cells (data not shown), while CD142 and CD200 were present on both PDX1$^+$/GFP$^+$ and PDX1$^-$/GFP$^-$ cells (Figure S3A of Ameri et al. 2017). Comparative analysis of GP2 and CD142/CD200 stainings revealed that CD142 and CD200 labeled the majority of the differentiated cells, while GP2 only stained a subset of the cells (Figure S3A-C of Ameri et al. 2017). qPCR analysis of the sorted cell populations showed an enrichment of the PE specific genes PDX1, NKX6.1, and SOX9 in GP2$^+$ cells compared to CD142$^+$ and CD200$^+$ cells (Figure S3D of Ameri et al. 2017). Furthermore, immunostainings of the CD142$^+$ and CD200$^+$ cell fractions with PDX1 and NKX6.1 antibodies unequivocally showed that GP2 is superior in labeling PDX1$^+$/NKX6.1$^+$ PECs (Figure S3E of Ameri et al. 2017, FIG. 4D). Altogether, our findings demonstrate that GP2 specifically labels PDX1$^+$/NKX6.1$^+$ PECs and can be used for purification of PECs from heterogeneous populations of differentiated hPSCs independent of culture system or differentiation protocol.

Lineage Potential of GP2$^+$ PECs Towards Beta Cells

To assess the ability of isolated GP2$^+$ PECs to differentiate into mono-hormonal insulin-producing beta-like cells, we optimized our differentiation protocol depicted in FIG. 1B to generate glucose responsive beta-like cells (Protocol C, FIG. 8A). Specifically, two more stages were introduced where the cells were first differentiated in the presence of TPB and Noggin and finally in a medium containing Forskolin, ALK5i, Noggin and Nicotinamide. This new protocol generated on average 60-80% PDX1$^+$/NKX6.1$^+$ PECs at the PE stage (day 17-day 18) (FIG. 8B). This percentage can be directly correlated with the number of GP2$^{High}$ cells present in the culture (FIG. 8D).

Figure 8F:
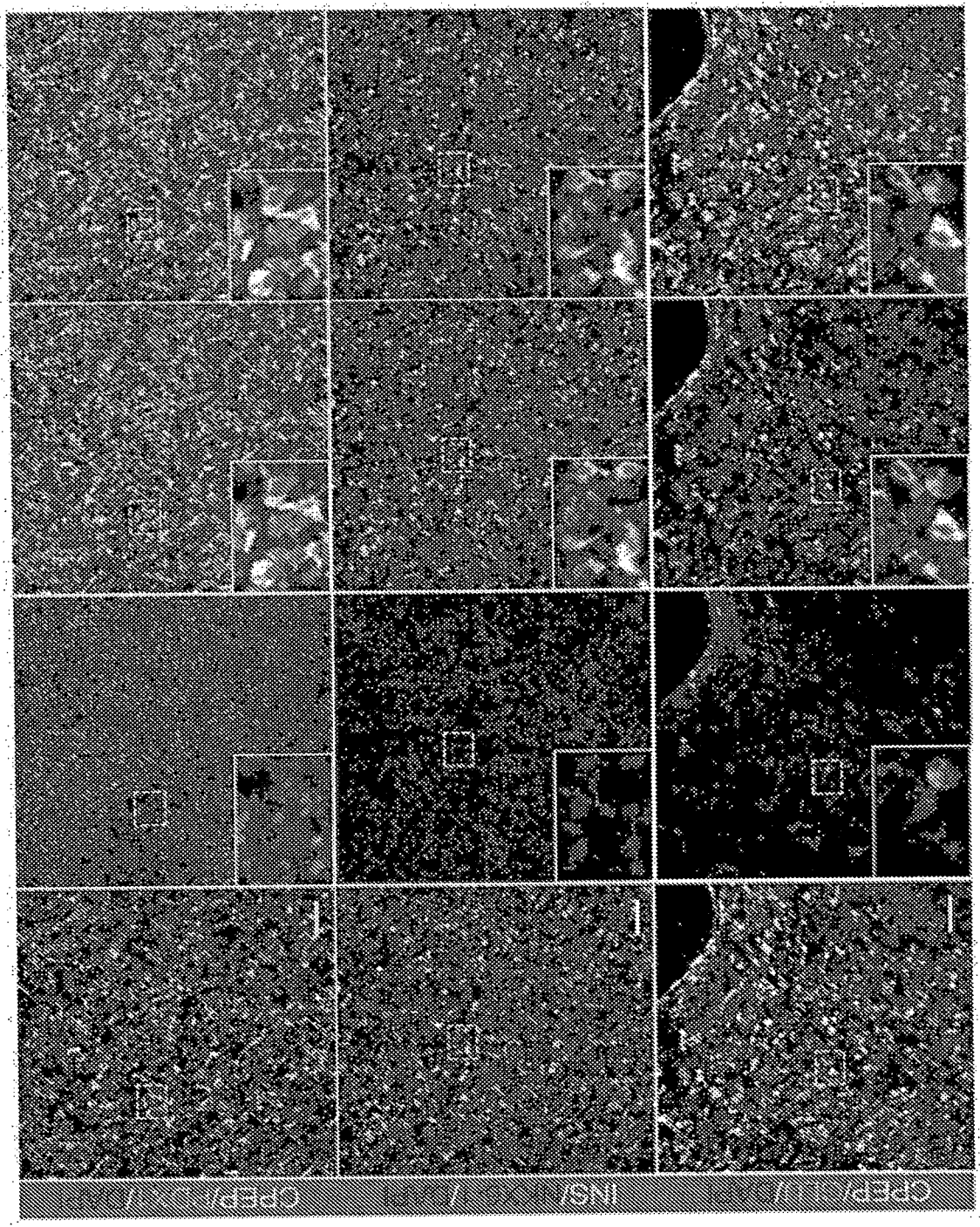

Furthermore, we have observed that the GP2$^{Low}$ cell population shifts into a GP2$^{High}$ cell population over time (data not shown), and that this shift correlates with the increase in NKX6.1 expression. This suggests that the GP2$^{High}$ cells are late PECs (co-expressing PDX1 and NKX6.1) whereas GP2$^{Low}$ cells are early PECs where NKX6.1 expression is just initiated. As the cells are differentiated further, INS and GLU gene expression is observed from day 23 onward (FIG. 8E). On day 32, glucose responsive C-peptide (CPEP$^+$) cells that were also positive for PDX1 and for NKX6.1 were detected, while very few Glucagon (GLU$^+$) cells (3.6%) were observed (FIGS. 8F-8H and see also FIG. 5G).

Figure 8H:
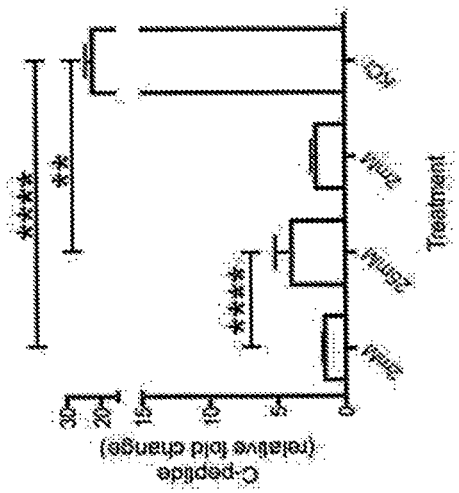
Figure 8G:
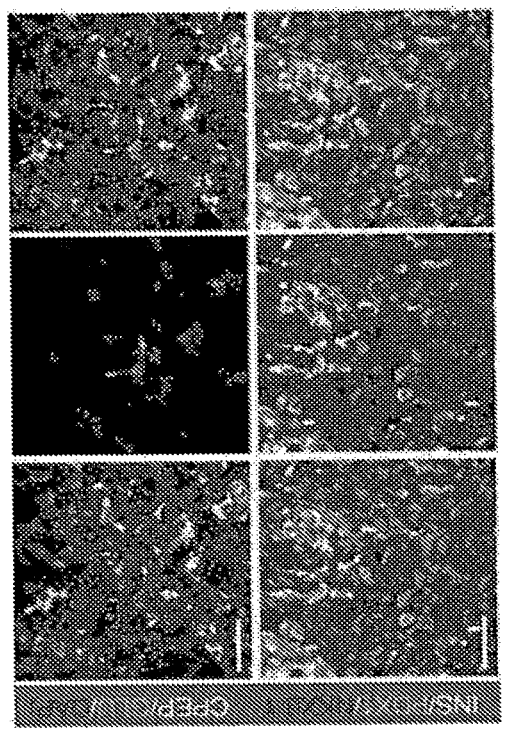

GP2$^+$ PECs sorted on day 18 were re-plated in the same differentiation medium for two weeks (FIGS. 5A, 5B). Negative selection with ITGA4 was not necessary as extremely few ITGA4$^+$ cells appeared (FIG. 5C). While CPEP$^+$ cells emerged from both GP2$^{High}$ cells and GP2$^{Low}$ cells, there was a significant enrichment of CPEP$^+$ cells from the GP2$^{High}$ cells (44% from GP2$^{High}$ vs 18% from GP2$^{Low}$) (FIGS. 5D, 5E). Similar to the unsorted cultures, few GLU$^+$ cells were observed, although GP2$^+$ purification at the PE stage also resulted in an enrichment of GLU$^+$ cells (8.3% vs 3.2%) (FIG. 5G). Furthermore, the majority of the mono-hormonal CPEP$^+$ cells co-expressed PDX1 and CPEP$^+$/NKX6.1$^+$ cells were also observed (FIG. 5F). Importantly, insulin secretion analysis of the CPEP$^+$ cells derived from GP2$^{High}$ cells revealed an approximately 2-fold increase in insulin release in response to high versus low glucose (FIG. 5H). This result corresponds to the behavior of CPEP$^+$ cells derived in unsorted cultures (FIG. 8H). The level of glucose responsiveness is also comparable to what has been previously published (Pagliuca et al., 2014, Rezania et al., 2014). Thus, we have developed for the first time an experimental system for generating glucose-responsive mono-hormonal CPEP$^+$ cells from isolated hPSC-derived GP2$^+$ PECs.

Figure 6D:
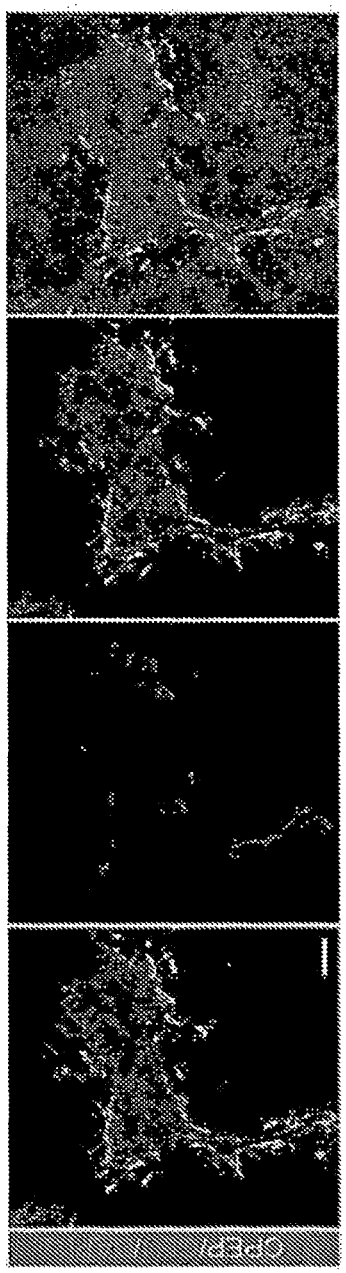
Figure 6E:
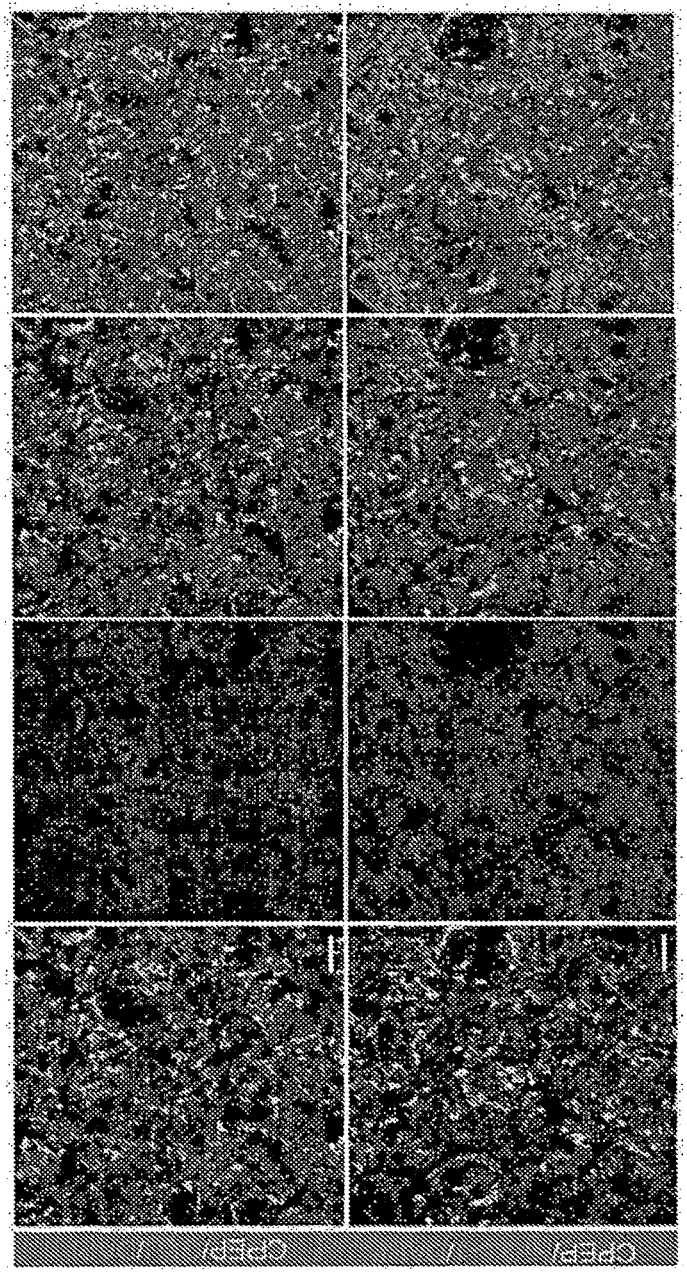
Figure 6F:
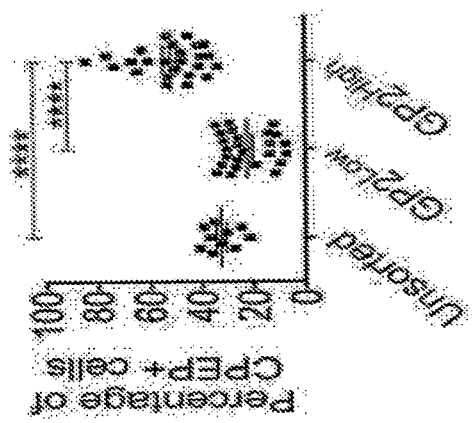
Figure 6G:
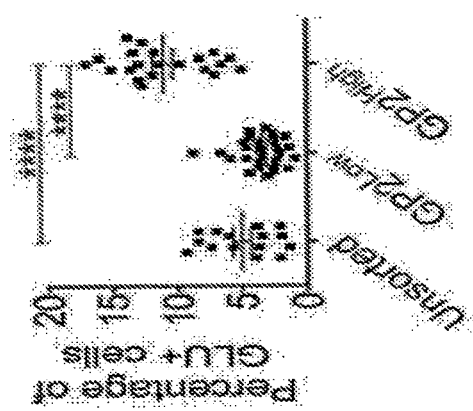
Figure 6H:
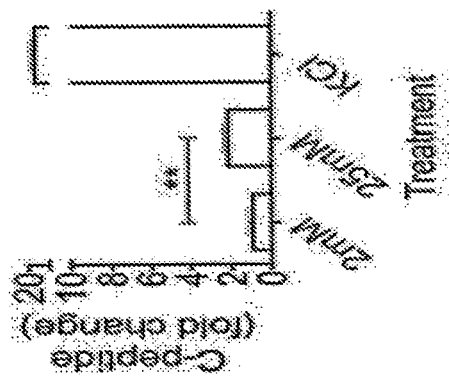

These experiments were finally repeated on the GMP graded hESC line MShef-7 (FIGS. 6A-6H). Similar to the HUES4 cell line, INS and GLU expression was detected from day 23 and onwards (FIG. 6A) and ITGA4$^+$ cells were scarce at day 17 (FIG. 6B). Generation of CPEP$^+$ cells was in general less efficient in MShef-7 cultures compared to HUES4 (FIG. 6C). However, sorted and re-plated GP2$^{High}$ MShef-7 cells generated significantly higher numbers of CPEP$^+$ cells compared to unsorted and GP2$^{Low}$ cells (FIGS. 6D-6F, Figure S5C,D of Ameri et al. 2017). Slightly more GLU$^+$ cells were observed with the MShef-7 cell line in comparison to the HUES4 cell line (5.0% vs 3.2%), and analogous to the HUES4 cultures, GP2$^+$ purification resulted in an enrichment of GLU$^+$ cells (11.1% vs 8.3%) (FIG. 6G). Similarly, the majority of the CPEP$^+$ cells were mono-hormonal and PDX1 and CPEP$^+$/NKX6.1$^+$ co-expressing cells were also observed (Figure S5D, 6E of Ameri et al. 2017). Importantly, the CPEP$^+$ cells derived from the GP2$^{High}$ cells were also glucose responsive (FIG. 6H). Altogether, these results substantiate the use of GP2 in isolating PECs with the capacity to differentiate into beta-like cells.

Silencing of CDKN1A or CDKN2A Promotes Cell Cycle Progression of GP2$^+$ PECs

Current differentiation protocols of insulin-producing beta-like cells from hPSCs do not support significant expansion of PECs, suggesting that PEC proliferation is inhibited in vitro. Indeed, directed differentiation of hESCs towards pancreatic endoderm is associated with a decrease in proliferation (Figure S6A of Ameri et al. 2017). While MKI67 expression is maintained until day 11, it drops concomitant with increased expression of PDX1 and NKX6.1 (Figure S6A,B of Ameri et al. 2017). Consistently, microarray analysis revealed that the negative cell cycle regulators CDKN1A (p21) and CDKN2A (p16) were specifically enriched in the PDX1$^+$/NKX6.1$^+$ PECs at day 17 (Figure S6D of Ameri et al. 2017). Further analysis revealed that the expression of both CDKN1A and CDKN2A increased at day 14 and remained high during subsequent differentiation stages (Figure S6A of Ameri et al. 2017). Both CDKN1A and CDKN2A block cell cycle progression by inhibiting the activity of the cyclin/CDK complexes that regulate progression through the cell cycle (Besson et al., 2008) (Figure S6C of Ameri et al. 2017). To test whether increased expression of CDKN1A and CDKN2A were responsible for the drop in PEC proliferation, differentiated hESCs corresponding to PDX1$^+$/NKX6.1$^+$ late PECs (day 17) were re-seeded, and transfected with siRNA against CDKN1A or CDKN2A. Knockdown efficiency was assessed by qPCR analysis 24 hours after the transfection (Figure S6E,F of Ameri et al. 2017). Unexpectedly, knocking down either CDKN1A nor CDKN2A had no significant impact on EdU incorporation (Figure S6G-I of Ameri et al. 2017) and MKI67 expression (Figure S6J,K of Ameri et al. 2017). We also confirmed that down-regulation of CDKN1A or CDKN2A expression had no negative influence on the differentiation of the PECs, as PDX1 and NKX6.1 expression was comparable to scrambled controls (Figure S6L of Ameri et al. 2017).

Figure 7J:
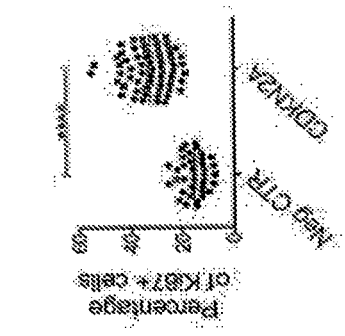
Figure 7K:
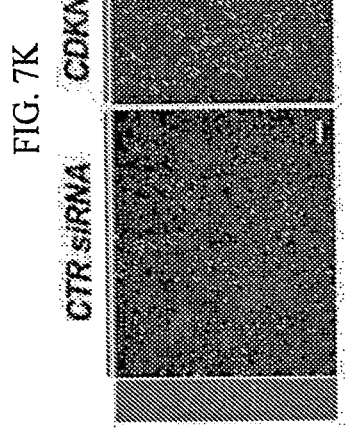
Figure 7L:
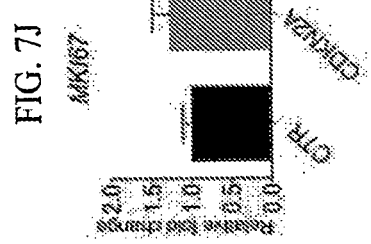

To examine if blocking the increased expression of CDKN1A and CDKN2A at an earlier time-point would increase PEC proliferation, we repeated the knockdown experiments at day 11. Knockdown efficiency was confirmed by qPCR and western blot analysis 24 hours after transfection (Figure S7A-C of Ameri et al. 2017). In contrast to experiments performed at day 17, this time we observed that reduced expression of CDKN1A and CDKN2A resulted in increased number of cells in the G2/M and S phases of the cell cycle, respectively (FIGS. 7A-7C). Interestingly, qPCR analysis confirmed that MKI67 expression increased 24 h after knockdown of CDKN1A but not CDKN2A (FIGS. 7D, 7J). Nevertheless, we observed a significant increase in the number of MKI67$^+$ cells (FIGS. 6E-6F, 6K-6L) as well as in the number of PDX1$^+$/NKX6.1$^+$ PECs 72 h after transfection (Figure S7D,E of Ameri et al. 2017). This increase also correlated with an increase in the total number of cells (Figure S7F of Ameri et al. 2017). Altogether, these results suggest that preventing increased expression of CDKN1A or CDKN2A in early hESC-derived PDX1$^+$/NKX6.1$^{Low}$ PECs enhances their proliferative capacity.

Figure 7M:
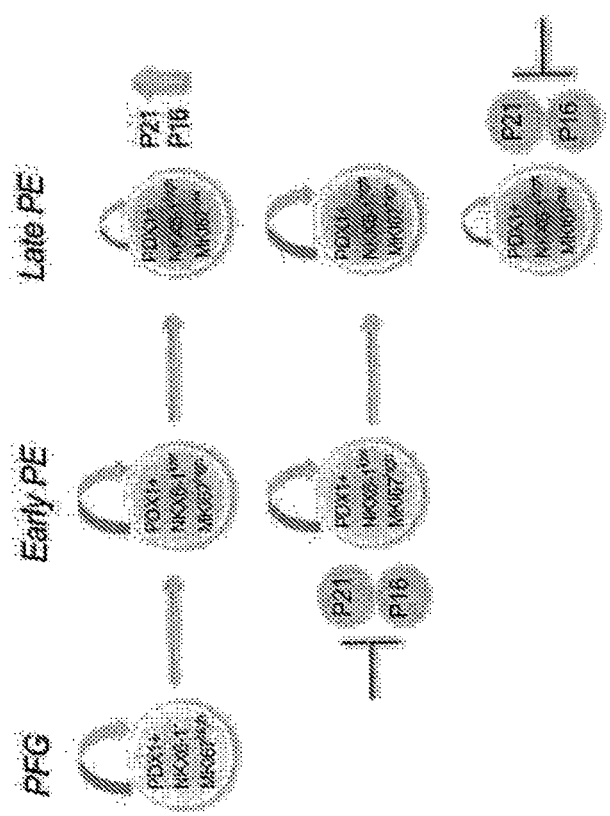

To address whether the CDK inhibitors autonomously affect PEC proliferation, we knocked down the expression of CDKN1A and CDKN2A and subsequently assessed the outcome on the proliferative capacity of GP2$^+$ PECs specifically. Consistent with the results from the unsorted cell population, knockdown of CDKN1A and CDKN2A increased the number of GP2$^+$ PECs that transitioned into the G2/M and S phases of the cell cycle, respectively (Figure S7G-K of Ameri et al. 2017). In sum, by preventing increased expression of CDKN1A and CDKN2A in early hPSC-derived PECs, the proliferative capacity of PECs can be enhanced during in vitro differentiation (FIG. 7M).

Discussion

In this study, we report the identification of a novel cell surface marker, GP2, for efficient purification of human PDX1$^+$/NKX6.1$^+$ PECs endowed with the capacity to give rise to glucose-responsive insulin-producing beta-like cells. Furthermore, by counteracting the increased expression of the cell cycle inhibitors CDKN1A and CDKN2A in the early PECs, the proliferative capacity of hPSC-derived PECs can be sustained in vitro.

The unique experimental design to compare the gene expression pattern in isolated PFG and PE cells allowed us for the first time to identify 115 genes exclusively enriched within human PECs (Table S1 of Ameri et al. 2017). Comparing our PE gene list with a recent study, which systematically analyzed genes expressed in heterogeneous cell populations at intermediate pancreatic differentiation stages (Xie et al., 2013), showed that 16 (including GP2) of our 115 genes overlapped with their "PE genes" (Table S2 of Ameri et al. 2017). This new gene signature of human PE provides a unique source for interrogating unanswered questions in PE biology, such as the molecular machinery involved in PEC maturation (increased expression of NKX6.1) and self-renewal.

Our genome wide expression analysis showed enrichment of the integral membrane protein GP2 in the PDX1$^+$/NKX6.1$^+$ PECs. GP2 expression has previously been described in the acinar cells in the human adult pancreas (Hoops and Rindler, 1991, Yu et al., 2004) (http://www.proteinatlas.org/) but the role and function of GP2 during pancreas development has not been examined. Hence, this is the first report showing that GP2 is expressed in the human PECs and that it can be used as a cell surface marker for isolation of PECs. Furthermore, a comparison between GP2 and the previously published markers CD142 and CD200 (Kelly et al., 2011), demonstrated the superiority of GP2 in labeling PDX1$^+$/NKX6.1$^+$ PECs both in heterogeneous populations of differentiated hESCs as well as in the human fetal pancreas. In addition, the broad applicability of GP2 as a cell surface marker for isolation of PECs was proven by using independent differentiation protocols and cell lines.

During development, proliferation of pancreatic progenitor cells is promoted by factors secreted by the surrounding mesenchymal tissue (Attali et al., 2007, Bhushan et al., 2001, Ye et al., 2005). Co-culture of pancreatic endoderm and mesenchymal cells promote expansion of the PDX1$^+$ population while maintaining its progenitor identity. These activities are in part mediated by FGF10 and EGF signaling (Attali et al., 2007, Bonfanti et al., 2015, Guo et al., 2013, Zhang et al., 2009). However, the underlying mechanism for how these factors promote pancreatic progenitor proliferation has not been elucidated. Here, we identify the cell cycle inhibitors CDKN1A and CDKN2A as relevant regulators of PECs proliferation during in vitro differentiation. We show that increased expression of PDX1 and NKX6.1, a hallmark of late PECs, coincides with increased expression of CDKN1A and CDKN2A and a significant decrease in the proliferative capacity of PECs. Moreover, our observation that lowered expression of CDKN1A and CDKN2A sustains proliferation of early PECs are consistent with previous work linking repression of CDKN1A and CDKN2A activities to self-renewal and expansion of other stem cell or progenitor populations (Kippin et al., 2005, Koike et al., 2014, Orford and Scadden, 2008).

Although reduction of both CDKN1A and CDKN2A levels promotes an overall increase in proliferation of early PECs, their effect on cell cycle progression as well as the immediate impact on MKI67 expression differs, suggesting different mechanisms of action. CDKN1A and CDKN2A belong to different families of CDK inhibitors. CDKN1A is a member of the Cip/Kip family and binds to multiple Cdk-cyclin complexes, inhibiting their catalytic activities at the $G_1$/S- and $G_2$/M-phase checkpoints. CDKN2A belongs to the INK4 family and blocks entry into the S phase by targeting the CDK4/6-cyclin complexes that are present in G1 phase (Besson et al., 2008, Donovan and Slingerland, 2000, Yoon et al., 2012) (Figure S6C of Ameri et al. 2017). It is possible that the activation of a broader range of Cdk-cyclin complexes upon reduction of CDKN1A levels results in a faster progression through the cell cycle compared to the CDKN2A knockdown. This may explain the observed differences in the number of cells in the $G_2$/M- and S-phase. This notion could also explain the lack of immediate transcriptional effect on MKI67 upon reduced CDKN2A levels, compared to CDKN1A. Still, as knocking down the expression of either CDKN1A or CDKN2A promotes proliferation of PECs, they both remain relevant targets for future in vitro expansion of PECs.

Interestingly, we observed that only when the expression of CDKN1A and CDKN2A was decreased in early PECs, proliferation was restored. Previous studies have shown that Neurog3 controls cell cycle exit in mouse endocrine progenitors at least in part through regulation of CDKN1A expression (Miyatsuka et al., 2011, Piccand et al., 2014). Time course analysis of differentiated hESCs indicates that NEUROG3 transcription is initiated in the late PECs (data not shown), suggesting that NEUROG3 may be responsible for the sustained expression of at least CDKN1A in the late PECs. However, since knocking down the expression of CDKN1A and CDKN2A in late PECs is not sufficient to reinstate the proliferative capacity of these cells, additional modulators downstream of NEUROG3 must be involved in regulating proliferation and cell cycle exit in late PECs.

Future clinical trials aiming to test the safety and efficacy of hPSCs-derived beta cells in type 1 diabetes will profit from implementing new cost-effective strategies for cell purification. We envision that using isolated GP2+ PECs for derivation of insulin producing cells for clinical use will significantly improve the safety of the final product. Furthermore, GP2+ PECs can be used to establish an intermediate-stage stem cell bank, permitting the use of more mature yet proliferative cells as a source of functional beta cells. Thus, future studies will need to focus on identifying conditions for in vitro expansion of GP2+ PECs. We foresee a strategy that combines pharmacological targeting of the underlying machinery that regulates proliferation through CDKN1A and/or CDKN2A with growth promoting signals, such as FGFs and EGF. Once this has been achieved additional experiments will be required to characterize the maintenance of the PEC phenotype, as well as the capacity to differentiate into functional beta cells over sequential passages.

EXPERIMENTAL PROCEDURES

Cell Culture and Differentiation

The PDXeG clone 170-3 was maintained on MEFs in medium containing KO-DMEM, 10% knockout serum replacement (Ko-SR), 10 ng/ml bFGF, 1% non-essential amino acids (NEAA), 1% Glutamax, and beta-Mercaptoethanol (all reagents from Life Technologies). HUES4 and the PDXeG clone 170-3 were adapted and maintained in DEF™-CS (Takara) whereas MShef-7 was maintained on laminin-521 (LN521, Biolamina) in Nutristem hESC XF medium (Biological Industries). Detailed information regarding the differentiation protocols can be found in the Supplemental Experimental Procedures.

RNA Extraction and Real-Time qPCR

Total RNA was extracted with GenElute Mammalian total RNA kit (Sigma-Aldrich). Reverse transcription was performed with SuperScript III, according to the manufacturer's instructions, using 2.5 µM random hexamer and 2.5 µM oligo(dT) (Invitrogen). Real-time PCR measurements were performed using the StepOnePlus™ system (Applied Biosystems) with SuperMix-UDG w/ROX, 400 nM of each primer, 0.125×SYBR Green I (all reagents from Life Technologies), with the exception of the qPCR data in FIGS. 5A-5H and 6A-6H which was generated using the LightCycler 48011 (Roche) with PowerSYBR Green PCR Master Mix (AppliedBiosystems) and 500 nM of each primer. Primer sequences are available as supplementary data (Table S3 of Ameri et al. 2017) and in our previous publication (Ameri et al., 2010). The data is shown as mean expression+/−standard error of the mean (SEM). Relative gene expression was determined using ACTB or GAPDH expression as housekeeping genes. When indicated the control sample was arbitrarily set to a value of one in the graphs representing the fold increase in comparison to the control sample.

Microarray Analysis of PDXeG Sorted Populations

Four replicates for each sample were collected by FACS. RNA isolation was performed with the GenElute Mammalian total RNA kit (Sigma-Aldrich). cDNA was synthesized and amplified using Ovation RNA amplification system (NuGEN) according to manufactures instructions. The labeled samples were hybridized to the Human Gene 1.0 ST GeneChip array (Affymetrix, Santa Clara, Calif., USA). The arrays were washed, stained with phycoerytrin conjugated streptavidin (SAPE) using the Affymetrix Fluidics Station® 450, and scanned in the Affymetrix GeneArray® 3000 7G scanner to generate fluorescent images, as described in the Affymetrix GeneChip® protocol. Cell intensity files (CEL files) were generated in the GeneChip® Command Console® Software (AGCC) (Affymetrix, Santa Clara, Calif., USA). Additional information can be found in the Supplemental Experimental Procedures.

Glucose-Stimulated Insulin Secretion (GSIS) Assay

Late stage cultures of differentiated hESCs were washed twice with Krebs-Ringer Bicarbonate buffer (KRB) containing 2 mM glucose. Samples were incubated for two hours in 2 mM glucose containing KRB to allow equilibration of cells. Fresh KRB containing 2 mM glucose was added and cells were incubated for 30 minutes, medium was collected, cells were washed and incubated for 30 minutes in KRB containing 25 mM glucose. Medium was collected, cells were washed again and incubated with final KRB containing 2 mM glucose and 25 mM KCl. All samples were analyzed for human C-peptide content using a commercially available kit from Mercodia.

siRNA Knockdown in Differentiated hESCs

Differentiated hESCs corresponding to day 11 or day 17 were dissociated and transfected with 40 nM CDKN1A, CDKN2A, or scrambled siRNA control (Silencer Select siRNA, ThermoFisher Scientific) using Lipofectamine RNAiMAX (TermoFisher Scientific). 24 hr after transfection cells were harvested for qPCR and 72 h later cells were harvested for immunostainings, western blot analysis and/or treated with EDU for cell cycle analysis. Immunofluorescence stainings were analyzed with Leica AF6000 epifluorescence widefield screening microscope.

Cell Cycle Analysis by Flow Cytometry

For cell cycle analysis with flow cytometry, cells were incubated with EdU (5-Ethynyl-2'-deoxyUridine) at a concentration of 10 µM for four hours before dissociation. Collected samples were live-stained with GP2 and fixed with 4% PFA. EdU was revealed by the Click-it EdU Alexa 647 Flow Cytometry Assay kit (Invitrogen). Compatible PI staining was added to visualize the cell cycle profile based on DNA content. Analysis was performed using BD LSR Fortessa (BD Biosciences). 10,000 events were recorded and doublets were excluded.

Data Analysis and Statistics

Fiji (ImageJ) software was used for all quantifications. The percentage of CPEP+ and GLU+ cells was calculated by measuring area of CPEP or GLU over DAPI area. The percentage of MKI67+ cells was calculated by measuring the area of MKI67/area of PDX1. The total area was estimated by PDX1 antibody staining and DAPI. The percentage of PECs was quantified by measuring the area of NKX6.1 over PDX1 area. 20-25 randomly selected fields were chosen for each parameter. All data were statistically analyzed by unpaired or paired Student's t-test or by multivariate comparison (one-way ANOVA) with Bonferroni correction using GraphPad Prism 6 Software (GraphPad Software, USA). All values are depicted as mean±standard error of the mean (SEM) and considered significant if $p<0.05$.

Human ES Cell Culture and Differentiation

Undifferentiated HUES4, obtained from D. A. Melton, Howard Hughes Medical Institute (Harvard University, Cambridge, Mass.) were maintained on irradiated mouse embryonic fibroblasts (MEFs) (derived by Lund Transgenic Core Facility, Lund University and the Transgenic Mice Core Facility, University of Copenhagen) in medium containing KO-DMEM, 10% knockout serum replacement (KoSR), 1% non-essential amino acids (NEAA), 1% Glutamax, and beta-Mercaptoethanol (Life Technologies) and 10 ng/ml bFGF (Peprotech). Cells were passaged with Accutase (Life Technologies) and re-plated at a split-ratio between 1:3 and 1:4. For feeder free culture, HUES4 and the PDXeG clone 170-3 were adapted and maintained in DEF™-CS (Takara) and passaged with TrypLE E (Life Technologies). Undifferentiated MShef-7 cells obtained from the Centre for Stem Cell Biology, University of Sheffield, were maintained on laminin-521 (LN521, Biolamina) in NutriStem hESC XF medium (Biological Industries).

Cells were passaged with dissociation buffer (0.5 mM EDTA). Karyotyping was performed by standard G-banding, and for each analysis 20-25 metaphases were evaluated (Institute for Clinical Genetics at the Universities of Lund, Sweden and Cell Guidance Systems, Cambridge, UK).

Differentiation Protocol A and B hESCs cultured on MEFs were grown until 90% confluency and differentiated into definitive endoderm (DE) by using a modified version of the D'Amour protocol (D'Amour et al., 2005). The first day of differentiation, hESCs were cultured in the presence of 100 ng/ml human Activin A (Peprotech) and 25 ng/ml Wnt3a (R&D systems) in RPMI medium (Life Technologies). The four following days 100 ng/ml human Activin A was added together with 1×B27−insulin in RPMI medium (Life Technologies). To generate PECs, DE cells were first treated with 2 µM retinoic acid (RA, Sigma Aldrich) in DMEM/F12 medium containing 1×B27+insulin (Life Technologies) for 3 days and then finally treated with 64 ng/ml FGF2 in combination with 100 ng/ml Noggin (Peprotech) for the remaining 9 days. To generate PFG cells, DE cells were treated with 64 ng/ml FGF2 in DMEM/F12 medium containing 1×B27+insulin (Life Technologies) for 12 days.

Differentiation Protocol C

Feeder-free HUES4 and MShef-7 cells were differentiated in RPMI medium containing 100 ng/ml Activin A (Peprotech) and 3 µM CHIR99021 (SMS-Gruppen) the first day, and then with 100 ng/ml human Activin A together with B27-Insulin for the remaining 4 days. At day 5 and the following 3 days, 2 µM retinoic acid was added in DMEM/F12 medium containing 1×B27+insulin. At day eight, cells were washed, and human FGF2 was added (64 ng/ml) on occasions together with human Noggin (50 ng/ml, Peprotech) in a DMEM/F12 medium supplemented with 1×B27+insulin. Medium was changed on a daily basis throughout the protocol. To promote differentiation to insulin producing cells, the cells at day 11 were treated with TPB (0.5 µM, Millipore) and Noggin (100 ng/ml) for 3 days and for the remaining days (up to day 32), cells were treated with Forskolin (10 µM, Sigma Aldrich), Alk5 inhibitor (4.5 µM, Santa Cruz), Nicotinamide (10 mM, Sigma Aldrich), Noggin (100 ng/ml) in DMEM/F-12 medium containing B27 Supplement (1×). The medium was replaced every second day from day 17 and onwards.

Modified Rezania Protocol

The PDXeG clone 170-3 adapted to feeder-free conditions was differentiated into pancreatic endoderm following Rezania et al 2013 (Rezania et al., 2013) with slight modifications. Definitive endoderm was induced according to Funa et al 2015 (Funa et al., 2015). The cells were then cultured for 2 days with 50 ng/ml FGF7 (Peprotech) in DMEM/F12 containing 1×B27+insulin, 2 g/l sodium bicarbonate (Sigma) and 0.25 mM vitamin C (Sigma). The cells were then incubated with 2 ng/ml FGF7, 0.25 µM SANT1 (Sigma), 2 µM retinoic acid (RA, Sigma Aldrich) and 100 ng/ml Noggin in DMEM high glucose (Life Technologies) supplemented with 1×B27+insulin, 2 g/l sodium bicarbonate and 0.25 mM vitamin C for 4 days. Finally, the cells were incubated with 100 ng/ml Noggin and 500 nM TPB in DMEM high glucose (Life Technologies) supplemented with 1×B27+insulin, 2 g/l sodium bicarbonate and 0.25 mM vitamin C for 3-5 days.

Generation of a hESC-Derived PDX1-eGFP (PDXeG) Reporter Cell Line

The PDX1-targeting vector was constructed by inserting an eGFP-pSV40-Neo® reporter cassette upstream of the PDX1 start codon (ATG), resulting in an GFP-tagged PDX1 allele. The GFP cassette was flanked by a 12.5 kb 5'homologous arm and by a 3.5 kb 3'homologous arm. The bacterial artificial chromosome (BAC) containing the human PDX1 locus (CTD-2270K21) purchased from Life Technologies was verified by restriction enzyme digestion and sequencing. The final targeting construct was verified by PCR, restriction analysis and sequencing. The cloning of the GFP-cassette, targeting and drug selection was performed as previously published (Fischer et al., 2010). After approximately 2 weeks emerging clones were picked, expanded and analyzed by PCR. The Neomycin cassette was deleted by using a CRE expression vector (NLS-CRE-IRES-Puro) that was transiently co-transfected with a DsRED or GFP plasmid into selected targeted cloned. 24 hours post electroporation, GFP/DsRED positive single cells were FACS sorted and plated into 96-well plates. Clones were expanded and characterized for Neo excision by PCR.

Copy Number Determination

The copy number of the PDX1 targeting vector in PDXeG cells was determined by qPCR as previously described (Hoebeeck et al., 2005). A fragment of the PDX1 proximal promoter was amplified and quantified relative to the copy number of the single-copy reference genes ZNF80 and GPR15. Copy numbers of the PDX1 promoter fragment (pPDX1) was calibrated by comparing to untransfected hESCs (control) and normalized to the geometric mean of two reference genes (ZNF80 and GPR15), using the amplification efficiency adjusted ΔΔCt method as previously described (Fischer et al., 2010). Measurements on all samples were performed in quadruple Statistical significance of different pPDX1 quantities between samples was analyzed with one-way ANOVA.

Differential Expression Analysis

The raw data (CEL files) were imported into the R where they were normalized using Robust MultiChip Average (RMA) using quantile normalization and Median Polish summarization. Class comparison of the expression profiles of the three conditions, PEC-GFP-plus, PEC-GFP-minus, and PFG-GFP-plus was conducted and probe sets were defined as being differentially expressed when they were selected in the paired t-test, having p-values below 0.005 and a fold-change above 1.4. All samples are MIAME compliant and were handled according to SOP in the microarray Center (http://www.rhmicroarray.com). The 12 arrays were submitted to ArrayExpress at EMBL using MIAMExpress. The experiment accession number is E-MTAB-5088. Intersections of the gene lists generated in the three comparisons; PEC-GFP-plus versus PEC-GPF-minus, PEC-GFP-plus versus PFG-GFP-plus, and PEC-GFP-minus versus PFG-GFP-plus were visualized in a Venn diagram. The expression pattern of the 3791 unique probe sets in the unions set of the three comparisons was visualized in a hierarchical clustering using Euclidean distance and average linkage.

Gene Ontology Enrichment Analysis

The 115 gene list was used to interrogate the MSigDB for overlaps using the Biological Process gene sets group (C5 gene set) in the MSigD (http://www.broadinstitues.org/gsea/msigdb/annotate.jsp). Enriched functions were defined by a FDR, q-value below 0.05. In the cases where several biological processes represented the same biological function, the –log q value is mean of the –log q of the grouped processes. The bar graph shows the level of enrichment by –log q.

Immunohistochemical Analysis of hESCs hESCs were fixed in 4% paraformaldehyde for 15 minutes at room temperature and washed three times in PBS. Fixed cells were permeabilized with 0.5% Triton X-100 in PBS for 15 minutes and blocked in PBS-T (0.1% Triton X-100 in PBS) supplemented with 5% normal donkey serum (Jackson lmmunoresearch) for 1 h at room temperature before overnight incubation (at 4° C.) with the following primary antibodies: goat anti-PDX1 (R&D systems, 1:500), mouse anti-NKX6.1 (DSHB, 1:200) rabbit anti-SOX-9 (Chemicon, 1:500), goat anti-GFP (Abcam, 1:500), rabbit anti-GFP (Abcam, 1:1000), rabbit anti-MKI67 (Abcam; 1:1000), rat anti-C-PEPTIDE (DSHB, 1:1000), Guinea Pig anti-INSULIN (Daco, 1:1000), Guinea Pig anti-GLUCAGON (Linco Research, 1:1000). After overnight incubation cells were washed three times for 10 minutes in PBS, and incubated with corresponding fluorescent secondary antibodies (Alexa 488 and 647, and Cy3; Jackson lmmunoresearch and Invitrogen; 1:500-1:1000) for 60 min in blocking buffer at room temperature. Cell nuclei were visualized with DAPI (Sigma-Aldrich; 1:10000). Immunofluorescence stainings were detected and analyzed on a Zeiss Axioplan 2 or with a Zeiss LSM780 confocal microscope.

FACS Sorting and Re-Plating of Differentiated hESCs

Differentiated cells were dissociated with Accutase for 10-15 min at 37° C. The cells were then washed twice in FACS buffer (PBS, 0.5% BSA). For cell sorting, GFP+ and GFP− hESCs were isolated using a DiVa flow cytometer with DiVa software (BD Biosciences). Re-analysis after cell sorting confirmed that the purity of the sorted populations was >95%. Approximately 150000-500000 cells were sorted from each subpopulation and used for mRNA extraction. For stainings, the cell pellet was resuspended in FACS buffer and then incubated with following antibodies (20 µl antibody/million cells) for 1 h on ice: mouse anti-GP2-PE (Nordic Biosite), mouse anti-ITGA4-PE (BD Biosciences), mouse anti-ITGA4-APC (BD Biosciences), mouse anti-FOLR1-APC (R&D systems). 7-Aminoactinomycin D (7AAD) or DAPI was used to remove dead cells. Stained cells were analyzed and sorted using a BD FACS Aria III cell sorter (BD Biosciences). For re-plating experiments, cells were sorted in PBS containing 0.5% BSA and then gently pelleted and re-suspended in differentiation medium supplemented with 10-15 µM Y27632.

Flow Cytometry and qPCR Analysis of Human Fetal Pancreas

Human fetal pancreases from 9.1 weeks of development were dissected and dissociated into single cell suspension by using collagenase V (0.5 mg/ml, SIGMA) and trypsin-EDTA 0.05% (Gibco). Single cell suspensions were incubated with the following human antibodies: anti-CD45 (Biolegend, clone H130), anti-CD31 (Biolegend, clone WM59), anti-GP2 (CliniSciences, clone D277-5) and anti-ITGA4 (Biolegend, clone 9F10) for 20 minutes in HBSS supplemented with 3% of fetal calf serum (FACS medium). After incubation, cells were washed and re-suspended in FACS medium with Propidium Iodide (0.5 mg/ml). Cells were sorted with a FACS Aria III from BD Bioscience. cDNA was isolated using the CellsDirect kit from Invitrogen. Cells were sorted directly into PCR tubes containing cells direct 2× reaction buffer (5 µl/tube), 0.2× Assay mix (containing Taqman primers diluted (1/100) into TE buffer (0.1 mM EDTA+10 mM Tris in water), 2.5 µl/tube), Super-Script™ RT/Platinium® TaqMix (0.2 µl/tube) and TE buffer (1.3 µl/tube). A minimum of 50 cells were sorted per tube and the sorted cells were stored at −80° C. Prior to the qPCR analysis, RT and the pre-amplification were done using the thermo-cycler (GeneAmp PCR System 9700 Applied Biosystems). qPCR analysis was performed using TaqMan primers: PDX1 (Hs00236830_m1), NKX6.1 (hs00232355_m1) and PP/A (Hs04194521_s1) and TaqMan Universal Master Mix (Applied Biosystem). Relative gene expression was determined using PP/A as a housekeeping gene.

Western Blot Analysis

Cells were lysed in RIPA lysis buffer (50 mM Tris pH 8.0, 150 mM NaCl, 5 mM EDTA pH 8.0, 1% NP-40, 0.5% sodium deoxycholate, 0.1% SDS) containing complete protease inhibitor cocktail (Roche). Cell lysates were resolved on 4-12% SDS-PAGE gels (NuPAGE, Invitrogen). The samples were then electrotransferred to nitrocellulose membranes and immunoblotted with antibodies against p21 (Cell Signaling 1:1000), PDX1 (R&D systems 1:500), NKX6.1 (DSHB 1:1000). Vinculin (Sigma-Aldrich 1:50000) was used as a loading control. HRP conjugated secondary antibodies (Jackson ImmunoResearch) were used for enhanced chemiluminescence detection (GE Healthcare).

Supplemental Data

Supplemental data, figures and tables can be found in Ameri et al. 2017 and are incorporated herein in their entirety.

REFERENCES

Ameri J et al. (2010) Stem Cells 28(1):45-56
Ameri J et al. (2017) Cell Reports 19: 36-49
Aoi, T. et al. (2008) Nihon Rinsho. 66(5):850-6
Attali M. et al. (2007) *Diabetes*, 56, 1248-58.
Besson A. et al. (2008) *Dev Cell*, 14, 159-69.
Bhushan A et al., (2001) *Development*, 128, 5109-17.
Bonfanti P. et al. (2015) *Stem Cells Dev*, 24, 1766-78.
Bruni A et al. (2014) *Diabetes Metab Syndr Obes*, 7, 211-23.
Castaing M. et al (2015) *Dev Dyn*, 234, 339-45.
Cheng X. et al. (2012) *Cell Stem Cell*, 10, 371-84.
Chung et al. (2008) Cell Stem Cell. 2(2):113-7.
D'Amour et al., (2005) *Nat Biotechnol*, 23, 1534-41.
D'Amour, K. A. et al. (2006) Nat Biotechnol. (11):1392-401.
Donovan J. et al (2000) *Breast Cancer Res*, 2, 116-24.
Elghazi L. et al (2002) *Proc Natl Acad Sci USA*, 99, 3884-9.
Fischer Y. et al. (2010) *PLoS One*, 5.
Funa N. S. et al. (2015) *Cell Stem Cell*, 16, 639-52.
Gu G. et al. (2002) *Development*, 129, 2447-57.
Guo T. et al. (2013) *Diabetes*, 62, 1581-92.
Heins et. al. (2004) Stem Cells. 22(3):367-76.
Herrera P. L. (2002). *Int J Dev Biol*, 46, 97-103.
Hoebeeck J. et al. (2005) *Lab Invest*, 85, 24-33.
Holland et al. (2006) Genesis 44(6):304-307
Hoops T. C. et al. (1991). *J Biol Chem*, 266, 4257-63.
Jennings R. E. et al (2013) *Diabetes*, 62, 3514-22.
Jiang, J. et al. (2007), Stem Cells 25
Jiang, J. et al. (2011) Stem Cells. 29(4):609-17
Kawaguchi et al. (2002) *Nat Genet*, 32, 128-34.
Kelly et al. (2011) Nat Biotechnol. (29): 750-756.
Kippin T. E. et al (2005) *Genes Dev*, 19, 756-67.
Koike H. et al. (2014) *Hepatology*, 60, 323-33.
Kopp J. L. et al (2011) *Development*, 138, 653-65.
Kroon, E. et al. (2008) Nat Biotechnol. 26(4):443-52.
Miyatsuka T. et al. (2011) *Proc Natl Acad Sci USA*, 108, 185-90.
Nair G. et al (2015) *Curr Opin Genet Dev*, 32, 171-80.
Naujok and Lenzen (2012) Stem Cell Rev. 8(3):779-91.
Orford K. W. et al (2008) *Nat Rev Genet*, 9, 115-28.
Pagliuca et al. (2014) Cell. 159(2):428-39
Piccand J. et al. (2014) *Diabetes*, 63, 203-15.
Rezania et al. (2010) Eur J Pharmacol. 627(1-3):265-8
Rezania et al. (2012) Diabetes. 2012 August; 61(8):2016-29.
Rezania et al. (2013) Stem Cells 31(11):2432-42
Rezania et al. (2014) Nat Biotechnol. (32):1121-33.
Russ H. A. et al. (2015) *EMBO J*, 34, 1759-72.
Schaffer A. E. et al. (2010) *Dev Cell*, 18, 1022-9.
Schulz T. C. et al. (2012) *PLoS One*, 7, e37004.
Seymour P. A. et al. (2007) *Proc Natl Acad Sci USA*, 104, 1865-70.
Shapiro et al. (2000) N Engl J Med 343:230-238
Shapiro et al. (2001a) Best Pract Res Clin Endocrinol Metab 15:241-264
Shapiro et al. (2001b) British Medical Journal 322:861
Sneddon J. B. et al. (2012) *Nature*, 491, 765-8.
Stadtfeld and Hochedlinger (2010) Genes Dev. 24(20):2239-63
Stanger B. Z. et al. (2007) *Nature*, 445, 886-91.
Takahashi and Yamanaka (2006) Cell. 2006 Aug. 25; 126 (4):663-76
Takahashi et al. (2007) Cell 131 (5):861
Takashima et al. (2014) Cell. 158(6): 1254-1269
Tesar et al. (2007) Nature 448(7150):196-9
Thomson, A. et al. (1998) Science. 6; 282(5391):1145-7.
Wernig, M. et al. (2007) Nature. 448(7151):318-24
Xie R. et al. (2013) *Cell Stem Cell*, 12, 224-37.
Ye F. et al. (2005) *Diabetologia*, 48, 277-81.
Yoon M. K. et al. (2012) *Biochem Soc Trans*, 40, 981-8.
Yu et al., (2007) Science 318:5858
Yu J, et al. (2009) Science vol 324
Yu S. et al. (2004) *J Biol Chem*, 279, 50274-9.
Zhang D. et al. (2009) *Cell Res*, 19, 429-38.
Zhu S. et al. (2016) *Nat Commun*, 7, 10080.

The invention claimed is:

1. A method of generating glucose-responsive, insulin-producing beta cells, comprising providing a starting cell population comprising at least one cell capable of differentiation; wherein the cell capable of differentiation is a pluripotent stem cell, the method comprises:
   i) incubating said cell population in RPMI medium comprising Activin A and a glycogen synthase kinase (GSK3) inhibitor for a duration sufficient to differentiate at least part of the cell population into definitive endoderm cells;
   ii) incubating the cell population of i) in RPMI medium comprising B27−insulin, for a duration sufficient to further differentiate the cell population into definitive endoderm cells;
   iii) incubating the cell population of ii) in DMEM/F12 medium comprising B27+insulin and retinoic acid, for a duration sufficient to differentiate at least part of the cell population into gut tube cells;
   iv) incubating the cell population of iii) in DMEM/F12 medium comprising B27+insulin and human FGF2, and optionally human Noggin, for a duration sufficient to differentiate at least part of the cell population into posterior foregut cells;
   v) incubating the cell population of iv) in DMEM/F12 medium comprising B27+insulin, ((2S,5S)-(E,E)-8-(5-(4-(Trifluoromethyl)phenyl)-2,4-pentadienoylamino) benzolactam) (TPB), and human Noggin for a duration sufficient to differentiate at least part of the cell population into early pancreatic progenitor cells; and
   vi) incubating the cell population of v) in DMEM/F12 medium comprising B27+insulin, Forskolin, Alk5 inhibitor, Nicotinamide, and human Noggin for a duration sufficient to differentiate at least part of the cell population into mature GP2+ pancreatic progenitor cells expressing PDX1 and NKX6.1 and sufficient to enhance viability of the mature GP2+ pancreatic progenitor cells expressing PDX1 and NKX6.1; and
   vii) incubating the cell population obtained in vi) in DMEM/F12 medium comprising B27+insulin, Forskolin, Alk5 inhibitor, Nicotinamide, human Noggin without Rock inhibitor for a duration sufficient to differentiate at least part of the cell population into glucose-responsive, insulin-producing beta cells.

2. The method according to claim 1, wherein the RPMI medium of i) comprises between 1 and 500 ng/mL Activin A.

3. The method according to claim 1, wherein the RPMI medium of i) comprises between 1 and 100 µM of a glycogen synthase kinase (GSK3) inhibitor.

4. The method according to claim 1, wherein the DMEM/F12 medium of at least one of iii) to vii) ii) to vi) comprises 1×B27+insulin.

5. The method according to claim 1, wherein the DMEM/F12 medium of iii) comprises between 0.5 and 10 µM retinoic acid.

6. The method according to claim 1, wherein the DMEM/F12 medium of iv) comprises between 10 and 200 ng/mL human FGF2.

7. The method according to claim 1, wherein the DMEM/F12 medium of at least one of iv) to vii) comprises between 10 and 500 ng/mL human noggin.

8. The method according to claim 1, wherein the DMEM/F12 medium of v) comprises between 0.1 and 10 µM TPB.

9. The method according to claim 1, wherein the DMEM/F12 medium of vi) and/or vii) comprises between 1 and 500 µM Forskolin.

10. The method according to claim 1, wherein the DMEM/F12 medium of vi) and/or vii) comprises between 1 and 100 µM Alk5 inhibitor.

11. The method according to claim 1, wherein the DMEM/F12 medium of vi) and/or vii) comprises between 1 and 100 mM Nicotinamide.

12. The method according to claim 1, wherein the medium of at least one of vi) does not comprise bovine serum albumin (BSA).

13. The method according to claim 1, wherein the starting cell population is a population selected from pluripotent stem cells, or nave stem cells.

14. The method according to claim 1, wherein the method further comprises enriching the starting cell population for cells expressing PDX1 and NKX6.1 between v) and vi).

15. The method according to claim 14, wherein enriching the cell population for cells expressing PDX1 and NKX6.1 comprises, in any order:
a) exposing the cell population to a first ligand which binds to a first marker specific for PDX1− cells and selecting the cells that do not bind to said first ligand from said cell population; and/or
b) exposing the cell population to a second ligand which binds to a second marker specific for PDX1+ cells and selecting the cells that bind to said second ligand from the cells that do not bind to said second ligand, thereby enriching the cell population for PDX1+ cells; and/or
c) exposing the cell population to a third ligand which binds to a third marker specific for PDX1+ NKX6.1+ cells and selecting the cells that bind to said third ligand from the cells that do not bind to said third ligand, thereby enriching the cell population for PDX1+ NKX6.1+ cells.

16. The method according to claim 15, wherein the third ligand is an antibody or fragment thereof directed against GP2.

17. The method according to claim 1, wherein the cell population obtained in vii) is capable of producing insulin and/or insulin-producing islet cells.

18. A method of treatment of a metabolic disorder in an individual in need thereof, wherein the method comprises providing a population of insulin-producing beta cells obtained by the method according to claim 1 and transplanting said population of beta cells into said individual.

19. A method of generating glucose-responsive, insulin-producing beta cells, comprising providing a starting cell population comprising isolated GP2+ pancreatic progenitor cells expressing PDX1 and NKX6.1, wherein the method comprises:
i) incubating the starting cell population in DMEM/F12 medium comprising B27+insulin, Forskolin, Alk5 inhibitor, Nicotinamide and human Noggin for a duration sufficient to enhance viability of the GP2+ pancreatic progenitor cells expressing PDX1 and NKX6.1 after cell isolation, wherein the medium also comprises a Rock inhibitor for further increasing the viability of the isolated cells impacted by cell dissociation during cell isolation; and
ii) incubating the cell population obtained in i) in DMEM/F12 medium comprising B27+insulin, Forskolin, Alk5 inhibitor, Nicotinamide, human Noggin without Rock inhibitor for a duration sufficient to differentiate at least part of the cell population into glucose-responsive, insulin-producing beta cells.

20. The method according to claim 19, wherein the DMEM/F12 medium of at least one of i) to ii) comprises between 10 and 500 ng/mL human noggin.

21. The method according to claim 19, wherein the DMEM/F12 medium of i) and/or ii) comprises between 1 and 500 µM Forskolin.

22. The method according to claim 19, wherein the DMEM/F12 medium of i) and/or ii) comprises between 1 and 100 µM Alk5 inhibitor.

23. The method according to claim 19, wherein the DMEM/F12 medium of i) and/or ii) comprises between 1 and 100 mM Nicotinamide.

24. The method according to claim 19, wherein the DMEM/F12 medium of i) comprises between 1 and 100 µM Rock inhibitor.

25. The method according to claim 19, wherein the starting cell population comprising a GP2+ pancreatic progenitor cell expressing PDX1 and NKX6.1 is derived from a population selected from pluripotent stem cells, naïve stem cells, embryonic stem cells, induced pluripotent stem cells, somatic cells or pancreatic progenitor cells.

26. The method according to claim 19, wherein the cell population obtained in ii) is capable of producing insulin and/or insulin-producing islet cells.

27. A method of treatment of a metabolic disorder in an individual in need thereof, wherein the method comprises providing a population of insulin-producing beta cells obtained by the method according to claim 19 and transplanting said population of beta cells into said individual.

* * * * *

UNITED STATES PATENT AND TRADEMARK OFFICE
CERTIFICATE OF CORRECTION

PATENT NO. : 11,060,062 B2
APPLICATION NO. : 15/852900
DATED : July 13, 2021
INVENTOR(S) : Jacqueline Ameri et al.

It is certified that error appears in the above-identified patent and that said Letters Patent is hereby corrected as shown below:

In the Claims

Column 52, Line 60: Remove "ii) to vi)";

Column 53, Line 16: Replace "vi)" with --i) to vii)--; and

Column 53, Line 20: Replace "nave" with --naïve--.

Signed and Sealed this
Fourth Day of October, 2022

Katherine Kelly Vidal
*Director of the United States Patent and Trademark Office*